US012758133B2

(12) United States Patent
Doomra

(10) Patent No.: US 12,758,133 B2
(45) Date of Patent: Oct. 13, 2026

(54) METHODS AND SYSTEMS FOR ENGINEERING VISUAL FEATURES FROM BIOPHYSICAL SIGNALS FOR USE IN CHARACTERIZING PHYSIOLOGICAL SYSTEMS

(71) Applicant: Analytics for Life Inc., Toronto (CA)

(72) Inventor: Abhinav Doomra, North York (CA)

(73) Assignee: Analytics for Life Inc., Toronto (CA)

(*) Notice: Subject to any disclaimer, the term of this patent is extended or adjusted under 35 U.S.C. 154(b) by 563 days.

(21) Appl. No.: 17/891,526

(22) Filed: Aug. 19, 2022

(65) Prior Publication Data

US 2023/0071085 A1 Mar. 9, 2023

Related U.S. Application Data

(60) Provisional application No. 63/236,072, filed on Aug. 23, 2021.

(51) Int. Cl.

*A61B 5/24* (2021.01)
*A61B 5/316* (2021.01)
*G16H 50/20* (2018.01)

(52) U.S. Cl.

CPC ............... *A61B 5/24* (2021.01); *G16H 50/20* (2018.01); *A61B 5/316* (2021.01)

(58) Field of Classification Search

None

See application file for complete search history.

(56) References Cited

U.S. PATENT DOCUMENTS 8,923,958 B2 12/2014 Gupta et al.
9,289,150 B1 3/2016 Gupta et al.
(Continued)

FOREIGN PATENT DOCUMENTS

WO 2017033164 A1 3/2017
WO 2017221221 A1 12/2017
(Continued)

OTHER PUBLICATIONS

International Search Report and Written Opinion issued for Application No. PCT/IB2022/057794, dated Dec. 12, 2022.
(Continued)

*Primary Examiner* — Benjamin J Klein
*Assistant Examiner* — Willow Grace Welch
(74) *Attorney, Agent, or Firm* — Meunier Carlin & Curfman LLC

(57) ABSTRACT

A clinical evaluation system and method are disclosed that facilitate the use of one or more visual features or parameters determined from biophysical signals such as cardiac/biopotential signals and/or photoplethysmography signals that are acquired, in preferred embodiments, non-invasively from surface sensors placed on a patient while the patient is at rest. The visual features or parameters can be used in a model or classifier (e.g., a machine-learned classifier) to estimate metrics associated with the physiological state of a patient, including for the presence or non-presence of a disease, medical condition, or an indication of either. The estimated metric may be used to assist a physician or other healthcare provider in diagnosing the presence or non-presence and/or severity and/or localization of diseases or conditions or in the treatment of said diseases or conditions.

20 Claims, 18 Drawing Sheets
(12 of 18 Drawing Sheet(s) Filed in Color)

(56) References Cited

U.S. PATENT DOCUMENTS

| | | | | |
|---|---|---|---|---|
| 9,408,543 | B1 | 8/2016 | Gupta et al. | |
| 9,597,021 | B1 | 3/2017 | Gupta et al. | |
| 9,655,536 | B2 | 5/2017 | Gupta et al. | |
| 9,737,229 | B1 | 8/2017 | Gupta et al. | |
| 9,910,964 | B2 | 3/2018 | Burton et al. | |
| 9,955,883 | B2 | 5/2018 | Gupta et al. | |
| 9,968,265 | B2 | 5/2018 | Burton et al. | |
| 9,968,275 | B2 | 5/2018 | Gupta et al. | |
| 10,039,468 | B2 | 8/2018 | Gupta et al. | |
| 10,292,596 | B2 | 5/2019 | Shadforth et al. | |
| 10,362,950 | B2 | 7/2019 | Gupta et al. | |
| 10,542,897 | B2 | 1/2020 | Gupta et al. | |
| 10,566,091 | B2 | 2/2020 | Burton et al. | |
| 10,566,092 | B2 | 2/2020 | Burton et al. | |
| 10,672,518 | B2 | 6/2020 | Burton et al. | |
| 10,806,349 | B2 * | 10/2020 | Shadforth | A61B 6/503 |
| 2018/0249960 | A1 | 9/2018 | Gupta et al. | |
| 2018/0261326 | A1 | 9/2018 | Burton et al. | |
| 2019/0026430 | A1 | 1/2019 | Grouchy et al. | |
| 2019/0026431 | A1 | 1/2019 | Grouchy et al. | |
| 2019/0200893 | A1 | 7/2019 | Grouchy et al. | |
| 2019/0214137 | A1 | 7/2019 | Gupta et al. | |
| 2019/0313926 | A1 | 10/2019 | Gupta et al. | |
| 2019/0365265 | A1 | 12/2019 | Grouchy et al. | |
| 2019/0384757 | A1 | 12/2019 | Garrett et al. | |
| 2020/0205739 | A1 | 7/2020 | Garrett et al. | |
| 2020/0205745 | A1 * | 7/2020 | Khosousi | G06F 18/217 |
| 2020/0211713 | A1 * | 7/2020 | Shadforth | G16H 50/50 |
| 2020/0229724 | A1 | 7/2020 | Gupta et al. | |
| 2020/0335217 | A1 | 10/2020 | Burton et al. | |
| 2020/0397322 | A1 | 12/2020 | Paak et al. | |
| 2020/0397324 | A1 | 12/2020 | Paak et al. | |
| 2021/0212582 | A1 | 7/2021 | Fathieh et al. | |
| 2022/0192596 | A1 | 6/2022 | Fathieh et al. | |
| 2023/0055617 | A1 | 2/2023 | Lange et al. | |
| 2023/0071467 | A1 | 3/2023 | Burton et al. | |
| 2023/0072281 | A1 | 3/2023 | Fathieh et al. | |
| 2023/0075570 | A1 | 3/2023 | Fathieh | |
| 2023/0075634 | A1 | 3/2023 | Fathieh et al. | |
| 2023/0076069 | A1 | 3/2023 | Lange et al. | |
| 2023/0127355 | A1 | 4/2023 | Paak et al. | |

FOREIGN PATENT DOCUMENTS

| | | | |
|---|---|---|---|
| WO | 2018158749 | A1 | 9/2018 |
| WO | 2019077414 | A1 | 4/2019 |
| WO | 2019130272 | A1 | 7/2019 |
| WO | 2019130273 | A1 | 7/2019 |
| WO | 2019234587 | A1 | 12/2019 |
| WO | 2019244043 | A1 | 12/2019 |
| WO | 2020136569 | A1 | 7/2020 |
| WO | 2020136570 | A1 | 7/2020 |
| WO | 2020136571 | A1 | 7/2020 |
| WO | 2020254881 | A1 | 12/2020 |
| WO | 2020254882 | A1 | 12/2020 |

OTHER PUBLICATIONS

International Preliminary Report on Patentability issued for Application No. PCT/IB2022/057794, dated Mar. 7, 2024.

European Search Report issued for Application No. 22860719.8, dated Jun. 10, 2025. 14 pages.

* cited by examiner

METHODS AND SYSTEMS FOR ENGINEERING VISUAL FEATURES FROM BIOPHYSICAL SIGNALS FOR USE IN CHARACTERIZING PHYSIOLOGICAL SYSTEMS

RELATED APPLICATION

This US application claims priority to, and the benefit of, U.S. Provisional Patent Application No. 63/236,072, filed Aug. 23, 2021, entitled "Methods and Systems for Engineering Visual Features From Biophysical Signals for Use in Characterizing Physiological Systems," which is incorporated by reference herein in its entirety.

FIELD OF THE INVENTION

The present disclosure generally relates to methods and systems for engineering features or parameters from biophysical signals for use in diagnostic applications; in particular, the engineering and use of visual features for use in characterizing one or more physiological systems and their associated functions, activities, and abnormalities. The features or parameters may also be used for monitoring or tracking, controls of medical equipment, or to guide the treatment of a disease, medical condition, or an indication of either.

BACKGROUND

There are numerous methods and systems for assisting a healthcare professional in diagnosing disease. Some of these involve the use of invasive or minimally invasive techniques, radiation, exercise or stress, or pharmacological agents, sometimes in combination, with their attendant risks and other disadvantages.

Diastolic heart failure, a major cause of morbidity and mortality, is defined as symptoms of heart failure in a patient with preserved left ventricular function. It is characterized by a stiff left ventricle with decreased compliance and impaired relaxation leading to increased end-diastolic pressure in the left ventricle, which is measured through left heart catheterization. Current clinical standard of care for diagnosing pulmonary hypertension (PH), and for pulmonary arterial hypertension (PAH), in particular, involves a cardiac catheterization of the right side of the heart that directly measures the pressure in the pulmonary arteries. Coronary angiography is the current standard of care used to assess coronary arterial disease (CAD) as determined through the coronary lesions described by a treating physician. Non-invasive imaging systems such as magnetic resonance imaging and computed tomography require specialized facilities to acquire images of blood flow and arterial blockages of a patient that are reviewed by radiologists.

It is desirable to have a system that can assist healthcare professionals in the diagnosis of cardiac disease and various other diseases and conditions without the aforementioned disadvantages.

SUMMARY

A clinical evaluation system and method are disclosed that facilitate the use of one or more visual features or parameters determined from biophysical signals such as cardiac/biopotential signals and/or photoplethysmography signals that are acquired, in preferred embodiments, non-invasively from surface sensors placed on a patient while the patient is at rest. The visual features or parameters can be used in a model or classifier (e.g., a machine-learned classifier) to estimate metrics associated with the physiological state of a patient, including for the presence or non-presence of a disease, medical condition, or an indication of either. The estimated metric may be used to assist a physician or other healthcare provider in diagnosing the presence or non-presence and/or severity and/or localization of diseases or conditions or in the treatment of said diseases or conditions.

The estimation or determined likelihood of the presence or non-presence of a disease, condition, or indication of either can supplant, augment, or replace other evaluation or measurement modalities for the assessment of a disease or medical condition. In some cases, a determination can take the form of a numerical score and related information.

For cardiac signals, the visual features are determined in a phase space model of the cardiac or biopotential signals to characterize various properties of repetitive cycles of the cardiac electrophysiological signal, including those of the waveforms associated with atrial depolarization (AD), waveforms associated with atrial repolarization (AR), waveforms associated with ventricular depolarization (VD) and waveforms associated with ventricular repolarization (VR). In some embodiments, visual features include characteristics of the cardiac loops (AD, VD, VR) in the 3D phase space and within the octants of the 3D space. Although referred to as visual features, AR occurs during VD and may not be visible in the phase space view. In some embodiments, visual features include characteristics of the cardiac vectors (e.g., maximal atrial depolarization vector (MADV), atrial repolarization vector (ARV), maximal ventricular depolarization vector (MVDV), initial ventricular depolarization vector (IVDV), terminal ventricular depolarization vector (TVDV), maximal ventricular repolarization vector (MVRV) in the 3D phase space and within the octants (or subregions) of the 3D space. In some embodiments, visual features include characteristics of projections of the cardiac loops (AD, VD, VR) onto the three orthogonal planes and within the quadrants of the respective orthogonal plane. In some embodiments, visual features include characteristics of projections of the cardiac vectors onto the three orthogonal planes and within the quadrants of the respective orthogonal plane.

For photoplethysmographic-related signals, the visual features are determined in a phase space model of a photoplethysmographic signal and velocityplethysmographic and accelerationplethysmographic signals derived from the photoplethysmographic signal and characterize various properties of repetitive cycles of these signals. The term "photoplethysmographic-related" refers to photoplethysmographic and associated velocityplethysmographic and accelerationplethysmographic signals.

As used herein, the term "feature" (in the context of machine learning and pattern recognition and as used herein) generally refers to an individual measurable property or characteristic of a phenomenon being observed. A feature is defined by analysis and may be determined in groups in combination with other features from a common model or analytical framework.

As used herein, "metric" refers to an estimation or likelihood of the presence, non-presence, severity, and/or localization (where applicable) of one or more diseases, conditions, or indication(s) of either, in a physiological system or systems. Notably, the exemplified methods and systems can be used in certain embodiments described herein to acquire biophysical signals and/or to otherwise collect data from a patient and to evaluate those signals and/or data in signal processing and classifier operations to evaluate for a disease, condition, or indicator of one that can supplant, augment, or replace other evaluation modalities via one or more metrics. In some cases, a metric can take the form of a numerical score and related information.

In the context of cardiovascular and respiratory systems, examples of diseases and conditions to which such metrics can relate include, for example: (i) heart failure (e.g., left-side or right-side heart failure; heart failure with preserved ejection fraction (HFpEF)), (ii) coronary artery disease (CAD), (iii) various forms of pulmonary hypertension (PH) including without limitation pulmonary arterial hypertension (PAH), (iv) abnormal left ventricular ejection fraction (LVEF), and various other diseases or conditions. An example indicator of certain forms of heart failure is the presence or non-presence of elevated or abnormal left-ventricular end-diastolic pressure (LVEDP). An example indicator of certain forms of pulmonary hypertension is the presence or non-presence of elevated or abnormal mean pulmonary arterial pressure (mPAP).

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, which are incorporated in and constitute a part of this specification, illustrate embodiments and, together with the description, serve to explain the principles of the methods and systems.

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION

Figure 1:
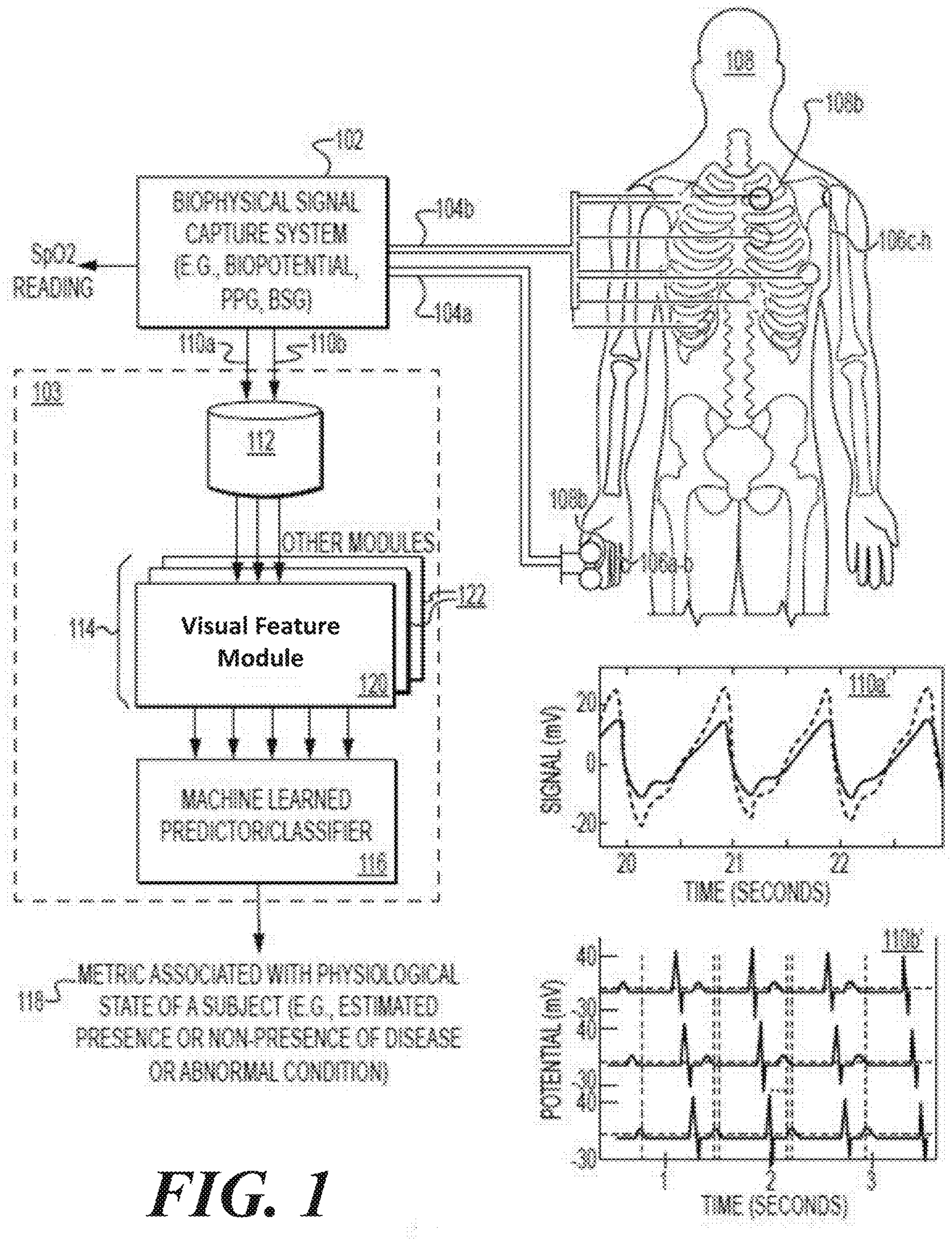
FIG. 1 is a schematic diagram of example modules, or components, configured to non-invasively compute visual features or parameters to generate one or more metrics associated with the physiological state of a patient in accordance with an illustrative embodiment.

Each and every feature described herein, and each and every combination of two or more of such features, is included within the scope of the present invention provided that the features included in such a combination are not mutually inconsistent.

While the present disclosure is directed to the practical assessment of biophysical signals, e.g., raw or pre-processed photoplethysmographic signals, biopotential/cardiac signals, etc., in the diagnosis, tracking, and treatment of cardiac-related pathologies and conditions, such assessment can be applied to the diagnosis, tracking, and treatment (including without limitation surgical, minimally invasive, lifestyle, nutritional, and/or pharmacologic treatment, etc.) of any pathologies or conditions in which a biophysical signal is involved in any relevant system of a living body. The assessment may be used in the controls of medical equipment or wearable devices or in monitoring applications.

The terms "subject" and "patient" as used herein are generally used interchangeably to refer to those who had undergone analysis performed by the exemplary systems and methods.

The term "cardiac signal" as used herein refers to one or more signals directly or indirectly associated with the structure, function, and/or activity of the cardiovascular system—including aspects of that signal's electrical/electrochemical conduction—that, e.g., cause contraction of the myocardium. A cardiac signal may include, in some embodiments, biopotential signals or electrocardiographic signals, e.g., those acquired via an electrocardiogram (ECG), the cardiac and photoplethysmographic waveform or signal capture or recording instrument later described herein, or other modalities.

The term "biophysical signal" as used herein includes but is not limited to one or more cardiac signal(s), neurological signal(s), ballistocardiographic signal(s), and/or photoplethysmographic signal(s), but it also encompasses more broadly any physiological signal from which information may be obtained. Not intending to be limited by example, one may classify biophysical signals into types or categories that can include, for example, electrical (e.g., certain cardiac and neurological system-related signals that can be observed, identified, and/or quantified by techniques such as the measurement of voltage/potential (e.g., biopotential), impedance, resistivity, conductivity, current, etc. in various domains such as time and/or frequency), magnetic, electromagnetic, optical (e.g., signals that can be observed, identified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), thermal, and electrochemical (e.g., signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), one or more organ system(s) (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements, and their subatomic components. Unless stated otherwise, the term "biophysical signal acquisition" generally refers to any passive or active means of acquiring a biophysical signal from a physiological system, such as a mammalian or non-mammalian organism. Passive and active biophysical signal acquisition generally refers to the observation of natural or induced electrical, magnetic, optical, and/or acoustics emittance of the body tissue. Non-limiting examples of passive and active biophysical signal acquisition means include, e.g., voltage/potential, current, magnetic, optical, acoustic, and other non-active ways of observing the natural emittance of the body tissue, and in some instances, inducing such emittance. Non-limiting examples of passive and active biophysical signal acquisition means include, e.g., ultrasound, radio waves, microwaves, infrared and/or visible light (e.g., for use in pulse oximetry or photoplethysmography), visible light, ultraviolet light, and other ways of actively interrogating the body tissue that does not involve ionizing energy or radiation (e.g., X-ray). An active biophysical signal acquisition may involve excitation-emission spectroscopy (including, for example, excitation-emission fluorescence). The active biophysical signal acquisition may also involve transmitting ionizing energy or radiation (e.g., X-ray) (also referred to as "ionizing biophysical signal") to the body tissue. Passive and active biophysical signal acquisition means can be performed in conjunction with invasive procedures (e.g., via surgery or invasive radiologic intervention protocols) or non-invasively (e.g., via imaging, ablation, heart contraction regulation (e.g., via pacemakers), catheterization, etc.).

The term "photoplethysmographic signal" as used herein refers to one or more signals or waveforms acquired from optical sensors that correspond to measured changes in light absorption by oxygenated and deoxygenated hemoglobin, such as light having wavelengths in the red and infrared spectra. Photoplethysmographic signal(s), in some embodiments, include a raw signal(s) acquired via a pulse oximeter or a photoplethysmogram (PPG). In some embodiments, photoplethysmographic signal(s) are acquired from off-the-shelf, custom, and/or dedicated equipment or circuitries that are configured to acquire such signal waveforms for the purpose of monitoring health and/or diagnosing disease or abnormal conditions. The photoplethysmographic signal(s) typically include a red photoplethysmographic signal (e.g., an electromagnetic signal in the visible light spectrum most dominantly having a wavelength of approximately 625 to 740 nanometers) and an infrared photoplethysmographic signal (e.g., an electromagnetic signal extending from the nominal red edge of the visible spectrum up to about 1 mm), though other spectra such as near-infrared, blue and green may be used in different combinations, depending on the type and/or mode of PPG being employed.

The term "ballistocardiographic signal," as used herein, refers to a signal or group of signals that generally reflect the flow of blood through the entire body that may be observed through vibration, acoustic, movement, or orientation. In some embodiments, ballistocardiographic signals are acquired by wearable devices, such as vibration, acoustic, movement, or orientation-based seismocardiogram (SCG) sensors, which can measure the body's vibrations or orientation as recorded by sensors mounted close to the heart. Seismocardiogram sensors are generally used to acquire "seismocardiogram," which is used interchangeably with the term "ballistocardiogram" herein. In other embodiments, ballistocardiographic signals may be acquired by external equipment, e.g., bed or surface-based equipment that measures phenomena such as a change in body weight as blood moves back and forth in the longitudinal direction between the head and feet. In such embodiments, the volume of blood in each location may change dynamically and be reflected in the weight measured at each location on the bed as well as the rate of change of that weight.

In addition, the methods and systems described in the various embodiments herein are not so limited and may be utilized in any context of another physiological system or systems, organs, tissue, cells, etc., of a living body. By way of example only, two biophysical signal types that may be useful in the cardiovascular context include cardiac/biopotential signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography. In another example, the two biophysical signal types can be further augmented by ballistocardiographic techniques.

FIG. 1 is a schematic diagram of example modules, or components, configured to non-invasively compute visual features or parameters to generate, via a classifier (e.g., machine-learned classifier), one or more metrics associated with the physiological state of a patient in accordance with an illustrative embodiment. The modules or components may be used in a production application or the development of the visual features and other classes of features.

The example analysis and classifiers described herein may be used to assist a healthcare provider in the diagnosis and/or treatment of cardiac- and cardiopulmonary-related pathologies and medical conditions, or an indicator of one. Examples include significant coronary artery disease (CAD), one or more forms of heart failure such as, e.g., heart failure with preserved ejection fraction (HFpEF), congestive heart failure, various forms of arrhythmia, valve failure, various forms of pulmonary hypertension, among various other disease and conditions disclosed herein.

In addition, there exist possible indicators of a disease or condition, such as an elevated or abnormal left ventricular end-diastolic pressure (LVEDP) value as it relates to some forms of heart failure, abnormal left ventricular ejection fraction (LVEF) values as they relate to some forms of heart failure or an elevated mean pulmonary arterial pressure (mPAP) value as it relates to pulmonary hypertension and/or pulmonary arterial hypertension. Indicators of the likelihood that such indicators are abnormal/elevated or normal, such as those provided by the example analysis and classifiers described herein, can help a healthcare provider assess or diagnose that the patient has or does not have a given disease or condition. In addition to these metrics associated with a disease state of condition, other measurements and factors may be employed by a healthcare professional in making a diagnosis, such as the results of a physical examination and/or other tests, the patient's medical history, current medications, etc. The determination of the presence or non-presence of a disease state or medical condition can include the indication (or a metric of measure that is used in the diagnosis) for such disease.

In FIG. 1, the components include at least one non-invasive biophysical signal recorder or capture system 102 and an assessment system 103 that is located, for example, in a cloud or remote infrastructure or in a local system. Biophysical signal capture system 102 (also referred to as a biophysical signal recorder system), in this embodiment, is configured to, e.g., acquire, process, store and transmit synchronously acquired patient's electrical and hemodynamic signals as one or more types of biophysical signals 104. In the example of FIG. 1, the biophysical signal capture system 102 is configured to synchronously capture two types of biophysical signals shown as first biophysical signals 104*a* (e.g., synchronously acquired to other first biophysical signals) and second biophysical signals 104*b* (e.g., synchronously acquired to the other biophysical signals) acquired from measurement probes 106 (e.g., shown as probes 106*a* and 106*b*, e.g., comprising hemodynamic sensors for hemodynamic signals 104*a*, and probes 106*c*-106*h* comprising leads for electrical/cardiac signals 104*b*). The probes 106*a-h* are placed on, e.g., by being adhered to or placed next to, a surface tissue of a patient 108 (shown at patient locations 108*a* and 108*b*). The patient is preferably a human patient, but it can be any mammalian patient. The acquired raw biophysical signals (e.g., 106*a* and 106*b*) together form a biophysical-signal data set 110 (shown in FIG. 1 as a first biophysical-signal data set 110*a* and a second biophysical-signal data set 110*b*, respectively) that may be stored, e.g., as a single file, preferably, that is identifiable by a recording/signal captured number and/or by a patient's name and medical record number.

In the FIG. 1 embodiment, the first biophysical-signal data set 110*a* comprises a set of raw photoplethysmographic, or hemodynamic, signal(s) associated with measured changes in light absorption of oxygenated and/or deoxygenated hemoglobin from the patient at location 108*a*, and the second biophysical-signal data set 110*b* comprises a set of raw cardiac or biopotential signal(s) associated with electrical signals of the heart. Though in FIG. 1, raw photoplethysmographic or hemodynamic signal(s) are shown being acquired at a patient's finger, the signals may be alternatively acquired at the patient's toe, wrist, forehead, earlobe, neck, etc. Similarly, although the cardiac or biopotential signal(s) are shown to be acquired via three sets of orthogonal leads, other lead configurations may be used (e.g., 11 lead configuration, 12 lead configuration, etc.).

Plots 110*a*' and 110*b*' show examples of the first biophysical-signal data set 110*a* and the second biophysical-signal data set 110*a*, respectively. Specifically, Plot 110*a*' shows an example of an acquired photoplethysmographic or hemodynamic signal. In Plot 110*a*', the photoplethysmographic signal is a time series signal having a signal voltage potential as a function of time as acquired from two light sources (e.g., infrared and red-light sources). Plot 110*b*' shows an example cardiac signal comprising a 3-channel potential time series plot. In some embodiments, the biophysical signal capture system 102 preferably acquires biophysical signals via non-invasive means or component(s). In alternative embodiments, invasive or minimally-invasively means or component(s) may be used to supplement or as substitutes for the non-invasive means (e.g., implanted pressure sensors, chemical sensors, accelerometers, and the like). In still further alternative embodiments, non-invasive and non-contact probes or sensors capable of collecting biophysical signals may be used to supplement or as substitutes for the non-invasive and/or invasive/minimally invasive means, in any combination (e.g., passive thermometers, scanners, cameras, x-ray, magnetic, or other means of non-contact or contact energy data collection system as discussed herein). Subsequent to signal acquisitions and recording, the biophysical signal capture system 102 then provides, e.g., sending over a wireless or wired communication system and/or a network, the acquired biophysical-signal data set 110 (or a data set derived or processed therefrom, e.g., filtered or pre-processed data) to a data repository 112 (e.g., a cloud-based storage area network) of the assessment system 103. In some embodiments, the acquired biophysical-signal data set 110 is sent directly to the assessment system 103 for analysis or is uploaded to a data repository 112 through a secure clinician's portal.

Biophysical signal capture system 102 is configured with circuitries and computing hardware, software, firmware, middleware, etc., in some embodiments, to acquire, store, transmit, and optionally process both the captured biophysical signals to generate the biophysical-signal data set 110. An example biophysical signal capture system 102 and the acquired biophysical-signal set data 110 are described in U.S. Pat. No. 10,542,898, entitled "Method and Apparatus for Wide-Band Phase Gradient Signal Acquisition," or U.S. Patent Publication No. 2018/0249960, entitled "Method and Apparatus for Wide-Band Phase Gradient Signal Acquisition," each of which is hereby incorporated by reference herein in its entirety.

In some embodiments, biophysical signal capture system 102 includes two or more signal acquisition components, including a first signal acquisition component (not shown) to acquire the first biophysical signals (e.g., photoplethysmographic signals) and includes a second signal acquisition component (not shown) to acquire the second biophysical signals (e.g., cardiac signals). In some embodiments, the electrical signals are acquired at a multi-kilohertz rate for a few minutes, e.g., between 1 kHz and 10 kHz. In other embodiments, the electrical signals are acquired between 10 kHz and 100 kHz. The hemodynamic signals may be acquired, e.g., between 100 Hz and 1 kHz.

Biophysical signal capture system 102 may include one or more other signal acquisition components (e.g., sensors such as mechano-acoustic, ballistographic, ballistocardiographic, etc.) for acquiring signals. In other embodiments of the signal capture system 102, a signal acquisition component comprises conventional electrocardiogram (ECG/EKG) equipment (e.g., Holter device, 12 lead ECG, etc.).

Assessment system 103 comprises, in some embodiments, the data repository 112 and an analytical engine or analyzer (not shown—see FIGS. 15A and 15B). Assessment system 103 may include feature modules 114 and a classifier module 116 (e.g., an ML classifier module). In FIG. 1, Assessment system 103 is configured to retrieve the acquired biophysical signal data set 110, e.g., from the data repository 112, and use it in the feature modules 114, which is shown in FIG. 1 to include a visual feature module 120 and other modules 122 (later described herein). The features modules 114 compute values of features or parameters, including those of visual features to provide to the classifier module 116, which computes an output 118, e.g., an output score, of the metrics associated with the physiological state of a patient (e.g., an indication of the presence or non-presence of a disease state, medical condition, or an indication of either). Output 118 is subsequently presented, in some embodiments, at a healthcare physician portal (not shown—see FIGS. 15A and 15B) to be used by healthcare professionals for the diagnosis and treatment of pathology or a medical condition. In some embodiments, a portal may be configured (e.g., tailored) for access by, e.g., patients, caregivers, researchers, etc., with output 118 configured for the portal's intended audience. Other data and information may also be a part of output 118 (e.g., the acquired biophysical signals or other patient's information and medical history).

Classifier module 116 (e.g., ML classifier module) may include transfer functions, look-up tables, models, or operators developed based on algorithms such as but not limited to decision trees, random forests, neural networks, linear models, Gaussian processes, nearest neighbor, SVMs, Naive Bayes, etc. In some embodiments, classifier module 116 may include models that are developed based on ML techniques described in U.S. Provisional Patent Application No. 63/235,960, filed Aug. 23, 2021, entitled "Method and System to Non-Invasively Assess Elevated Left Ventricular End-Diastolic Pressure"; U.S. Patent Publication No. 20190026430, entitled "Discovering Novel Features to Use in Machine Learning Techniques, such as Machine Learning Techniques for Diagnosing Medical Conditions"; or U.S. Patent Publication No. 20190026431, entitled "Discovering Genomes to Use in Machine Learning Techniques," each of which is hereby incorporated by reference herein in its entirety.

Example Biophysical Signal Acquisition.

Figure 2:
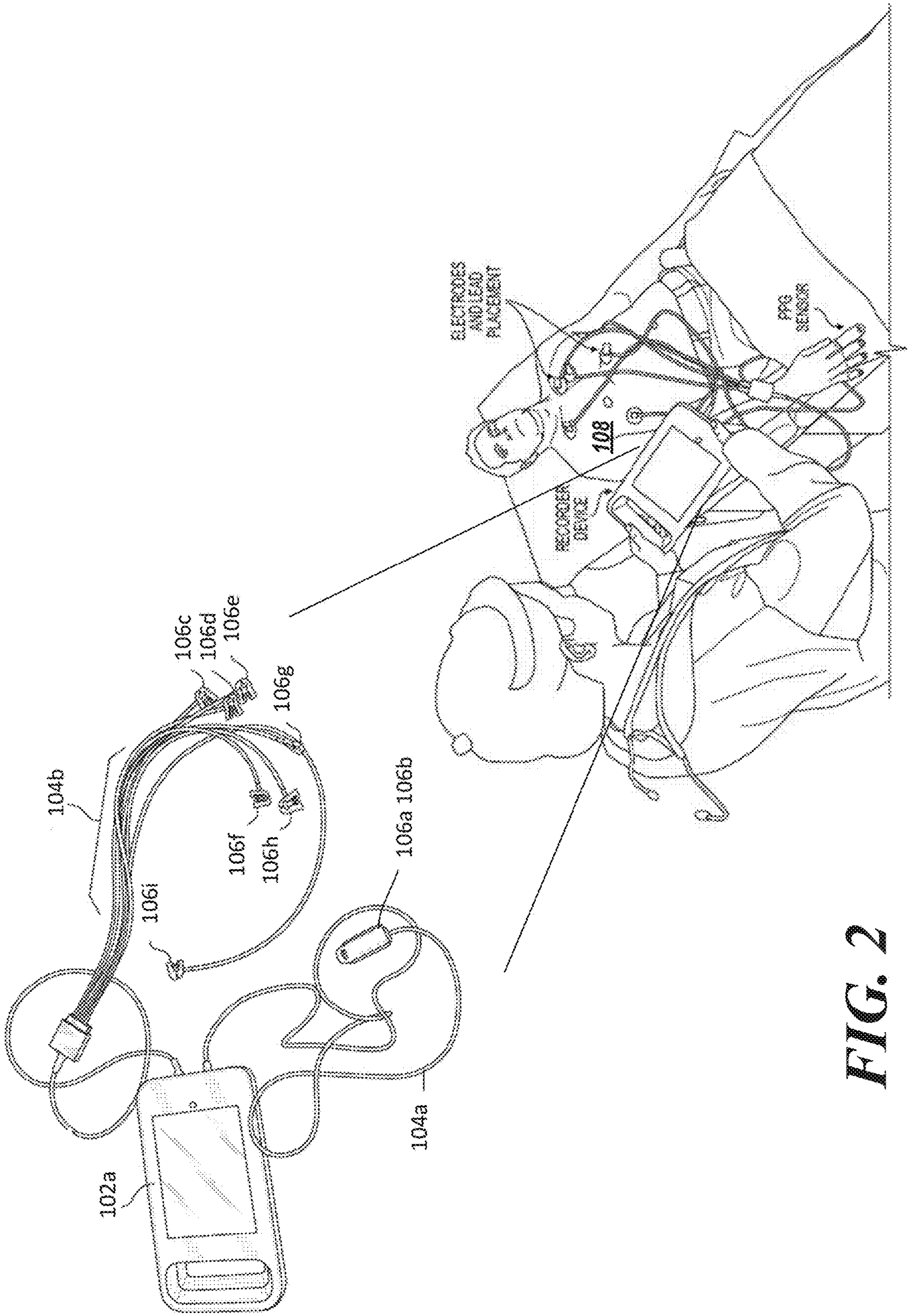
FIG. 2 shows an example biophysical signal capture system or component and its use in non-invasively collecting biophysical signals of a patient in a clinical setting in accordance with an illustrative embodiment.

FIG. 2 shows a biophysical signal capture system 102 (shown as 102*a*) and its use in non-invasively collecting biophysical signals of a patient in a clinical setting in accordance with an illustrative embodiment. In FIG. 2, the biophysical signal capture system 102*a* is configured to capture two types of biophysical signals from the patient 108 while the patient is at rest. The biophysical signal capture system 102*a* synchronously acquires the patient's (i) electrical signals (e.g., cardiac signals corresponding to the second biophysical-signal data set 110*b*) from the torso using orthogonally placed sensors (106*c*-106*h*; 106*i* is a $7^{th}$ common-mode reference lead) and (ii) hemodynamic signals (e.g., PPG signals corresponding to the first biophysical-signal data set 110*a*) from the finger using a photoplethysmographic sensor (e.g., collecting signals 106*a*, 106*b*).

As shown in FIG. 2, the electrical and hemodynamic signals (e.g., 104*a*, 104*b*) are passively collected via commercially available sensors applied to the patient's skin. The signals may be acquired beneficially without patient exposure to ionizing radiation or radiological contrast agents and without patient exercise or the use of pharmacologic stressors. The biophysical signal capture system 102*a* can be used in any setting conducive for a healthcare professional, such as a technician or nurse, to acquire the requisite data and where a cellular signal or Wi-Fi connection can be established.

The electrical signals (e.g., corresponding to the second biophysical signal data set 110*b*) are collected using three orthogonally paired surface electrodes arranged across the patient's chest and back along with a reference lead. The electrical signals are acquired, in some embodiments, using a low-pass anti-aliasing filter (e.g., ~2 kHz) at a multi-kilohertz rate (e.g., 8 thousand samples per second for each of the six channels) for a few minutes (e.g., 215 seconds). In alternative embodiments, the biophysical signals may be continuously/intermittently acquired for monitoring, and portions of the acquired signals are used for analysis. The hemodynamic signals (e.g., corresponding to the first biophysical signal data set 110*a*) are collected using a photoplethysmographic sensor placed on a finger. The photoabsorption of red light (e.g., any wavelengths between 600-750 nm) and infrared light (e.g., any wavelengths between 850-950 nm) are recorded, in some embodiments, at a rate of 500 samples per second over the same period. The biophysical signal capture system 102*a* may include a common mode drive that reduces common-mode environmental noise in the signal. The photoplethysmographic and cardiac signals were simultaneously acquired for each patient. Jitter (inter-modality jitter) in the data may be less than about 10 microseconds (μs). Jitter among the cardiac signal channels may be less than 10 microseconds, e.g., around ten femtoseconds (fs).

A signal data package containing the patient metadata and signal data may be compiled at the completion of the signal acquisition procedure. This data package may be encrypted before the biophysical signal capture system 102*a* transfers the package to the data repository 112. In some embodiments, the data package is transferred to the assessment system (e.g., 103). The transfer is initiated, in some embodiments, following the completion of the signal acquisition procedure without any user intervention. The data repository 112 is hosted, in some embodiments, on a cloud storage service that can provide secure, redundant, cloud-based storage for the patient's data packages, e.g., Amazon Simple Storage Service (i.e., "Amazon S3"). The biophysical signal capture system 102*a* also provides an interface for the practitioner to receive notification of an improper signal acquisition to alert the practitioner to immediately acquire additional data from the patient.

Example Method of Operation

Figure 3A:
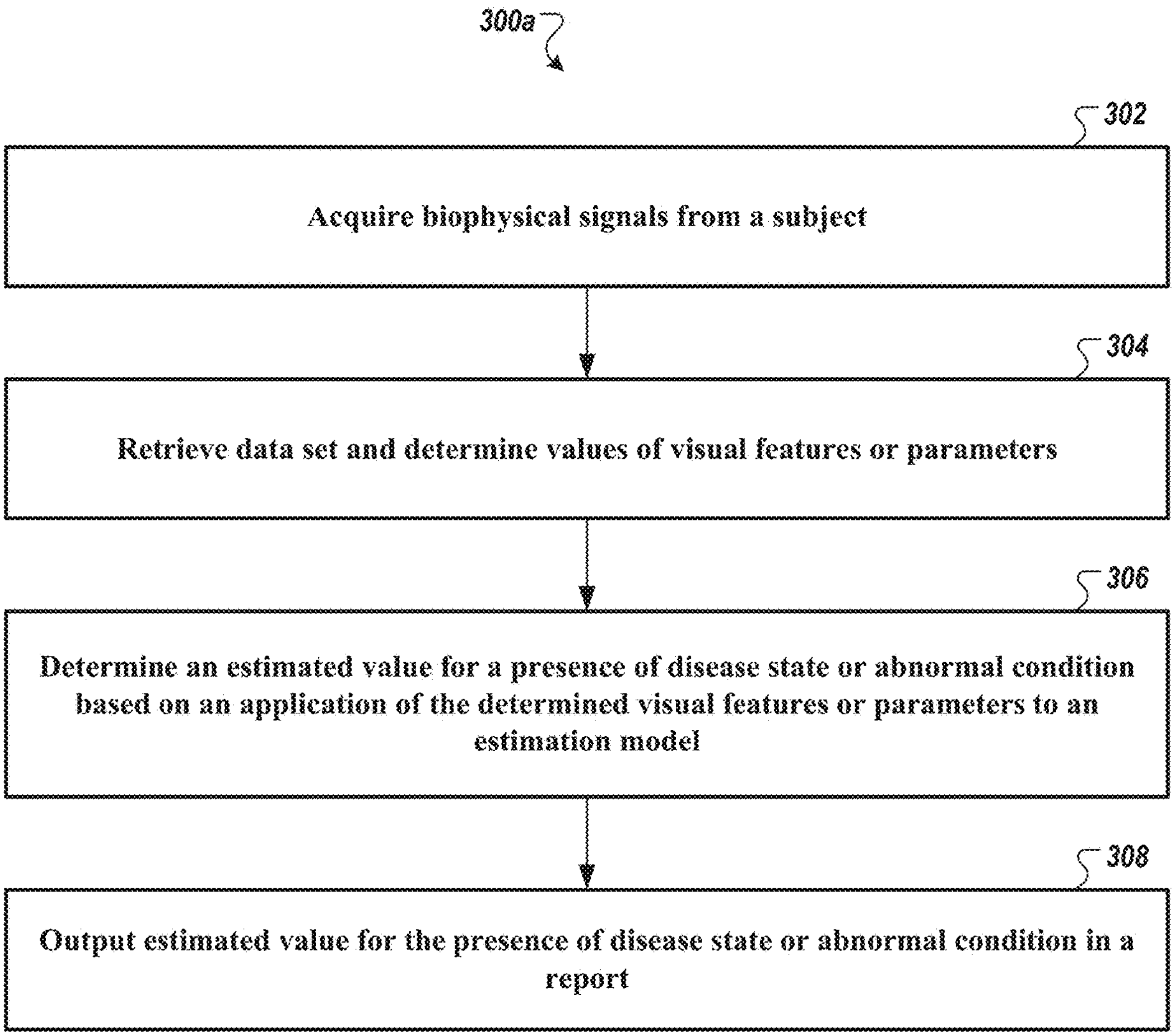
FIGS. 3A-3B each shows an example method to use visual features/parameters or their intermediate data in a practical application for diagnostics, treatment, monitoring, or tracking.
Figure 3B:
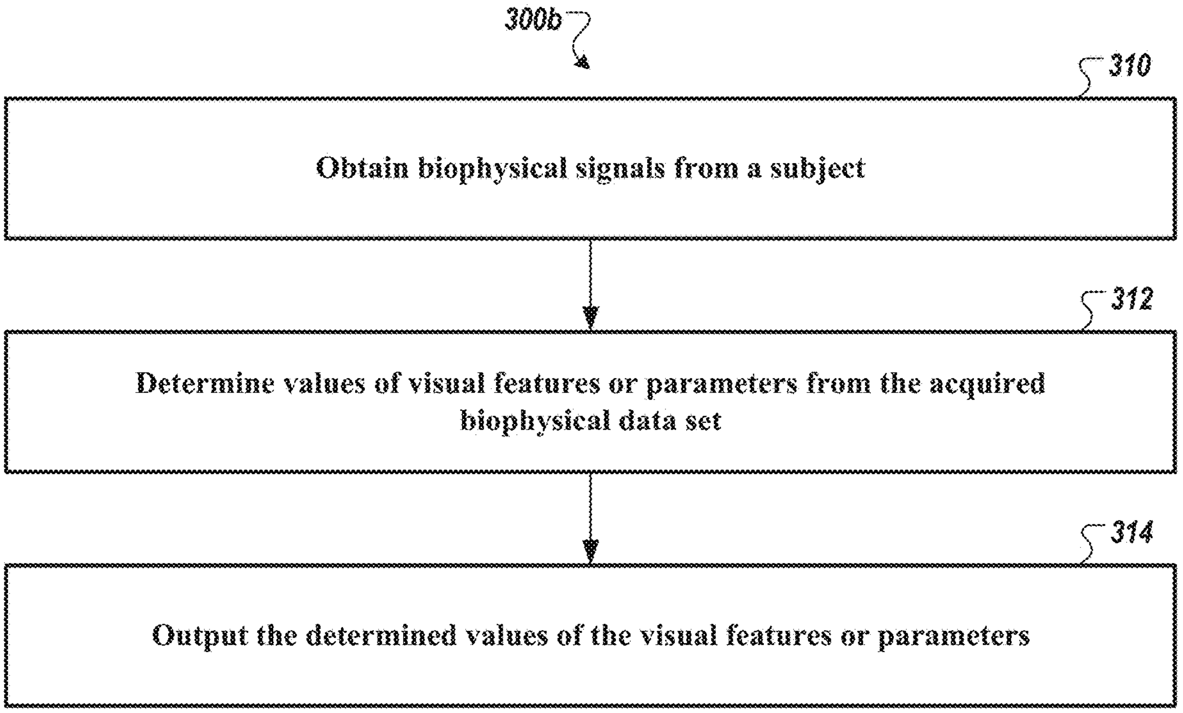

FIGS. 3A-3B each shows an example method to use visual features or their intermediate outputs in a practical application for diagnostics, treatment, monitoring, or tracking.

Estimation of Presence of Disease State or Indicating Condition. FIG. 3A shows a method 300*a* that employs visual parameters or features to determine estimators of the presence of a disease state, medical condition, or indication of either, e.g., to aid in the diagnosis, tracking, or treatment. Method 300*a* includes the step of acquiring (302) biophysical signals from a patient (e.g., cardiac signals, photoplethysmographic signals, ballistocardiographic signals), e.g., as described in relation to FIGS. 1 and 2 and other examples as described herein. In some embodiments, the acquired biophysical signals are transmitted for remote storage and analysis. In other embodiments, the acquired biophysical signals are stored and analyzed locally.

As stated above, one example in the cardiac context is the estimation of the presence of abnormal left-ventricular end-diastolic pressure (LVEDP) or mean pulmonary artery pressure (mPAP), significant coronary artery disease (CAD), abnormal left ventricular ejection fraction (LVEF), and one or more forms of pulmonary hypertension (PH), such as pulmonary arterial hypertension (PAH). Other pathologies or indicating conditions that may be estimated include, e.g., one or more forms of heart failure such as, e.g., heart failure with preserved ejection fraction (HFpEF), arrhythmia, congestive heart failure, valve failure, among various other diseases and medical conditions disclosed herein.

Method 300*a* further includes the step of retrieving (304) the data set and determining values of visual features. Example operations to determine the values of visual features are provided in relation to FIGS. 4-11 later discussed herein. Method 300*a* further includes the step of determining (306) an estimated value for a presence of a disease state, medical condition, or an indication of either based on an application of the determined visual features to an estimation model (e.g., ML models). An example implementation is provided in relation to FIGS. 15A and 15B.

Method 300*a* further includes the step of outputting (308) estimated value(s) for the presence of disease state or abnormal condition in a report (e.g., to be used diagnosis or treatment of the disease state, medical condition, or indication of either), e.g., as described in relation to FIGS. 1, 15A, and 15B and other examples described herein.

Diagnostics or Condition Monitoring or Tracking. FIG. 3B shows a method 300*b* that employs visual parameters or features for the monitoring health or controls of medical equipment or health monitoring device. Method 300*b* includes the step of obtaining (302) biophysical signals from a patient (e.g., cardiac signals, photoplethysmographic signals, ballistocardiographic signals, etc.). The operation may be performed continuously or intermittently, e.g., to provide output for a report or as controls for the medical equipment or the health monitoring device.

Method 300*b* further includes determining (310) visual feature value(s) from the acquired biophysical data set, e.g., as described in relation to FIGS. 4-11.

Method 300*b* further includes outputting (312) value(s) of the visual features or parameters (e.g., in a report for use in diagnostics or as signals for controls). For monitoring and tracking, the output may be via a wearable device, a hand-held device, or medical diagnostic equipment (e.g., pulse oximeter system, wearable health monitoring systems) to provide augmented data associated with health. In some embodiments, the outputs may be used in resuscitation systems, cardiac or pulmonary stress test equipment, and pacemakers.

Visual Predictor Features

Figure 4:
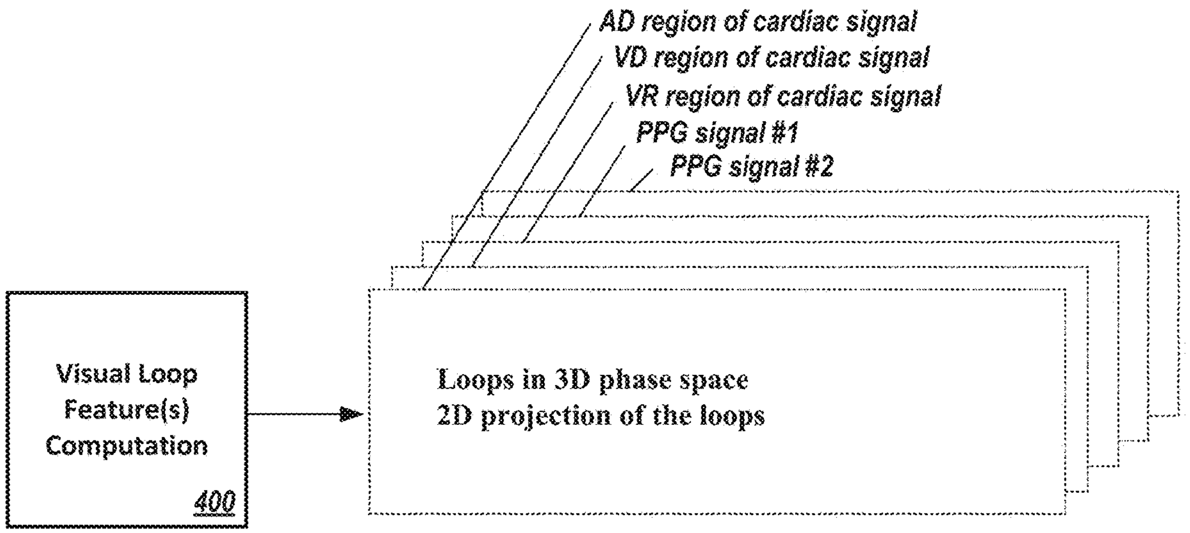
FIG. 4 illustrates an example visual loop feature computation module in accordance with an illustrative embodiment.
Figure 5:
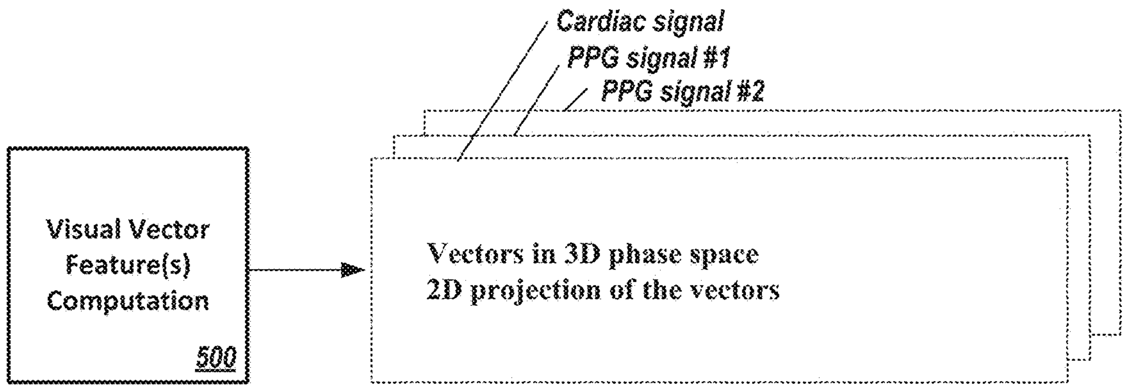
FIG. 5 illustrates an example visual vector feature computation module in accordance with an illustrative embodiment.

FIGS. 4 and 5 each shows an example visual feature assessment module, for a total of two example modules, configured to determine values of one or more visual-predictor associated properties in accordance with an illustrative embodiment. In particular, the visual loop features assessment module 400 of FIG. 4 can compute values of visual loop features and features generated from their orthogonal projections, for (i) waveform regions of interest in the cardiac signals (shown as atrial depolarization (AD) waveform regions, ventricular repolarization (VR) waveform regions, ventricular depolarization (VR) waveform regions) and (ii) PPG signals (shown as PPG signals #1 and #2), each expressed in a phase space model, to assess morphologies and variability of waveform regions under study. Loop features can include features associated with the perimeter, the surface area, the volume, the curvature, and the vorticity, of a point cloud model or a solid model generated from the point cloud for each of the waveforms of interest. For cardiac signals, these can include specific waveform regions such as AD, VD, and VR waveform regions, and, for PPG signals, these can include the whole signal.

Visual vector features assessment module 500 of FIG. 5 can compute values of visual vector features and features generated from their orthogonal projections, for (i) waveform regions of interests in the cardiac signals (shown as AD, VD, and VR waveform regions) and (ii) PPG signals (shown as PPG signals #1 and #2), each expressed in a phase space model, to assess morphologies and variability of waveform regions under study. For cardiac signals, these can include specific waveform regions such as AD, VD, and VR waveform regions, and, for PPG signals, these can include the whole signal.

Example #1—Visual Loop Features

FIG. 4 illustrates, as the first of two example visual feature categories, an example visual loop feature assessment module 400 configured to determine output values of visual features or parameters that characterize visual properties such a perimeter, surface area, volume, curvature, and/or vorticity, of a point cloud, or a solid model generated from the point cloud, generated from a waveform of interest. Additional features may be determined for 2D projections or quadrants of the solid model. For cardiac signals, visual properties can be calculated of specific waveform regions, as the waveform of interest, such as atrial depolarization (AD) waveform regions, ventricular repolarization (VR) waveform regions, ventricular depolarization (VD) waveform regions. For PPG signals, visual properties can be calculated for an acquired waveform. A point cloud, or solid model, can be generated from data points in three channels of (i) an acquired cardiac signal or (ii) a PPG signal and an associated VPG and APG signal generated from that PPG signal.

Table 2 shows an example set of 12 extracted visual loop features that can be extracted from a biophysical signal or a waveform region therein. In an embodiment, the 12 visual features can be determined for, some or all of, the 3 waveform regions of a cardiac or biopotential signal and for 2 PPG signals to provide up to a total of 75 features. In Table 2, features designated with the symbol "*" have been experimentally determined to have significant utility in the assessment of the presence or non-presence of at least one cardiac disease, medical condition, or an indication of either such as the determination of presence or non-presence of elevated LVEDP. In Table 2, features designated with the symbol "**" have been experimentally determined to have significant utility in the assessment of the presence or non-presence of at least one cardiac disease, medical condition, or an indication of either such as the determination of presence or non-presence of coronary artery disease. The list of the specific features determined to have significant utility in the assessment of the presence or non-presence of abnormal or elevated LVEDP and the presence or non-presence of significant CAD is provided in Tables 10A and 10B and and Tables 11A and 11B, respectively.

TABLE 2

| Feature Name | Feature Description |
|---|---|
| 3dPerimeter_Overall* | Mode of the sum of Euclidian distances of consecutive paired points for each cycle |
| SurfArea_AlphaShape_Overall* (also referred to as "SurfaceArea_AlphaShape_Overall") | Surface area of alpha shape encapsulating a point cloud of data for a cardiac segment or PPG signal. |
| SurfArea_ConvHull_Overall (also referred to as "Surface_ConvexHull") | Surface area of Convex Hull encapsulating a point cloud of data for a cardiac segment or PPG signal. |
| Volume_AlphaShape_Overall* | Volume of alpha shape encapsulating a point cloud of data for a cardiac segment or PPG signal. |

TABLE 2-continued

| Feature Name | Feature Description |
|---|---|
| Volume_ConvHull_Overall*, ** (also referred to as "Volume_ConvexHull") | Volume of Convex Hull encapsulating a point cloud of data for a cardiac segment or PPG signal. |
| maxFitPlanarArea | Area of maximum fit plane encapsulating a point cloud of data for a cardiac segment or PPG signal |
| 3dMeanCurvature*, ** | Median curvature of a cardiac segment or PPG signal in which curvature is defined as an inverse of the radius of a circle determined preceding a registration point in the cardiac segment or PPG signal. |
| 3dMaxCurvature* | Maximum curvature of a cardiac segment or PPG signal in which curvature is defined as an inverse of the radius of a circle determined preceding a registration point in the cardiac segment or PPG signal. |
| Average Vorticity*, ** (also referred to as "AverageVorticity") | Local measure of rotation of the points comprising the loop in phase space. It is determined as a curl of a vector joining the points to the origin. |
| Circulation*, ** | Global measure of rotation of the points comprising the loop in phase space. |
| MaximumVelocity (of Propagation)** (also referred to as "MaxVelocity") | Maximum Euclidean distance between any two consecutive points of the cardiac segment or PPG loop divided by the time difference between the sampling of the two points. |
| Average Velocity (of Propagation)*, ** | Average Euclidean distance between any two consecutive points of the cardiac segment or PPG loop divided by the time difference between the sampling of the two points. |

Table 3A shows an example set of additional 4 types of extracted visual loop features that can be extracted from a biophysical signal or a waveform region therein of surface area and volume loop features of Table 2. Rather than determining the features for the entire 3D phase space model as provided in the feature of Table 2, the features of Table 3A determine the features for subregions (referred to as octants) of the 3D phase space model. In an embodiment, the 4 visual features of Table 2 can be determined for 8 octant regions for, some or all of, the 3 waveform regions of a cardiac or biopotential signal and for 2 PPG signals to provide up to a total of 235 features. In Table 3A, features designated with the symbol "*" have been experimentally determined to have significant utility in the assessment of the presence or non-presence of at least one cardiac disease, medical condition, or an indication of either such as the determination of presence or non-presence of elevated LVEDP. The list of the specific features determined to have significant utility in the assessment of the presence or non-presence of abnormal or elevated LVEDP is provided in Tables 10A and 10B.

TABLE 3A

| Feature Name | Feature Description |
|---|---|
| SurfArea_AlphaShape_Octant[1 . . . 8]*, ** (also referred to as "SurfaceArea_AlphaShape") | Surface area (of points present in Octant n) of alpha shape encapsulating a point cloud of data for a cardiac segment or PPG signal. |
| SurfArea_ConvHull_Octant[1 . . . 8]* (also referred to as "SurfaceArea_ConvexHull") | Surface area (of points present in Octant n) of Convex Hull encapsulating a point cloud of data for a cardiac segment or PPG signal. |
| Volume_AlphaShape_Octant[1 . . . 8]*, ** | Volume (of points present in Octant n) of alpha shape encapsulating a point cloud of data for a cardiac segment or PPG signal. |
| Volume_ConvHull_Octant[1 . . . 8]*, ** (also referred to as "Volume_ConvexHull") | Volume (of points present in Octant n) of Convex Hull encapsulating a point cloud of data for a cardiac segment or PPG signal. |

Table 3B shows an example set of additional 8 types of extracted visual loop features that can be extracted from a biophysical signal or a waveform region therein based on a projection, or a quadrant analysis of such projections, of the features of Table 2, including perimeter, area, curvature, and circulation. Table 3B shows an additional feature eccentricity. In an embodiment, 3 projections can be determined for each of the 8 feature types of Table 3B in which for each projection, 5 features (overall value and their sub-divisions in 4 quadrants) can be assessed to provide up to a total of 135 features. In Table 3B, features designated with the symbol "*" have been experimentally determined to have significant utility in the assessment of the presence or non-presence of at least one cardiac disease, medical condition, or an indication of either such as the determination of presence or non-presence of elevated LVEDP. In Table 3B, features designated with the symbol "**" have been experimentally determined to have significant utility in the assessment of the presence or non-presence of at least one cardiac disease, medical condition, or an indication of either such as the determination of presence or non-presence of coronary artery disease. The list of the specific features determined to have significant utility in the assessment of the presence or non-presence of abnormal or elevated LVEDP and the presence or non-presence of significant CAD is provided in Tables 10A and 10B and Tables 11A and 11B, respectively.

TABLE 3B

| Feature Name | Feature Description |
|---|---|
| 2dPerimeter_Plane [XY, XZ, YZ]_Quadrant [Overall, 1 . . . 4]*, ** (also referred to as "2dPerimeter") | Mode of the sum of Euclidian distances of consecutive paired points for each cycle in quadrants or overall orthogonal projection of waveform regions of a cardiac signal or a PPG signal. |
| Max2dPerimeter_Plane [XY, XZ, YZ]* | Maximum sum value of Euclidian distances of consecutive paired points for a cycle of waveform regions of a cardiac signal or a PPG signal. |
| 2dArea_Plane [XY, XZ, YZ]_Quadrant [Overall, 1 . . . 4]*, ** | Area of the quadrant (4), or overall, in each of the three orthogonal projections of waveform regions of a cardiac signal or a PPG signal. |
| Max2dArea_Plane [XY, XZ, YZ]*, ** | Quadrant location having a maximum area among the three orthogonal projections of waveform regions of a cardiac signal or a PPG signal. |
| MeanCurvature_Plane [XY, XZ, YZ]** | Mean of curvatures calculated for each of the orthogonal projections of waveform regions of a cardiac signal or a PPG signal. |
| MaximumCurvature_Plane [XY, XZ, YZ] | Maximum curvature in each of the orthogonal projections of waveform regions of a cardiac signal or a PPG signal. |
| Eccentricity_Plane [XY, XZ, YZ]** | The extent of deviation of a loop in each orthogonal projection of waveform regions of a cardiac signal or a PPG signal. |
| Circulation_Plane [XY, XZ, YZ]*, ** | Mean of circulation calculated for each of the orthogonal projections of waveform regions of a cardiac signal or a PPG signal. |

Figure 6:
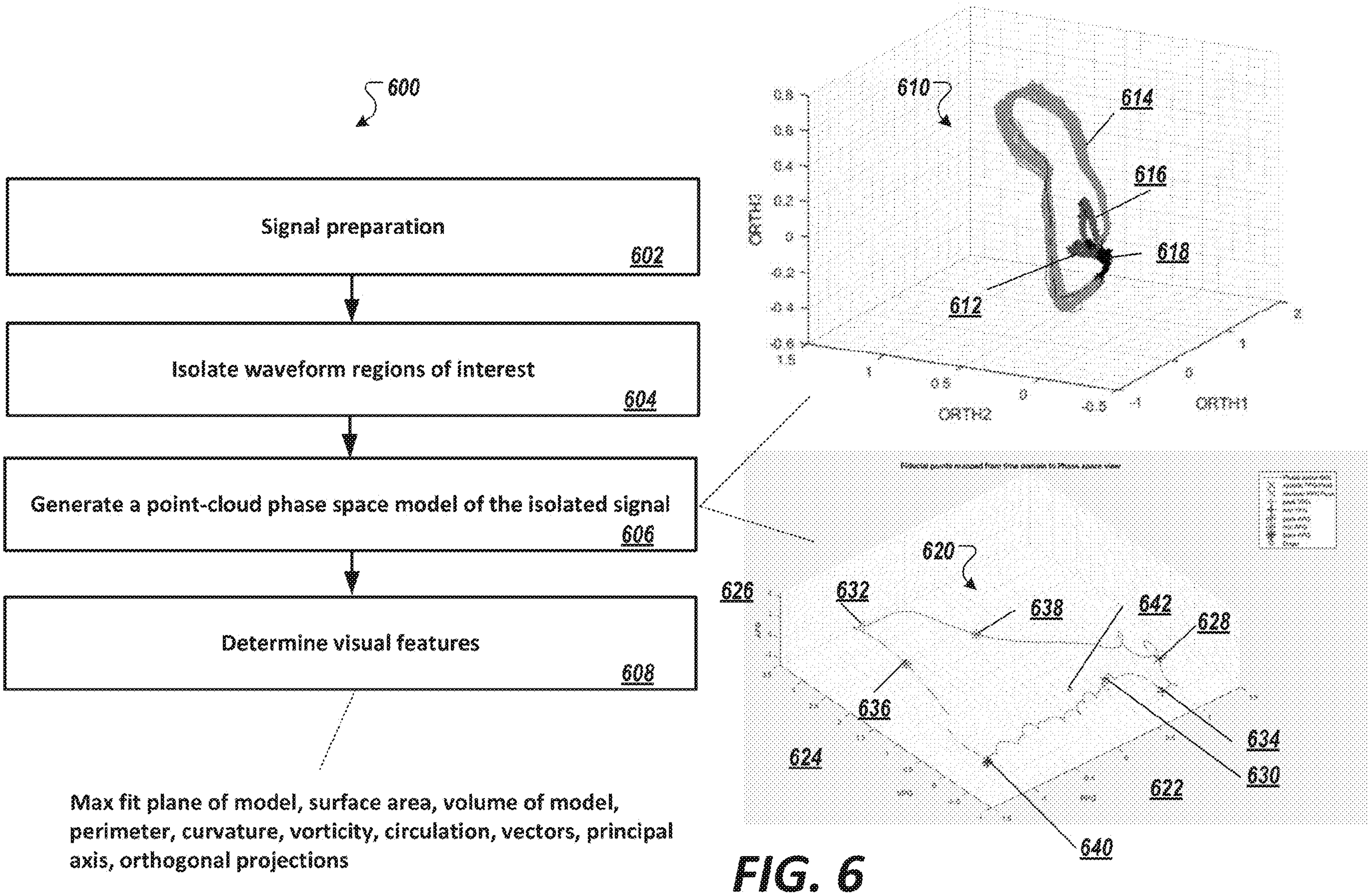
FIG. 6 shows an example method of operation of the visual loop or vector feature computation modules of FIG. 4 or 5 in accordance with an illustrative embodiment.

FIG. 6 shows an implementation (600) of the visual loop feature computation module 400 in accordance with an illustrative embodiment, which can be used wholly or partially to generate visual loop features or parameters, and their outputs to be used in a machine-learned classifier to determine a metric associated with a physiological system of a patient under study. To determine the example features of Table 2, Method 600, in some embodiments, includes (i) signal preparation (602), (ii) isolating (604) waveform regions of interest, (iii) generating (606) a point-cloud phase space model of the isolated signal, and (iv) determine visual features. FIG. 6 shows an example cardiac-signal phase space model 610 comprising multiple cardiac cycle data identified for three segment regions of interest, namely, the AD waveform regions 612, VD waveform regions 614, and VR waveform regions 616. The phase space model 610 also shows regions 618 not part of these three regions. FIG. 6 shows an example of PPG-signal phase space model 620 generated for a PPG signal 622 and its associated VPG signal 624 and APG signal 626. FIG. 6 also shows the PPG-signal phase space model 620 with fiducial points of interest, including a systolic PPG peak 628, a diastolic PPG peak 630, a peak VPG 632, a min VPG 634, a peak APG 636, a min APG 638, a base APG 640, and an origin 640. Additional descriptions are provided below.

Figure 7A:
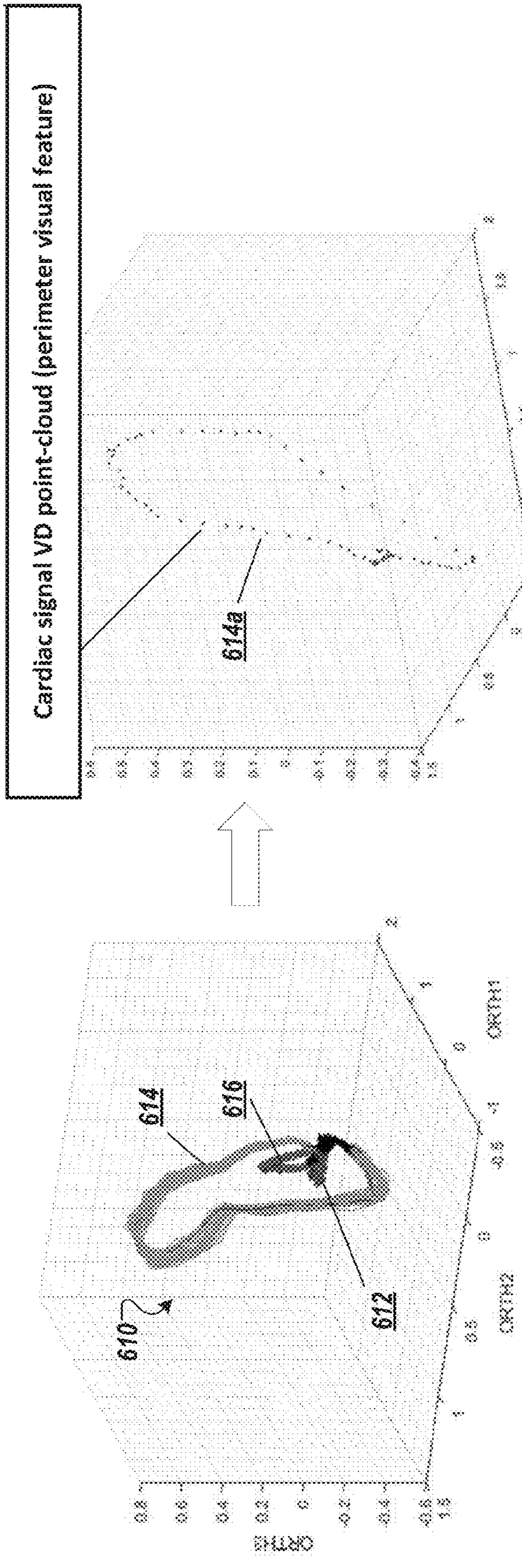
FIGS. 7A, 7B, 7C, 7D, 7E, 8A, 8B, 9A, and 9B each shows example operations performed by the visual feature loop computation module of FIG. 4 in accordance with an illustrative embodiment.
Figure 7B:
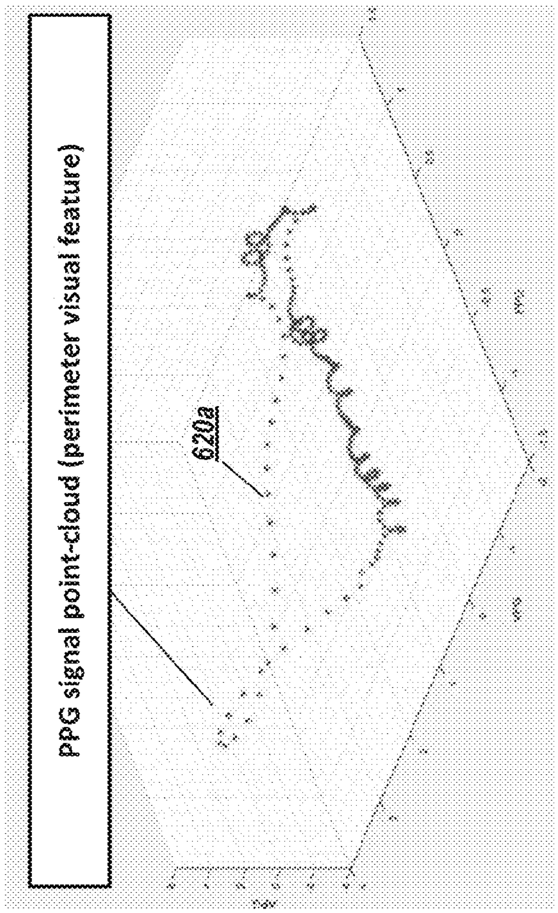

Perimeter Features. FIGS. 7A and 7B show example operations to compute perimeter features for cardiac and PPG signals. In the example shown in FIG. 7A, for cardiac signal data, Module 400 can generate a set of point cloud data in which each of the sets includes data for a single cardiac cycle and for a waveform region of interest, e.g., the AD waveform regions 612, VD waveform regions 614, and VR waveform regions 616 (in FIG. 7A, the example is shown for VD waveform regions 614 (shown as 614*a*) only). The perimeter value of a given waveform region can then be determined as the sum of Euclidean distances between each pair of consecutive points in the point cloud data of that waveform region. Because multiple cardiac cycles are acquired, Module 400 can determine the perimeter feature value for each cycle and then select the mode, mean, or median value of that set, e.g., up to 3 features, as shown and described in relation to Table 2. In the example features used for LVEDP assessment, the mode was used.

In the example shown in FIG. 7B, for a PPG signal, Module 400 can generate a set of point cloud data 620 (shown as 620*a*) each for a single PPG cycle. The perimeter value of a given waveform region can then be determined as the sum of Euclidean distances between each pair of consecutive points in that point cloud data to which the mode, mean, or median value of that set can be selected, e.g., up to an additional 2 features, as shown and described in relation to Table 2.

In addition, Module 400 can calculate the perimeter of a projection of the point cloud data 620 based on the 3 orthogonal planes (XY, XZ, and YZ). For cardiac signal phase space, the orthogonal planes can be expressed as channels X and Y, channels X and Z, and channels Y and Z (also referred to herein as the "ORTH12," "ORTH13," and/or "ORTH23" planes). For PPG signal phase space, the orthogonal planes can be expressed as PPG and VPG, PPG and APG, and VPG and APG (also referred to herein as the "PPG VPG," "PPG APG," and "PPG APG" planes).

Figure 7C:
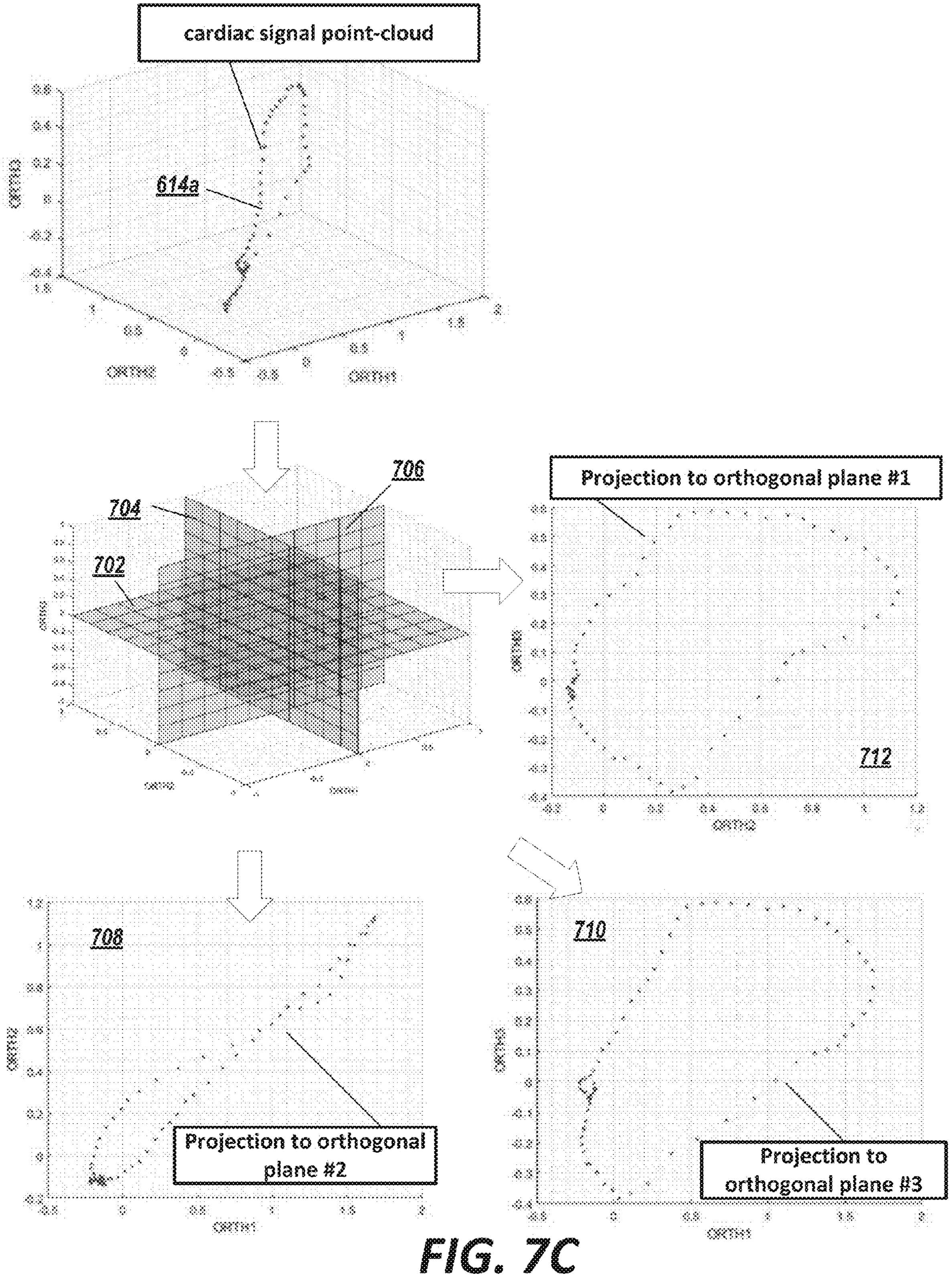
Figure 7D:
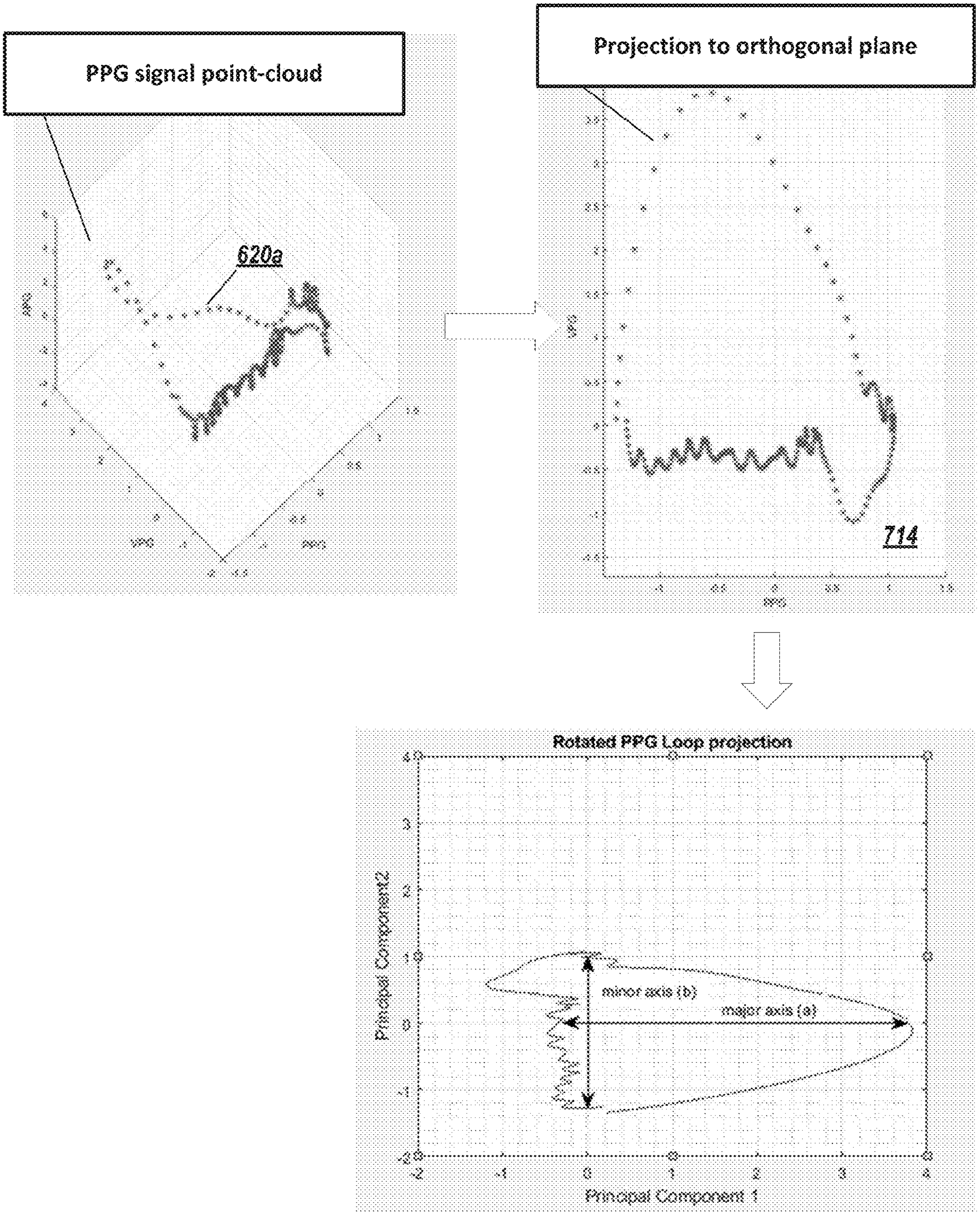

FIGS. 7C and 7D show example operations to cast a projection of point cloud data of a waveform region (e.g., VD waveform region, VR waveform region, AD waveform region) in the cardiac signal data or a PPG signal, onto the three orthogonal planes (ORTH12 (702), ORTH13 (704), and ORTH23 (706)). In the example shown in FIG. 7C, the three orthogonal projections ORTH12 (708), ORTH13 (710), and ORTH23 (712) are generated from a 3D phase space data of a VD waveform region (614*a*) (similar operations can be performed for the VR and AD waveform regions). In the example shown in FIG. 7D, an orthogonal projection, up to three, e.g., ORTH12 (708), ORTH13 (710), and ORTH23 (712), can be generated from a 3D phase space data of a PPG signal (similar operations can be performed for other PPG signals). Module 400 can determine, for each of the 3 orthogonal projections, the 2dperimeter feature value for each cycle of the 3 waveform regions of the cardiac signal data or the 2 PPG signal data and then select the mode, mean, or median value of that set, e.g., up to an additional 15 features, as described in relation to Table 3B.

Figure 7E:
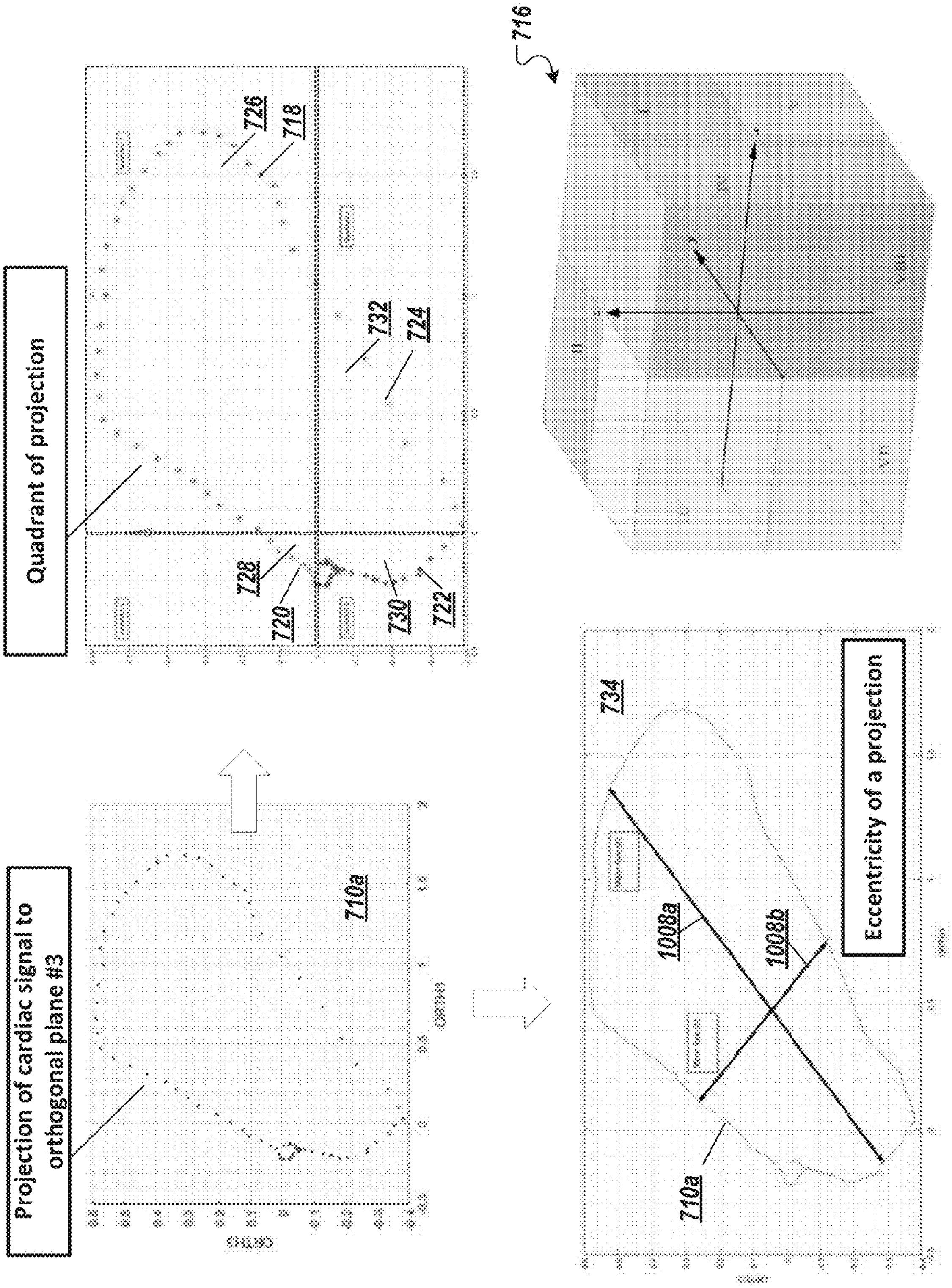

In addition, Module 400 can calculate the perimeter of specific quadrants of the 3 orthogonal plane projections. FIG. 7E shows example operations to segment the orthogonal projections of the waveform region (e.g., VD waveform region, VR waveform region, AD waveform region) in the cardiac signal data or a PPG signal, onto the quadrant regions 716 for each of the three orthogonal planes (quadrants [1 . . . 4] (see 716) of ORTH12 (702), quadrants [1 . . . 4] (see 716) of ORTH13 (704), and quadrants [1 . . . 4] (see 716) of ORTH23 (706)). In the example shown in FIG. 7E, an orthogonal projection of a VD waveform region 710 (shown as 710*a*) is shown divided into quadrants 718, 720, 722, and 724 (similar operations can be performed for each of the orthogonal projections of the VD waveform regions as well as for the VR and AD waveform regions and 2 PPG signals). Module 400 can thus determine, for each of the quadrants (4) of the 3 orthogonal projections, the 2dperimeter feature value for each cycle of the 3 waveform regions of the cardiac signal data or the 2 PPG signal data and then select the mode, mean, or median value of that set, e.g., up to an additional 60 features, as described in relation to Table 3B.

Figure 8A:
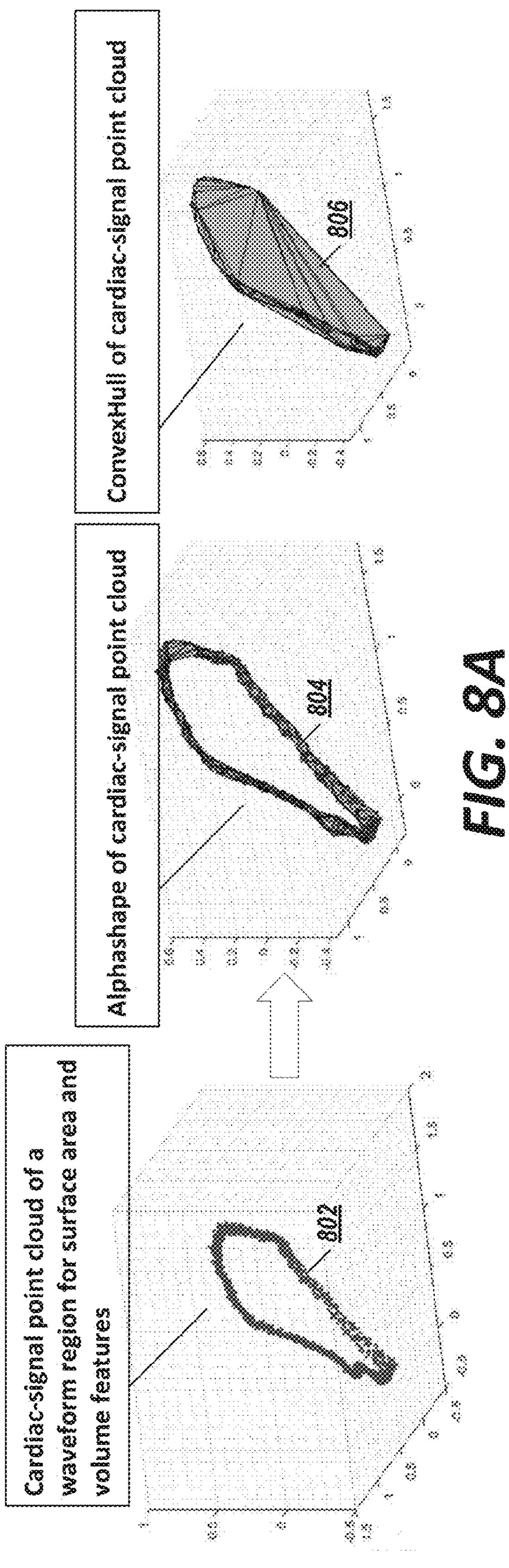
Figure 8B:
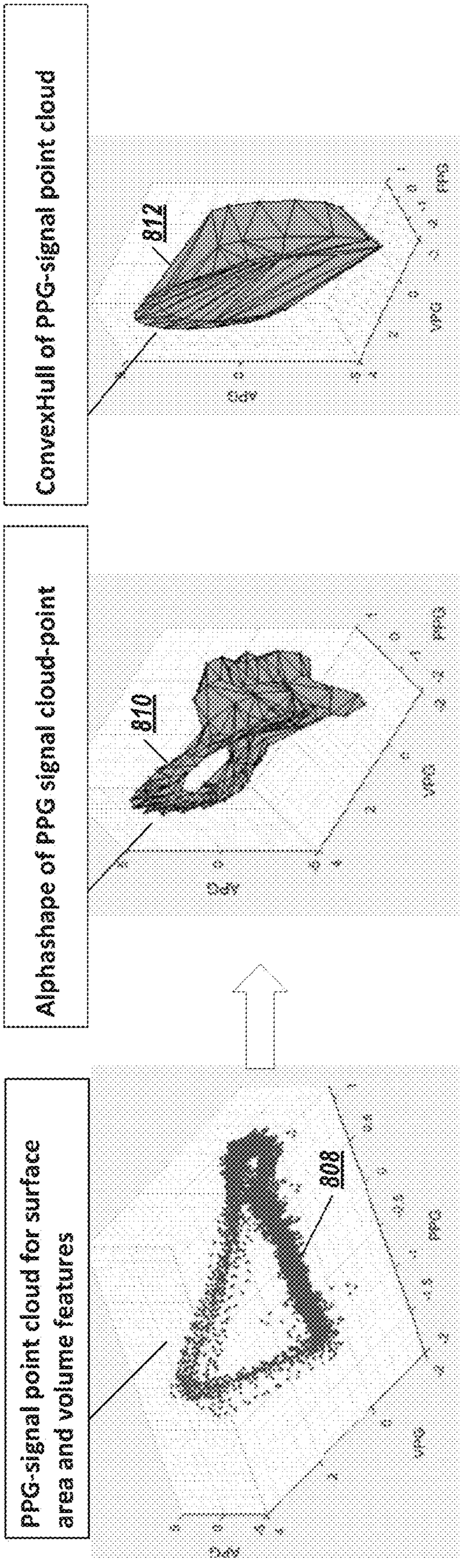

Surface Area, Volume, Area Projection Features. FIGS. 8A and 8B show example operations to compute surface area and volume features for cardiac and PPG signals. In the example shown in FIG. 8A, for cardiac signal data, Module 400 can generate (i) a point cloud data 802 for a waveform region of interest, e.g., the AD waveform regions 612, VD waveform regions 614, and VR waveform regions 616, over the multiple cardiac cycles (in FIG. 8A, the example is shown for VD waveform regions 614 only) and/or (ii) a point cloud data 808 for a signal, e.g., PPG signal #1 and PPG signal #2. Module 400 can then generate an alpha shape object (804, 810) or a convex hull object (806, 812) from the point cloud data (802, 808).

Cardiac loops and PPG signal loops are observed to have a distinct trajectory in three-dimensional space with the trajectory slightly varying beat-to-beat or cycle-to-cycle, e.g., due to intrinsic biological variations. Cardiac and PPG loops thus can create a region in phase space within which the datapoints are concentrated and form a three-dimensional loop. FIG. 8A shows VD loops 802 for a thirty-second window of signal data. Module 400 can wrap the loop data (e.g., 802) as an alpha shape object 804 (e.g., with the alpha radius being automatically set to the smallest value ensuring all points are covered) and as a convex hull object 806. FIG. 8B shows PPG loops 808 for an acquired PPG signal. Module 400 can wrap the loop data (e.g., 808) as an alpha shape object 810 (e.g., with the alpha radius being automatically set to the smallest value ensuring all points are covered) and as a convex hull object 812.

Module 400 can then calculate the surface area and volume of the 3D AlphaShape and ConvexHull shape as the feature values, e.g., up to 20 features for the 3 waveform regions of the cardiac signal data and the 2 PPG signal data, as shown and described in relation to Table 2.

Figure 10A:
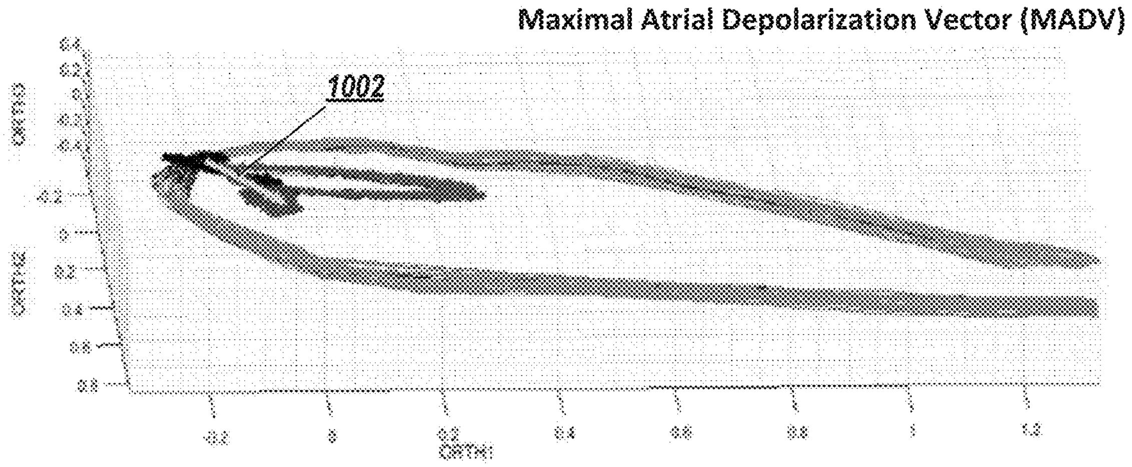
FIGS. 10A, 10B, 10C, 10D, 10E, 10F, 10G, 11A, and 11B each shows example operations performed by the visual vector computation module of FIG. 5 in accordance with an illustrative embodiment.
Figure 10B:
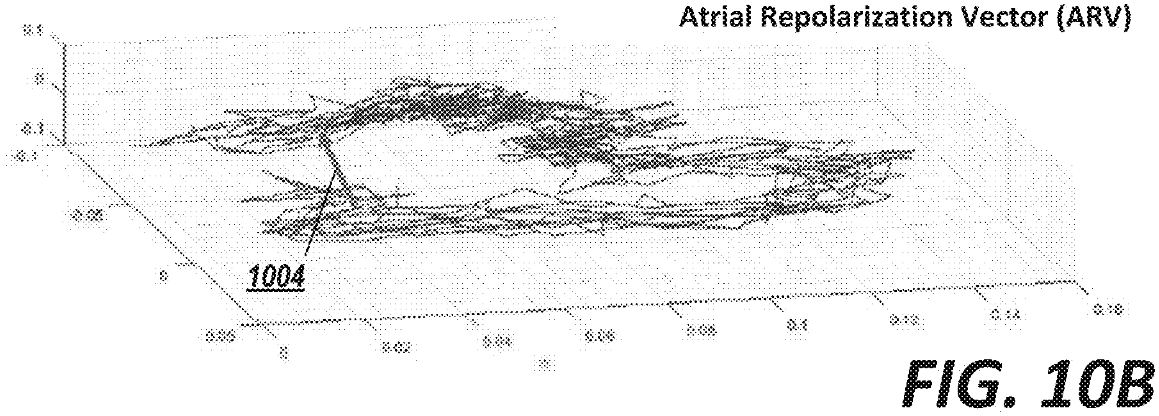
Figure 10C:
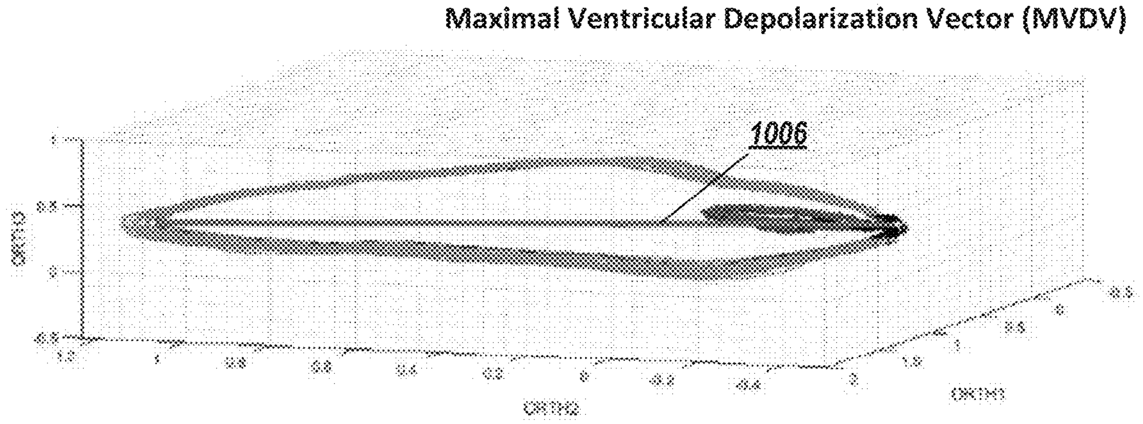
Figure 10D:
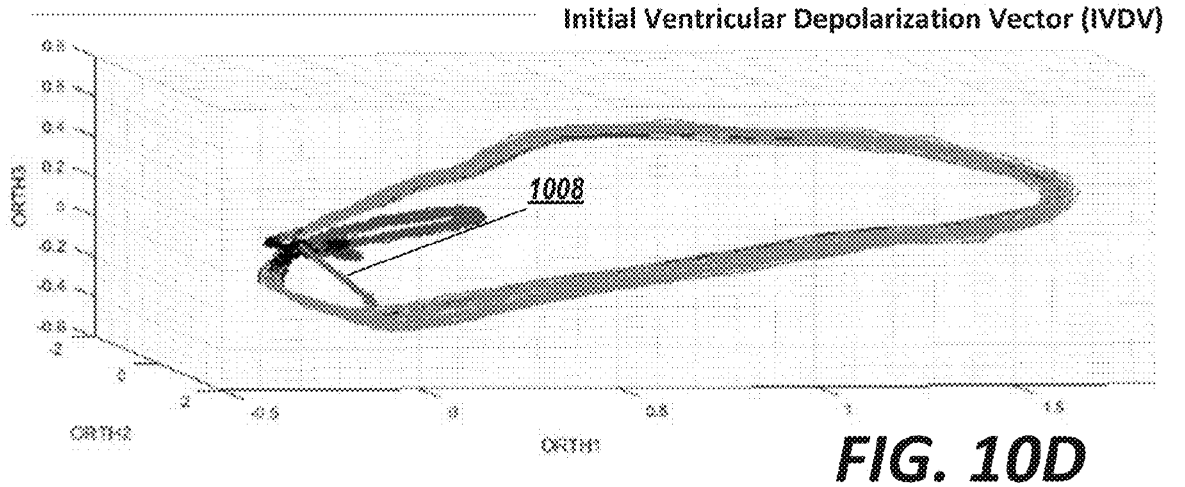
Figure 10E:
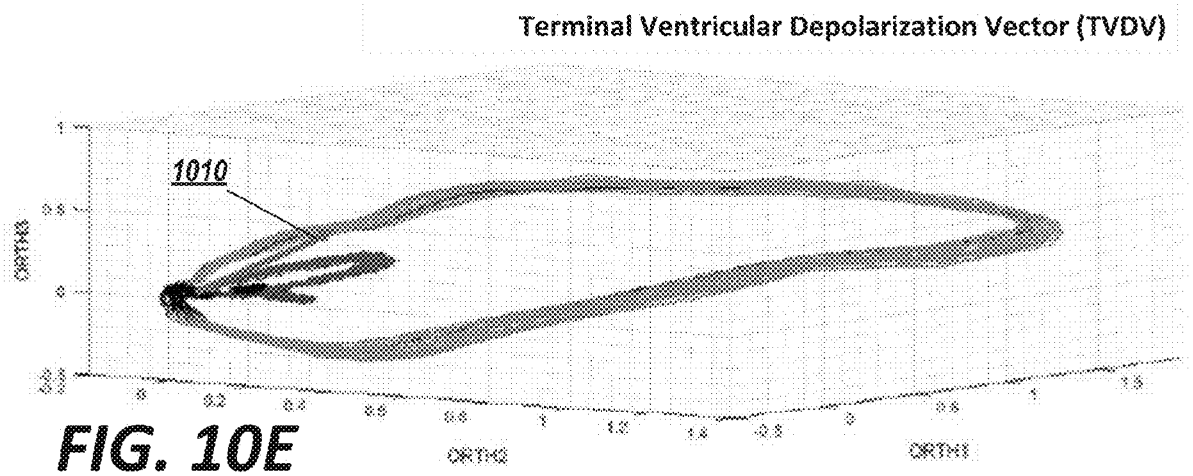
Figure 10F:
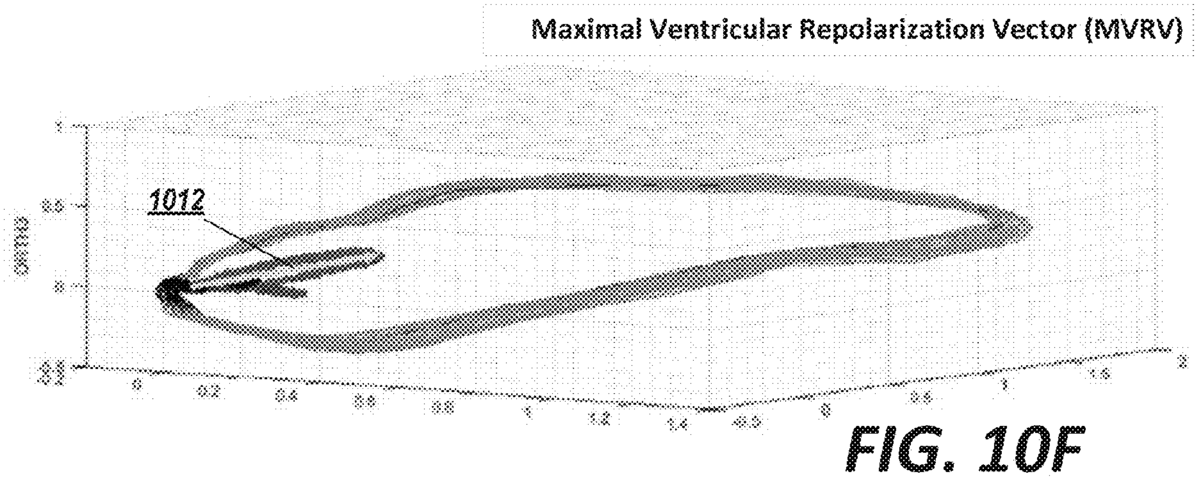

In addition, Module 400 can calculate the surface area and volume of the 3D AlphaShape and ConvexHull shape for each of the octant regions (e.g., 8 regions—see Table 4) as the feature values, e.g., up to an additional 160 features for the 3 waveform regions of cardiac signal data and the 2 PPG signal data, as shown and described in relation to Table 3A. An example layout of the octant regions is shown in FIG. 10B. Table 4 shows the octant identification regions.

TABLE 4

| Octant Number | Orth1 or PPG Sign | Orth2 or VPG Sign | Orth3 or APG Sign |
|---|---|---|---|
| Octant 1 | + | + | + |
| Octant 2 | − | + | + |
| Octant 3 | − | − | + |
| Octant 4 | + | − | + |
| Octant 5 | + | + | − |
| Octant 6 | − | + | − |
| Octant 7 | − | − | − |
| Octant 8 | + | − | − |

In addition, Module 400 can calculate the areas of quadrants (4) of the 3 orthogonal plane projections. In FIG. 7E, the areas 726, 728, 730, 732 of each quadrant of the orthogonal projections of the waveform region (e.g., VD waveform region, VR waveform region, AD waveform region), and the overall area of the quadrants, in the cardiac signal data or the 2 PPG signal data, can be determined, e.g., up to an additional 75 features, as described in relation to Table 3B. The area can be calculated using the TrapZ function or the like (e.g., manufactured by Matlab) in order to calculate the area within each quadrant. The overall area can be calculated using the polyarea Matlab function.

In addition, Module 400 can determine the particular quadrant among the 3 orthogonal projection data containing the maximum area to provide, e.g., up to an additional 15 features, as described in relation to Table 3B.

Figure 9A:
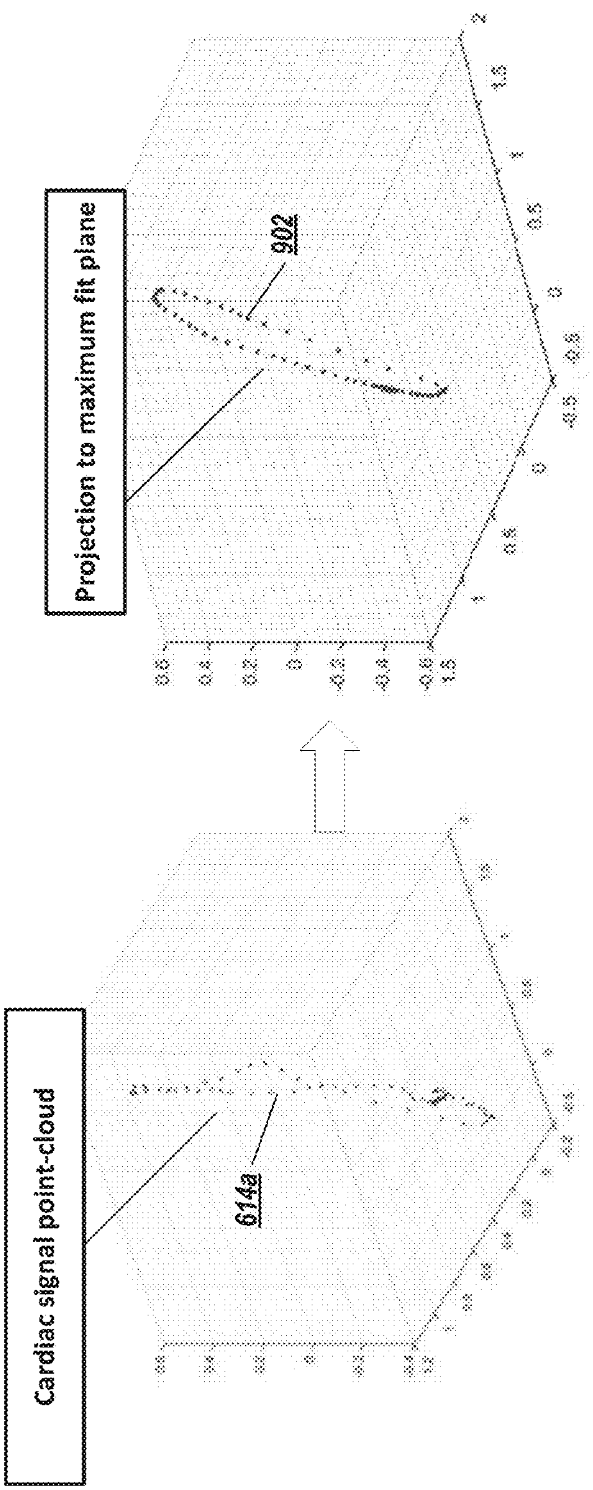
Figure 9B:
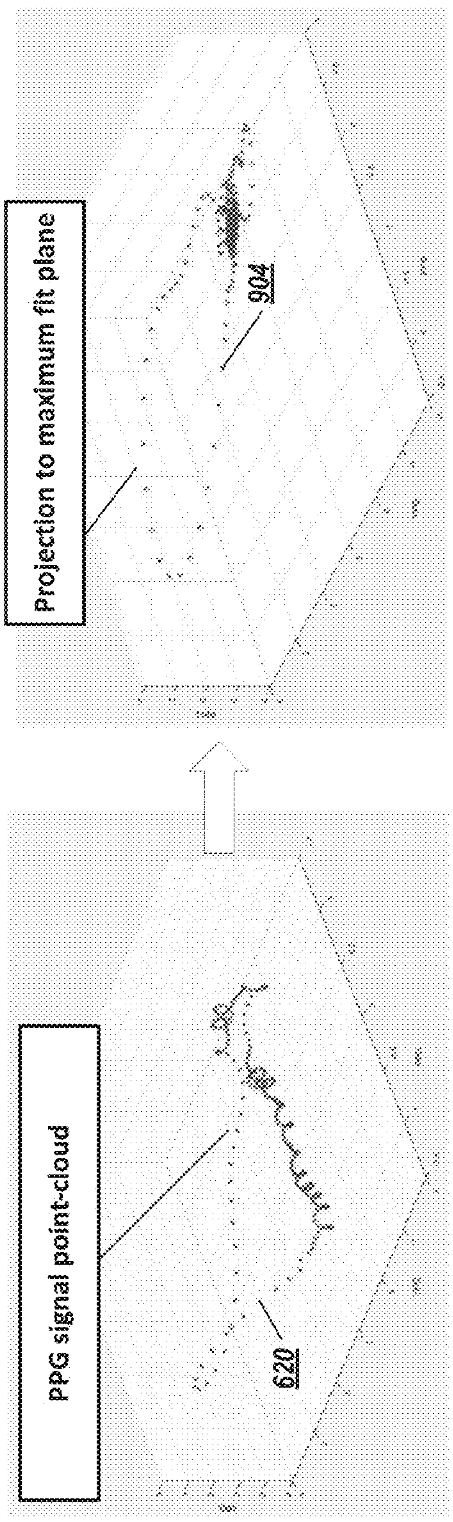

Maximum Fit Planar Area Features. FIGS. 9A and 9B show example operations to compute the maximum fit planar area features for cardiac and PPG signals. In the example shown in FIGS. 9A and 9B, Module 400 can generate (i) a maximum fit plane 902 of a waveform region of interest, e.g., the AD waveform regions 612, VD waveform regions 614, and VR waveform regions 616, over the multiple cardiac cycles (in FIG. 9A, the example is shown for a VD waveform region 614*a* only) and (ii) a maximum fit plane 904 of a signal, e.g., PPG signal #1 and PPG signal #2. For a given cardiac loop or PPG loop, the points encompassing the loop do not necessarily lie in a single 3D plane. The maximum fit plane is the best fitting plane through the points of a given cardiac or PPG loop. That is, the best fitting plane is the single plane where the loop has the least curvature or is the flattest. Module 400 can then project the points (902, 904) of the cardiac or PPG loop onto the best fitting plane, e.g., up to 5 features for the 3 waveform regions of a cardiac signal data and the 2 PPG signal data, as shown and described in relation to Table 2.

Curvature, Vorticity, Circulation, Velocity of Propagation, Eccentricity Features. The curvature of a single point in a loop, be it a cardiac loop or a PPG loop, can be defined as the inverse of the radius of a circle that passes through the specific point, a point which is 5 ms prior to the given point and a point which is 5 ms ahead of the given point. These three points, if not collinear, uniquely identify a circle.

Module 400 can calculate both the maximum curvature and the mean curvature, e.g., up to an additional 10 features for the 3 waveform regions of a cardiac signal data and the 2 PPG signal data, as shown and described in relation to Table 2.

In addition, the mean and maximum curvature of a 2D projection in 3 orthogonal planes can be determined, e.g., to provide up to an additional 30 features, for the 3 waveform regions of the cardiac signal data and the 2 PPG signal data.

Vorticity represents the rotation of the points comprising the loop in phase space. Module 400 can calculate vorticity, for each point in the loop, as the curl of the vector joining the point to the origin. The curl of that point can be represented as a vector, and the magnitude of the vector is representative of the magnitude of the rotation at that point in the loop. The curl at each point in the loop can be calculated per Equation 2.

$$\text{curl}(F) = \nabla \times F = \left(\frac{\partial F_z}{\partial y} - \frac{\partial F_y}{\partial z}\right)\hat{i} + \left(\frac{\partial F_z}{\partial z} - \frac{\partial F_z}{\partial x}\right)\hat{j} + \left(\frac{\partial F_y}{\partial x} - \frac{\partial F_x}{\partial y}\right)\hat{k} \quad \text{(Equation 2)}$$

In Equation 2, $F=F_x\hat{i}+F_y\hat{j}+F_z\hat{k}$ is the vector connecting the origin to the given point in the cardiac loop, and $\hat{i}$, $\hat{j}$, and $\hat{k}$ are the unit vectors for the ORTH1/PPG (x-axis), ORTH2/VPG (y-axis), and ORTH3/APG (z-axis), respectively, for a cardiac signal or PPG signal. Module 400 can calculate the average curl across all the points in the loop, e.g., up to 5 features for the 3 waveform regions of a cardiac signal data and the 2 PPG signal data, as shown and described in relation to Table 2.

Circulation is a macroscopic measure of the rotation of the points comprising the loop (whereas vorticity is a measure of local rotation of the points in the loop and calculated at each point in the loop). Put another way, circulation is a representation of the rotation of the loop as a whole. It may be calculated per Equation 3.

$$\text{Circulation} = \Gamma = \sum_{m=1}^{M-1} \langle V_m \cdot ds_m \rangle \quad \text{(Equation 3)}$$

In Equation 3, <x, y> represents the dot product between vectors x and y and V represents the velocity vector between two consecutive points in the loop, $V=V_x\hat{i}+V_y\hat{j}+V_z\hat{k}$. In addition, ds represents the directional distance vector between two consecutive points in the loop in which $ds=S_x\hat{i}+S_y\hat{j}+S_z\hat{k}$, and M is the number of data points for a single cycle of the cardiac loop or PPG loop. Module 400 can calculate the circulation, e.g., up to an additional 5 features for the 3 waveform regions of a cardiac signal data and the 2 PPG signal data, as shown and described in relation to Table 2.

In addition, the circulation of a 2D projection in each of the 3 orthogonal planes can be determined, e.g., to provide up to an additional 15 features for the 3 waveform regions of cardiac signal data and the 2 PPG signal data.

Velocity of propagation can be calculated as the Euclidean distance between any two consecutive points of (i) the waveform regions of a cardiac loop or (ii) the PPG loops divided by the time difference between the sampling of the two points. Because the sampling rate is kept constant across all the patients, the distance between two consecutive points can be used as an indicator of the velocity of propagation. For an example cardiac signal, the time difference is a constant value of 1/1000 (for a downsampled signal of 1000 Hz). For a PPG signal, the time difference is a constant value of 1/250 (for a downsampled signal of 250 Hz). Module 400 can calculate the maximum velocity value and the average velocity value, e.g., up to 10 features for the 3 waveform regions of a cardiac signal data and the 2 PPG signal data, as shown and described in relation to Table 2.

Eccentricity can approximate the extent of deviation of a loop from being circular using the lengths of a perpendicular major and a minor axis projected onto a loop, per Equation 4.

$$e=\text{sqrt}(1-b_2/a_2) \quad \text{(Equation 4)}$$

In Equation 4, b is the length of the minor axis (736) of the loop, and a is the length of the major axis (738) of the loop. In the example shown in FIGS. 7E, the eccentricity 734 of a projection is shown for the VD waveform region 710*a* of cardiac signal data. Module 400 can calculate eccentricity for each of the 3 orthogonal projections of each of the 3 waveform regions of the cardiac signal data or the 2 PPG signals, e.g., to provide up to 15 features.

Example #2—Visual Vector Features

Figure 10G:
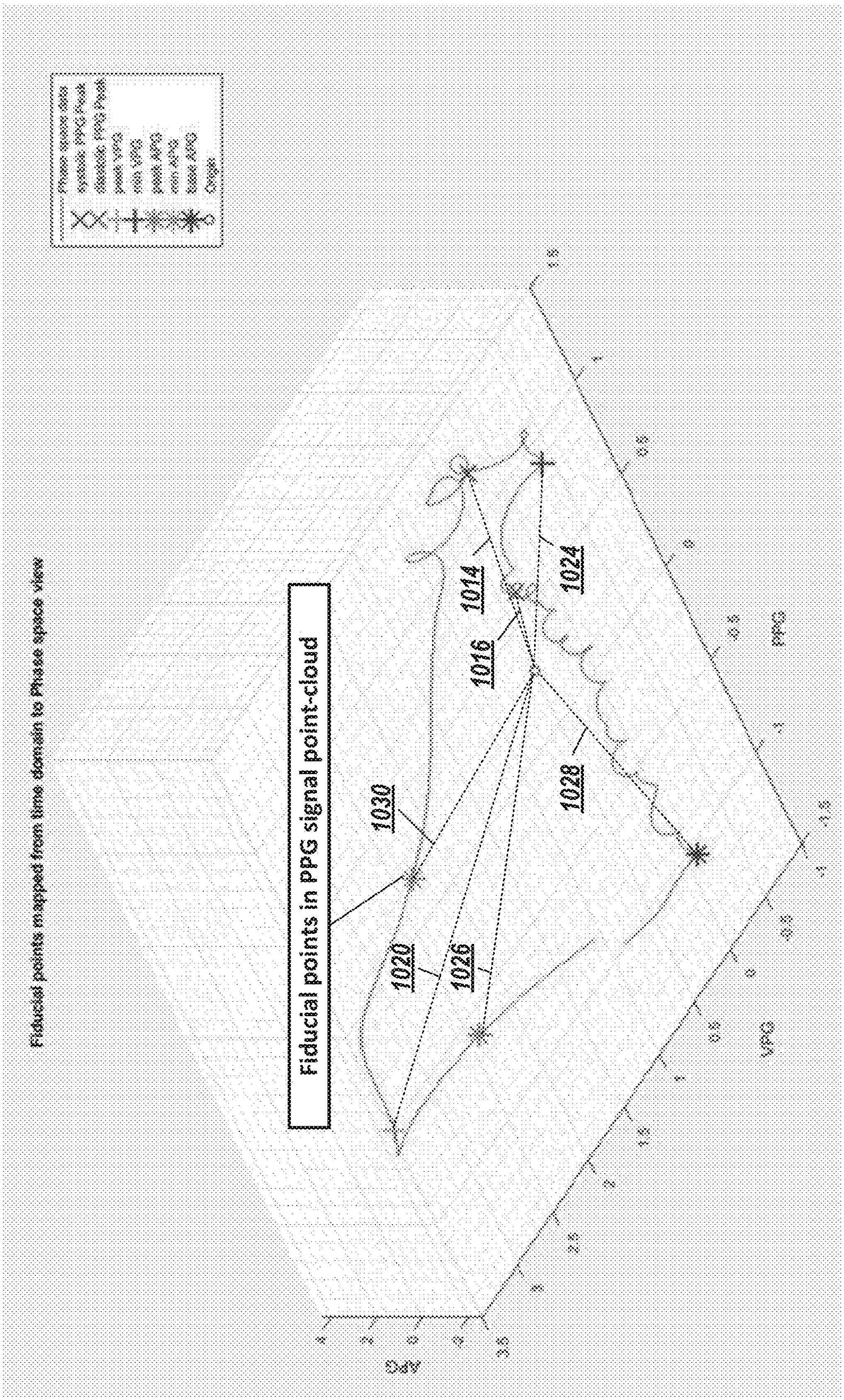

FIG. 5 illustrates, as the second of the two example visual feature categories, an example visual loop feature assessment module 500 configured to determine output values of visual features or parameters that characterize visual properties in 3D phase space such as vector amplitude, vector azimuth and elevation angles-associated features, octant location of certain vectors, and vorticity of a set of vectors defined in the 3D phase space model. FIGS. 10A-10F show these vectors as the maximal atrial depolarization vector (MADV) (1002), the atrial repolarization vector (ARV) (1004), the maximal ventricular depolarization vector (MVDV) (1006), the initial ventricular depolarization vector (IVDV) (1008), the terminal ventricular depolarization vector (TVDV) (1010), and the maximal ventricular repolarization vector (MVRV) (1012) for a cardiac signal. For PPG signal data, FIG. 10G shows vectors can be defined by fiducial points defined in the PPG, VPG, and APG waveforms, including the systolic, diastolic, pulse base PPG landmark vectors (1014, 1016, 1018, respectively); the VPG peak, base, min landmark vectors (1020, 1022, 1024, respectively), and APG peak, base, min landmark vectors (1026, 1028, 1030, respectively). Definitions of these vectors are provided in Table 6. Additional features may be determined for 2D projections of the 3D vectors.

Table 5 shows an example set of 5 extracted visual vector features that can be extracted from a biophysical signal such as a cardiac signal or PPG signal. In an embodiment, the 5 visual vector features can be determined for, some or all of, the cardiac or biopotential signal and for 2 PPG signals to provide up to a total of 82 features. In Table 5, features designated with the symbol "*" have been experimentally determined to have significant utility in the assessment of the presence or non-presence of at least one cardiac disease, medical condition, or an indication of either such as the determination of presence or non-presence of elevated LVEDP. In Table 5, features designated with the symbol "**" have been experimentally determined to have significant utility in the assessment of the presence or non-presence of at least one cardiac disease, medical condition, or an indication of either such as the determination of presence or non-presence of coronary artery disease. The list of the specific features determined to have significant utility in the assessment of the presence or non-presence of abnormal or elevated LVEDP and the presence or non-presence of significant CAD is provided in Tables 10A and 10B and Tables 11A and 11B, respectively.

TABLE 5

| Feature Name | Feature Description |
|---|---|
| 3dAmplitude*, ** | Magnitude of a vector in 3D phase space of each vector (Table 6) of the cardiac signals and PPG signals. |

TABLE 5-continued

| Feature Name | Feature Description |
|---|---|
| AzimuthAngle** (also referred to as "Azimuth") | Angle of a 2D projection of 3D vector in 3D phase space to a pre-defined axis of each vector (Table 6) of the cardiac signal. |
| ElevationAngle** (also referred to as "Elevation") | Angle of a 3D vector in 3D phase space to a pre-defined orthogonal plane of each vector (Table 6) of the cardiac signal and the PPG signals. |
| OctantLocation | Octant number for the endpoint of each vector (Table 6) of the cardiac signal. |
| Vorticity** | Vorticity of the vectors (Table 6) of the cardiac signals. |

TABLE 6

| Vector Name | Vector Description |
|---|---|
| Maximal Atrial Depolarization vector (MADV) | Vector between the origin and the maximum amplitude of the AD waveform region. |
| Atrial Repolarization vector (ARV) | The AD waveform region is not a closed cycle. The ARV joins the endpoints of the discontinuous AD loop. |
| Maximal Ventricular Depolarization vector (MVDV) | Vector between the origin and the maximum amplitude of the VD waveform region. |
| Initial Ventricular Depolarization vector (IVDV) | Vector corresponding to an initial phase of the VD waveform region. |
| Terminal Ventricular Depolarization vector (TVDV) | Vector corresponding to the terminal phase of the VD waveform region. |
| Maximal Ventricular Repolarization vector (MVRV) | Vector between the origin and the maximum amplitude of the VR waveform region. |
| sysPPG vector | Vector between the origin and systolic PPG landmark |
| diasPPG vector | Vector between the origin and diastolic PPG landmark |
| peakVPG vector | Vector between the origin and VPG peak landmark |
| minVPG vector | Vector between the origin and VPG min landmark |
| baseVPG vector | Vector between the origin and VPG base landmark |
| peakAPG vector | Vector between the origin and APG peak landmark |
| minAPG vector | Vector between the origin and APG min landmark |
| baseAPG vector | Vector between the origin and APG base landmark |

Table 7 shows an example set of additional 6 types of extracted visual vector features that can be extracted from a biophysical signal such as a cardiac signal or PPG signal based on a projection of the amplitude to an orthogonal plane or an angle to an orthogonal plane. In an embodiment, the 6 visual vector features can be determined for, some or all of, the cardiac or biopotential signal and for 2 PPG signals to provide up to a total of 150 features. In Table 7, features designated with the symbol "*" have been experimentally determined to have significant utility in the assessment of the presence or non-presence of at least one cardiac disease, medical condition, or an indication of either such as the determination of presence or non-presence of elevated LVEDP. In Table 7, features designated with the symbol "**" have been experimentally determined to have significant utility in the assessment of the presence or non-presence of at least one cardiac disease, medical condition, or an indication of either such as the determination of presence or non-presence of coronary artery disease. The list of the specific features determined to have significant utility in the assessment of the presence or non-presence of abnormal or elevated LVEDP and the presence or non-presence of significant CAD is provided in Tables 10A and 10B and Tables 11A and 11B, respectively.

TABLE 7

| Feature Name | Feature Description |
|---|---|
| 2dAmplitude_Plane [XY, XZ, YZ]*, ** | Magnitude of a projection of a given vector in a given orthogonal plane. |
| 2dAngle_Plane [XY, XZ, YZ]*, ** | Angle a projection vector makes with the horizontal axis for a given orthogonal plane, e.g., in degrees. |
| VDVR_PlanarAngle | Angle between the ventricular depolarization (VD) plane and ventricular repolarization (VR) plane, e.g., in degrees. |
| PairWiseVector_3dAngle* | Angle defined between two vectors in phase space. |
| PairWiseVector_2dAngle_Plane*, ** [XY, XZ, YZ] | Angle defined between two vectors in phase space in a given orthogonal plane. |

Vector Amplitude Features. FIGS. 10A-10G show example operations to compute amplitude features for cardiac and PPG signals. Each vector feature can be specified by a start position (e.g., $x_{start}$, $y_{start}$, $z_{start}$ for a cardiac signal) and an end position (e.g., $x_{end}$, $y_{end}$, $z_{end}$) in the loops of the cardiac or PPG signal. Module 500 can determine the vector amplitude as the magnitude of a three-dimensional vector by computing the square root of the sum of the squared ORTH1, ORTH2, and ORTH3 components (for cardiac) of a vector, or the square root of the sum of the squared PPG, VPG and APG components (for PPG) of a vector, respectively. Module 500 can determine the vector amplitude values for the 6 cardiac vectors and 8 PPG vectors of Table 6, e.g., to provide up to 22 features for the cardiac signal data and the 2 PPG signal data.

In addition, Module 500 can calculate the magnitude of the projection of a given vector in the 3 orthogonal planes, e.g., as the square root of the sum of orthogonal components of the projection. Module 500 can thus determine the 2dAmplitude values for the 6 cardiac vectors and 8 PPG vectors of Table 6 for the 3 orthogonal planes, e.g., to provide up to 66 features for the cardiac signal data and the 2 PPG signal data.

Figure 11A:
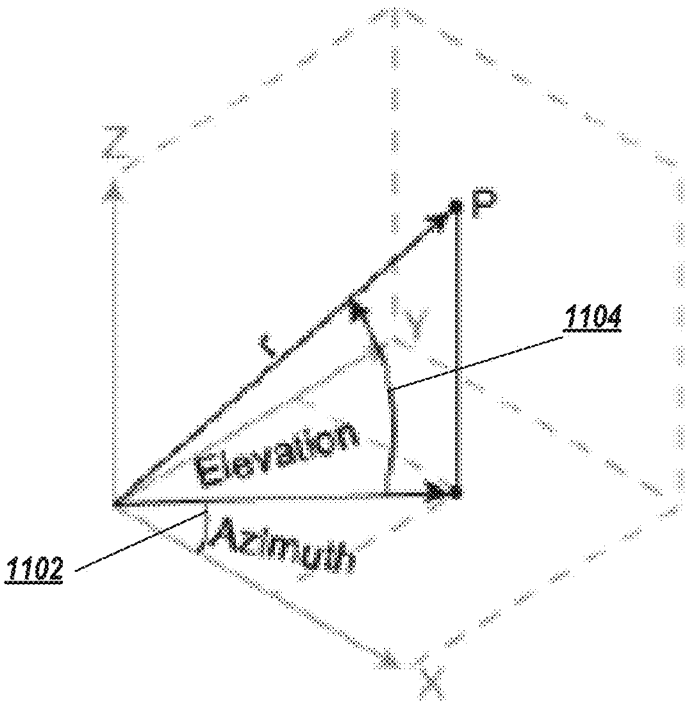

Vector Azimuth, Elevation Angle, 2dAngle, VDVR Angle, 3dAngle VectorPair, 2dAngle VectorPair features. Vector azimuth angle is the angle of a 2D projection of 3D vector in 3D phase space to a pre-defined axis of each vector of the cardiac signals and PPG signals. Elevation Angle is the angle of a given vector and the projection of the vector in a pre-defined orthogonal plane (e.g., ORTH12 plane). The features may be calculated in degrees (or radians). FIG. 11 shows a diagram of the vector azimuth angle 1102 and the elevation angle 1104. Module 500 can determine (i) the vector azimuth angle values and the elevation angle values for the 6 cardiac vectors and (ii) the elevation angles of the 8 PPG vectors of Table 6, e.g., to provide up to 28 features for the cardiac signal data and the 2 PPG signal data.

In addition, Module 500 can calculate the angle a projection vector makes with the horizontal axis for a given orthogonal plane of the three orthogonal planes. The magnitude of the angle (Theta) can be calculated in degrees. Module 500 can thus determine the 2dAngle values for the 6 cardiac vectors and 8 PPG vectors of Table 6 for the 3 orthogonal planes, e.g., to provide up to 66 features for the cardiac signal data and the 2 PPG signal data.

In addition, Module 500 can calculate the angle (VDVR Angle) between the ventricular depolarization plane and ventricular repolarization plane as a feature of Table 6. The ventricular depolarization plane can be defined as the plane with the least square residue for all the points in the ventricular depolarization loop.

In addition, Module 500 can calculate 3D angles between vector pairs (3dAngle VectorPairs) of the cardiac signal. Example vector pairs includes (i) the MVDV and MVRV vector pair, (ii) the IVDV and MVRV vector pair, (iii) the TVDV and MVRV vector pair, (iv) the IVDV and MVDV vector pair, and (v) the TVDV and MVDV vector pair. Module 500 can also calculate three 2D angles (i) between projections of the two vectors in the ORTH12 plane, (ii) between projections of the two vectors in the ORTH13 plane, and (iii) between projections of the two vectors in the ORTH23 plane.

Module 500 can thus determine the 3dAngle values and the three 2dAngle values for the 5 cardiac vector pairs, e.g., to provide up to 20 features for the cardiac signal data.

Octant Location and Vorticity Vector features. Octant location is the location of the endpoint of a given vector by its octant identifier (see Table 4) for the cardiac signal data. Module 500 can determine the octant numbers for the 6 cardiac vectors of Table 6, e.g., to provide up to 6 features for the cardiac signal data.

Vorticity represents the rotation of the points comprising the loop in phase space as described in relation to Equation 2. Module 500 can determine vorticity for the 5 MADV, ARV, MVDV, IVDV, TVDV vectors of Table 6, e.g., up to 5 features for the cardiac signal data.

Figure 11B:
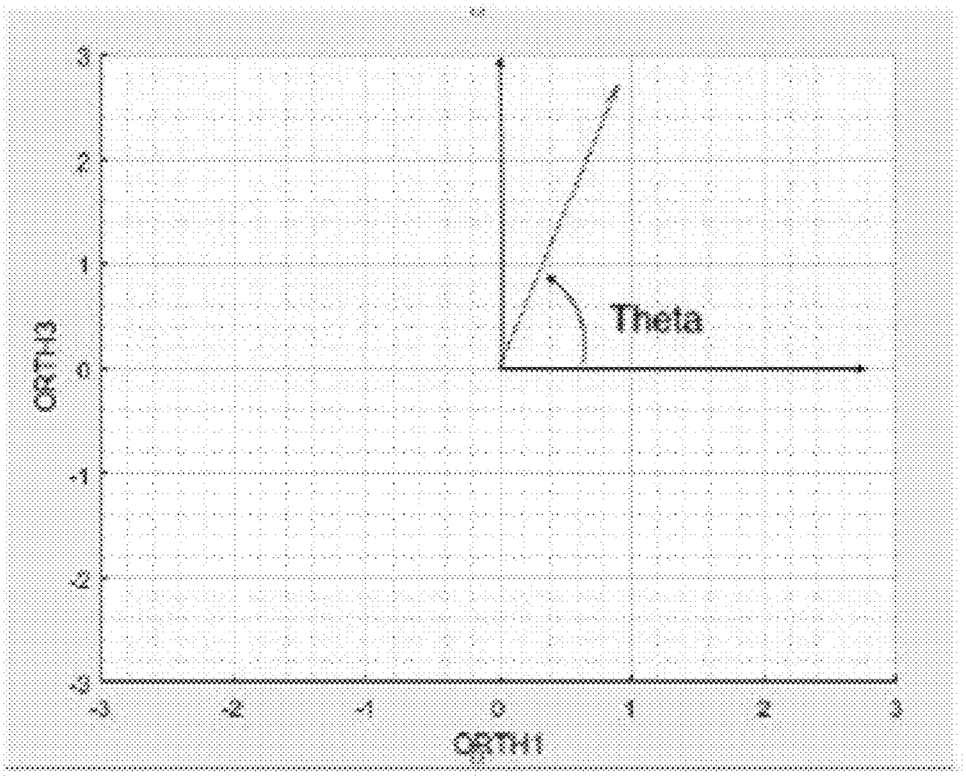

2dAngle_Plane feature. 2dAngle is the angle a projection vector makes with the horizontal axis for a given orthogonal plane, e.g., in degrees (see FIG. 11B). Module 500 can determine the 2dAngle for the 6 cardiac vectors of Table 6 in the 3 orthogonal planes, e.g., to provide up to 18 features for the cardiac signal data.

Example #3—Visual Features

In addition to the features discussed herein, e.g., in Example #1 and Example #2, cos/sin encoding may be applied to remove discontinuity at the boundaries of waveforms to generate a new class of features. Because of the "circularity" of the data in phase space, the discontinuity may form at the boundaries. For example, 10.0 degrees and 359.9 may be only 10.1 degrees apart considering the transition over the boundary but may appear to be 349.0 degrees apart (359.9−10.0). The use of cos/sin encoding can facilitate the explicit encoding of that circulation at the cost of expanding from one feature to two.

Example Method of Computation

As stated above, FIG. 6 shows an implementation (600) of the visual loop feature computation module 400 or 500 in accordance with an illustrative embodiment, which can be used wholly, or partially, to generate visual loop features or parameters, and their outputs, to be used in machine-learned classifier to determine a metric associated with a physiological system of a patient under study. To determine the example features of Table 2, Method 600, in some embodiments, includes (i) signal preparation (602), (ii) isolating (604) waveform regions of interest, (iii) generating (606) a point-cloud phase space model of the isolated signal, and (iv) determine visual features. FIG. 6 shows an example cardiac-signal phase space model 610 comprising multiple cardiac cycle data identified for three segment regions of interest, namely, the AD waveform regions 612, VD waveform regions 614, and VR waveform regions 616. The phase space model 610 also shows regions 618 not part of these three regions. FIG. 6 shows an example of PPG-signal phase space model 620 generated for a PPG signal 622 and its associated VPG signal 624 and APG signal 626. FIG. 6 also shows the PPG-signal phase space model 620 with fiducial points of interest, including a systolic PPG peak 628, a diastolic PPG peak 630, a peak VPG 632, a min VPG 634, a peak APG 636, a min APG 638, a base APG 640, and an origin 640.

Cardiac-Signal Preparation (602). For an example cardiac signal having 3 orthogonal signals, Module 400 or 500 can (i) downsample (e.g., via decimation) the acquired signals to 1 kHz, (ii) remove the transient portion of the signals (e.g., the first 31 from the acquired signals), (iii) remove baseline wander (e.g., via a $2^{nd}$ order forward-reverse 0.67 Hz high-pass filter), and (iv) window the signal to generate sub-signals (e.g., split into eight sub-signal of 30-second duration with 15 seconds of overlap between consecutive sub-signals).

Figure 12A:
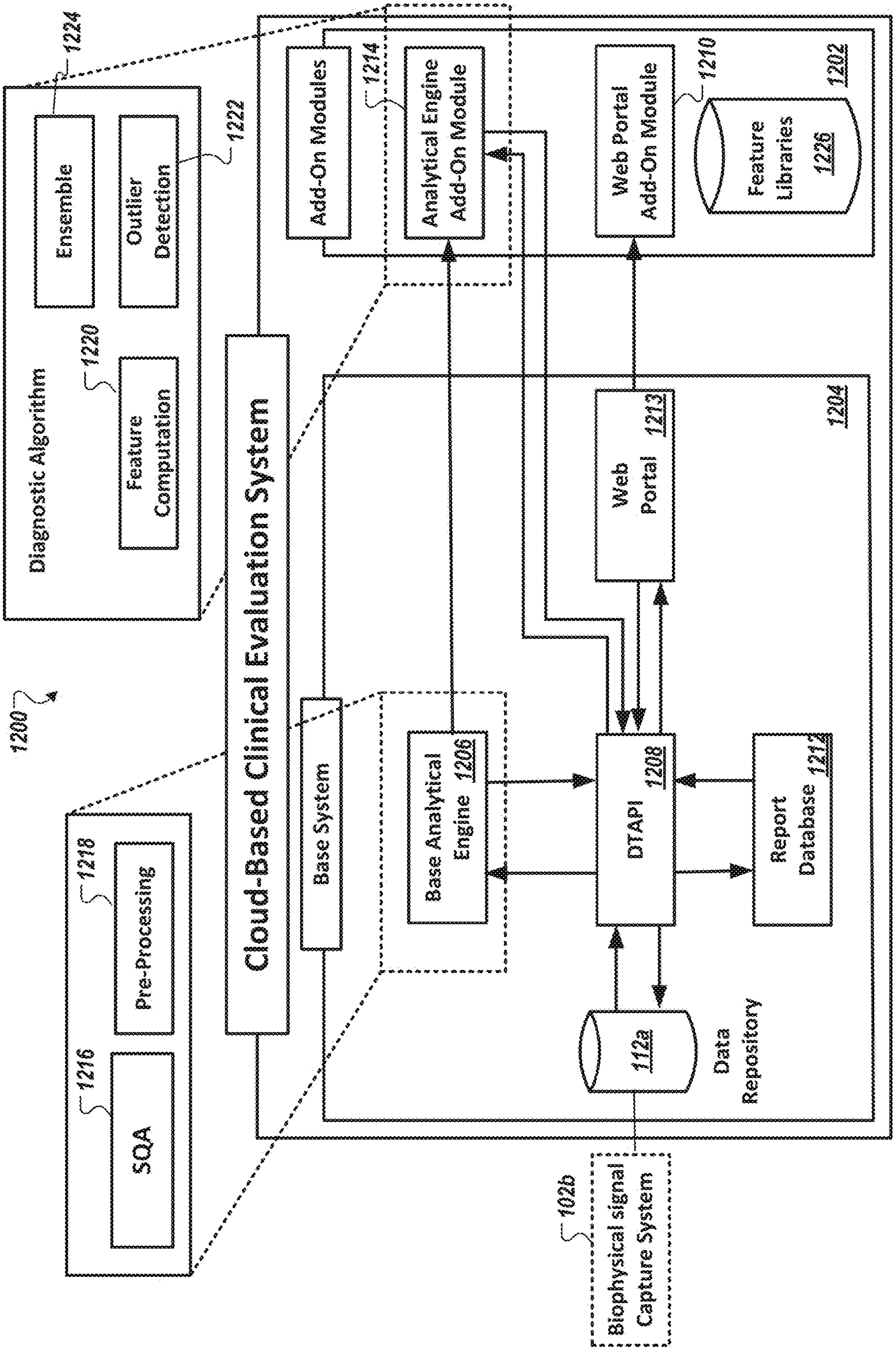
FIG. 12A shows a schematic diagram of an example clinical evaluation system configured to use visual features among other computed features to generate one or more metrics associated with the physiological state of a patient in accordance with an illustrative embodiment.

Cardiac-Signal Delineation (604). Module 400 or 500 can isolate the pre-processed cardiac signals into waveform regions associated with atrial depolarization (also referred to as "P wave"), waveform regions associated with ventricular depolarization (also referred to as QRS wave or peaks), and waveform regions associated with ventricular repolarization (also referred to as "T wave"). FIG. 12A shows an example implementation of Module 400 or 500 to isolate the pre-processed cardiac signals into waveform regions of interest. In the example shown in FIG. 12A, Module 400 or 500 can (i) transform the pre-processed cardiac signals to a single time-series $$\hat{y}\ \left(\text{e.g., } \hat{y} = \sqrt{y_X^2 + y_Y^2 + y_Z^2}\right),$$

(ii) detect peaks (e.g., ventricular depolarization) in each cycle of the transformed time series ($\hat{y}$), (iii) detect a corresponding ventricular depolarization (VD) onset and ventricular depolarization (VD) offset region of the transformed time series ($\hat{y}$), and (iv) segment the signal between the $VD_{off,i}$ and the next consecutive cycle $VD_{onset,i+1}$ and assigning two-thirds of the segment as the ventricular repolarization region and the remaining one-third as the atrial depolarization (P-wave) regions. Other segmentation may be used, for example, as described in D. B. Dubin, Rapid Interpretation of EKG's: An interactive course, 6th ed. tampa: Cover Pub, 2000.

Ventricular depolarization can be determined, per step (ii), using any number of peak detection operators configured to detect local maxima (e.g., a "findpeak" function of Matlab manufactured by Mathworks). To determine the ventricular depolarization (VD) onset and ventricular depolarization (VD) offset region, per step (iii) Module 400 or 500 can (a) decompose the pre-process signals per channel using a wavelet transform (e.g., using a continuous 1-D Morlet wavelet or Gaussian, Mexican Hat, Spline, and Mayer wavelet (e.g., as a mother wavelet)), (b) filter the wavelet spectrum (e.g., via a bandpass filter between 40-60 Hz), (c) generate a time-series signal from bandpass filtered wavelet spectrum, and (d) determine indices in the reconstructed signal having cumulative power that falls below a dynamic threshold (e.g., QRS onset and offset are assigned to time indices when the cumulative power falls below a dynamic threshold, e.g., top 25 percentile of the cumulative power, the first time before and after each detected QRS peak).

PPG-Signal Preparation (602). For a set of photoplethysmographic signals, Module 400 or 500 can (i) downsample the acquired signals to 250 Hz, (ii) remove the transient portion of the signals (e.g., the first 10 seconds and the last 2 seconds from both the signals), (iii) generate velocityplethysmogram (VPG) and accelerationplethysmogram (APG) from the PPG signals (e.g., as a difference in amplitudes of consecutive points in the PPG signal or a difference in amplitudes of consecutive points in the VPG signal), and (iv) normalize the signal values of the PPG, VPG, and APG signals between the two acquired PPG signals (e.g., using a z-score transformation).

PPG-Signal Delineation (604). Module 400 or 500 can delineate the pre-processed PPG, VPG, and APG signals to identify the systolic, diastolic, pulse base PPG landmark vectors (1014, 1016, 1018, respectively); the VPG peak, base, min landmark vectors (1020, 1022, 1024, respectively), and APG peak, base, min landmark vectors (1026, 1028, 1030, respectively). Example methods are summarized in Tables 8A, 8B, and 8C for PPG landmarks, VPG landmarks, and APG landmarks, respectively.

TABLE 8A

| PPG Fiducial Landmarks | Example Method of Computation |
|---|---|
| PPG pulse base | PPG pulse base may be detected and used for the detection of other landmarks. PPG pulse base can be determined by (i) inverting the preprocessed PPG signal, (ii) performing a peak detection in which a peak has a minimum pulse of 125 ms, (iii) filtering the detected peaks, and (iv) re-inverting the signal again back to its original position. The filter can use criteria: (a) a minimum peak width (at the half-prominence) having less than the minimum pulse width of 125 ms, (b) pulse base values should be smaller than zero, (c) and pulse base value should be less than ten scaled median absolute deviations (MAD) away from the median of the detected pulse bases. |
| Systolic peak | Systolic peak can be detected with a minimum pulse of 125 ms. The detected peaks may be filtered using the criteria: (a) the minimum peak width (at the half-prominence) being less than the minimum pulse width of 125 ms and (b) systolic peak values being less than ten-scaled median absolute deviations (MAD) away from the median of the detected pulse bases. A maximum filter may be applied to detect the maximum values of the detected peaks within two consecutive pulse bases as the systolic peak for a corresponding cycle. |
| Diastolic peak | Diastolic peak can be detected by (i) segmenting the PPG signal using indexes of VPG min at cycle n and the consecutive PPG pulse base at cycle n + 1, (ii) smoothing the segmented PPG (e.g., via a Gaussian-weighted moving average filter), (iii) determining a VPG signal from the smoothed PPG signal, (iv) detecting peaks in the determined VPG signal, and (v) filtering the VPG peaks for local maxima with a time constraint that the local maxima be at the first 50% of indexes of the segmented VPG. |

TABLE 8B

| VPG Fiducial Landmarks | Example Method of Computation |
|---|---|
| VPG peak | VPG peak can be determined by (i) segmenting indexes from a PPG signal corresponding to a monotonically increasing segment in the PPG signal ("PPG raise-segments" identified between the PPG pulse base at cycle n and a consecutive PPG systolic peak at cycle n + 1), (ii) detecting VPG peaks using a peak finder operator (e.g., configured with a minimum pulse width of 25% of the median of the PPG raise-duration), (iii) filtering the detected peaks using the criteria: (a) the minimum peak width (at the half-prominence) be less than the VPG minimum pulse width and (b) VPG peak values be less than ten scaled MAD away from the median of the detected peaks, and (iv) applying a maximum filter to identify the maximum value of the detected peaks within the PPG raise-segment as the VPG peak for the corresponding cycle. |
| VPG min | VPG min can be determined by (i) segmenting the PPG signal using the indexes of PPG systolic peak at cycle n and the consecutive PPG pulse base at cycle n + 1, (ii) smoothing the segmented PPG (e.g., via a Gaussian-weighted moving average filter), (iii) determining an inverted VPG signal from the smoothed PPG, and (iv) detect peaks of the inverted VPG (e.g., by filtering for peaks having a time constraint that the VPG min occurs at the first 30% of indexes of the segmented VPG and applying a maximum filter to the original VPG (non-smoothed) to search for local minima around the detected VPG min in the smoothed VPG). |
| VPG base | VPG base can be determined by (i) correcting a baseline from the VPG signal that may occur during the numerical derivatization of PPG (e.g., using a percentile filtering to identify the data points with the values between the 20% and 50% percentile of the VPG signal and then subtracting the VPG signal from the mean of the percentile filtered VPG), (ii) segmenting the baseline-corrected VPG using the indexes of VPG min at cycle n and a consecutive VPG peak at cycle n + 1, and (iii) determining the VPG bases at zero-crossing of the VPG where VPG bases are removed that are less than four-scaled median absolute deviations (MAD) away from the median of the detected bases. |

TABLE 8C

| APG Fiducial Landmarks | Example Method of Computation |
|---|---|
| APG peak | APG peak can be determined by (i) segmenting the PPG signal using the indexes PPG pulse base at cycle n and the consecutive PPG systolic peak at cycle n + 1, (ii) detecting AGP peaks so that the maximum value of the detected peaks within the segment is more than six scaled MAD away from the median. |
| APG min | APG min can be determined by (i) segmenting the PPG signal using the indexes of the PPG pulse base at cycle n and the consecutive PPG systolic peak at cycle n + 1, (ii) smoothing the segmented PPG (e.g., via Gaussian-weighted moving average filter), (iii) determining an inverted APG signal from the smoothed PPG, (iv) detecting peaks of the inverted APG (e.g., having a time constraint that the APG min occurs at the first 75% of indexes of the segmented APG), and (v) applying a minimum filter to find the minimum value in the original APG (non-smoothed) in the smoothed APG. |
| APG base | APG base can be determined by performing a percentile filtering of the APG signal to identify the data points with the values between the 25% and 75% percentile, (ii) subtracting the APG signal from the mean of the percentile filtered APG, (iii) segmenting the baseline-corrected APG using the indexes of APG min at cycle n and a consecutive APG peak at cycle n + 1, and (iv) determining the APG bases through zero-crossing the VPG where VPG bases are removed that are less than four-scaled median absolute deviations (MAD) away from the median of the detected bases. |

Experimental Results and Examples

Several development studies have been conducted to develop feature sets, and in turn, algorithms that can be used to estimate the presence or non-presence, severity, or localization of diseases, medical conditions, or an indication of either. In one study, algorithms were developed for the non-invasive assessment of abnormal or elevated LVEDP. As noted above, abnormal or elevated LVEDP is an indicator of heart failure in its various forms. In another development study, algorithms and features were developed for the non-invasive assessment of coronary artery disease.

As part of these two development studies, clinical data were collected from adult human patients using a biophysical signal capture system and according to protocols described in relation to FIG. 2. The subjects underwent cardiac catheterization (the current "gold standard" tests for CAD and abnormal LVEDP evaluation) following the signal acquisition, and the catheterization results were evaluated for CAD labels and elevated LVEDP values. The collected data were stratified into separate cohorts: one for feature/algorithm development and the other for their validation.

Within the feature development phases, features were developed, including the visual features, to extract characteristics in an analytical framework from biopotential signals (as an example of the cardiac signals discussed herein) and photo-absorption signals (as examples of the hemodynamic or photoplethysmographic discussed herein) that are intended to represent properties of the cardiovascular system. Corresponding classifiers were also developed using classifier models, linear models (e.g., Elastic Net), decision tree models (XGB Classifier, random forest models, etc.), support vector machine models, and neural network models to non-invasively estimate the presence of an elevated or abnormal LVEDP. Univariate feature selection assessments and cross-validation operations were performed to identify features for use in machine learning models (e.g., classifiers) for the specific disease indication of interest. Further description of the machine learning training and assessment are described in U.S. Provisional Patent Application No. 63/235,960, filed Aug. 23, 2021, entitled "Method and System to Non-Invasively Assess Elevated Left Ventricular End-Diastolic Pressure," which is hereby incorporated by reference herein in its entirety.

The univariate feature selection assessments evaluated many scenarios, each defined by a negative and a positive dataset pair using a t-test, mutual information, and AUC-ROC evaluation. The t-test is a statistical test that can determine if there is a difference between two sample means from two populations with unknown variances. Here, the t-tests were conducted against a null hypothesis that there is no difference between the means of the feature in these groups, e.g., normal LVEDP vs. elevated (for LVEDP algorithm development); CAD− vs. CAD+ (for CAD algorithm development). A small p-value (e.g., ≤0.05) indicates strong evidence against the null hypothesis.

Mutual information (MI) operations were conducted to assess the dependence of elevated or abnormal LVEDP or significant coronary artery disease on certain features. An MI score greater than one indicates a higher dependency between the variables being evaluated. MI scores less than one indicates a lower dependency of such variables, and an MI score of zero indicates no such dependency.

A receiver operating characteristic curve, or ROC curve, illustrates the diagnostic ability of a binary classifier system as its discrimination threshold is varied. The ROC curve may be created by plotting the true positive rate (TPR) against the false positive rate (FPR) at various threshold settings. AUC-ROC quantifies the area under a receiver operating characteristic (ROC) curve—the larger this area, the more diagnostically useful the model is. The ROC, and AUC-ROC, value is considered statistically significant when the bottom end of the 95% confidence interval is greater than 0.50.

Table 6 shows an example list of the negative and a positive dataset pair used in the univariate feature selection assessments. Specifically, Table 6 shows positive datasets being defined as having an LVEDP measurement greater than 20 mmHg or 25 mmHg, and negative datasets were defined as having an LVEDP measurement less than 12 mmHg or belonging to a subject group determined to have normal LVEDP readings.

TABLE 6

| Negative Dataset | Positive Dataset |
|---|---|
| ≤12 (mmHg) | ≥20 (mmHg) |
| ≤12 (mmHg) | ≥25 (mmHg) |
| Normal LVEDP | ≥20 (mmHg) |
| Normal LVEDP | ≥25 (mmHg) |

Tables 10A and 10B each shows a list of visual features having been determined to have utility in estimating the presence and non-presence of elevated LVEDP in an algorithm executing in a clinical evaluation system. The features of Tables 10A and 10B and corresponding classifiers have been validated to have clinical performance comparable to the gold standard invasive method to measure elevated LVEDP.

TABLE 10A

| Feature_name | t-test | AUC | MI |
|---|---|---|---|
| AD_2dArea_ORTH12_Overall | n/s | 0.5136 | n/s |
| AD_AverageVorticity | n/s | 0.5001 | 1.5210 |
| AD_Max2dAreaQuadNum_ORTH13[1] | n/s | 0.5005 | n/s |
| AD_SurfaceArea_AlphaShape_Octant6 | 0.0442 | 0.5089 | n/s |
| AD_SurfaceArea_ConvexHull_Octant6 | n/s | 0.5022 | n/s |
| AD_Volume_AlphaShape_Octant6 | n/s | 0.5085 | 1.0457 |
| AD_Volume_AlphaShape_Overall | n/s | 0.5086 | n/s |
| AD_Volume_ConvexHull_Octant6 | n/s | 0.5062 | n/s |
| IVDV_MVRV_3dAngle | 0.0483 | 0.5035 | n/s |
| MADV_2DAngle_ORTH13[1] | 0.0242 | 0.5071 | n/s |
| MADV_OctantNum[1] | 0.0093 | 0.5189 | n/s |
| TVDV_2DAmplitude_ORTH13 | 0.0166 | 0.5118 | n/s |
| VD_2dArea_ORTH12_Quad2 | n/s | 0.5032 | n/s |
| VD_SurfaceArea_AlphaShape_Overall | n/s | 0.5068 | n/s |
| VD_SurfaceArea_ConvexHull_Octant3[1] | n/s | 0.5177 | n/s |
| VD_Volume_AlphaShape_Octant3 | 0.0320 | 0.5048 | n/s |
| VD_Volume_AlphaShape_Overall | n/s | 0.5107 | n/s |
| VR_2dArea_ORTH12_Overall | n/s | n/s | n/s |
| VR_2dArea_ORTH12_Quad1[1] | 0.0111 | 0.5034 | n/s |
| VR_2dArea_ORTH13_Quad4 | n/s | 0.5142 | n/s |
| VR_2dPerimeter_ORTH23_Quad3[1] | n/s | 0.5131 | n/s |
| VR_Max2dAreaQuadNum_ORTH13 | 0.0498 | 0.5134 | n/s |
| VR_Max2dPerimeterQuadNum_ORTH13 | n/s | 0.5079 | n/s |
| VR_SurfaceArea_AlphaShape_Octant2 | n/s | 0.5084 | 1.1432 |
| VR_SurfaceArea_AlphaShape_Octant5 | 0.0410 | 0.5198 | n/s |
| VR_SurfaceArea_AlphaShape_Octant7 | n/s | 0.5112 | n/s |
| VR_SurfaceArea_ConvexHull_Octant3 | n/s | 0.5018 | n/s |
| VR_SurfaceArea_ConvexHull_Octant5 | 0.0251 | 0.5111 | n/s |
| VR_SurfaceArea_ConvexHull_Octant7 | n/s | 0.5061 | n/s |
| VR_Volume_AlphaShape_Octant2 | n/s | 0.5087 | n/s |
| VR_Volume_AlphaShape_Octant5 | n/s | 0.5229 | n/s |
| VR_Volume_AlphaShape_Octant7 | n/s | 0.5025 | n/s |
| VR_Volume_AlphaShape_Overall | n/s | 0.5096 | n/s |
| VR_Volume_ConvexHull_Octant3 | n/s | 0.5004 | n/s |
| VR_Volume_ConvexHull_Octant5 | 0.0315 | 0.5131 | n/s |
| VR_Volume_ConvexHull_Octant7 | n/s | 0.5147 | n/s |

FA_scenario = LVEDP <= 12 (N = 246) vs >=20 (N = 209)

[1]= LVEDP <= 12 (N = 246) vs >=25 (N = 78)

TABLE 10B

| Feature_name | t-test | AUC | MI |
|---|---|---|---|
| lowerPPG_2dArea_PPGVPG_Overall | n/s | 0.5013 | n/s |
| lowerPPG_2dPerimeter_PPGVPG_Overall | 0.0367 | 0.5087 | n/s |
| lowerPPG_3dMaxCurvature | n/s | 0.5110 | n/s |
| lowerPPG_3dMeanCurvature | n/s | 0.5035 | n/s |
| lowerPPG_3dPerimeter_Overall[1] | 0.0004 | 0.5598 | n/s |
| lowerPPG_AverageVelocity[1] | 0.0011 | 0.5422 | n/s |
| lowerPPG_AverageVorticity[1] | 0.0053 | 0.5540 | 1.3348 |
| lowerPPG_baseAPG_2DAmplitude_PPGVPG[1] | 0.0495 | 0.5118 | n/s |
| lowerPPG_baseAPG_2DAngle_PPGAPG[1] | n/s | 0.5048 | n/s |
| lowerPPG_baseAPG_3DAmplitude[1] | 0.0432 | 0.5163 | n/s |
| lowerPPG_baseAPG_Elevation | 0.0049 | 0.5245 | n/s |
| lowerPPG_baseVPG_2DAngle_VPGAPG1[2] | n/s | 0.6154 | 1.1435 |
| lowerPPG_Circulation[1] | 0.0010 | 0.5410 | n/s |
| lowerPPG_Circulation_PPGVPG | n/s | 0.5057 | n/s |
| lowerPPG_diasPPG_2DAmplitude_VPGAPG[1] | n/s | n/s | n/s |
| lowerPPG_diasPPG_2DAngle_PPGVPG | 0.0104 | 0.5276 | 1.0339 |
| lowerPPG_diasPPG_2DAngle_VPGAPG | 0.0026 | 0.5363 | 1.0769 |
| lowerPPG_diasPPG_Elevation[2] | n/s | 0.6612 | 1.4782 |
| lowerPPG_min/sPG_Elevation[2] | n/s | 0.6108 | 1.3544 |
| lowerPPG_peakAPG_2DAmplitude_PPGAPG | n/s | 0.5029 | n/s |
| lowerPPG_peakAPG_2DAngle_PPGAPG[2] | 0.0110 | 0.6037 | 2.0493 |
| lowerPPG_peakAPG_2DAngle_VPGAPG | n/s | 0.5022 | n/s |
| lowerPPG_peakAPG_3DAmplitude[2] | 0.0469 | 0.5011 | 1.0522 |
| lowerPPG_peakAPG_Elevation | 0.0429 | 0.5042 | n/s |
| lowerPPG_sysPPG_2DAngle_PPGVPG | n/s | 0.5282 | n/s |
| lowerPPG_sysPPG_2DAngle_VPGAPG[2] | n/s | 0.6520 | 1.8989 |
| upperPPG_2dPerimeter_PPGVPG_Overall | 0.0357 | 0.5249 | n/s |
| upperPPG_3dMaxCurvature | n/s | 0.5034 | n/s |
| upperPPG_3dMeanCurvature | 0.0479 | 0.5121 | n/s |
| upperPPG_3dPerimeter_Overall | 0.0486 | 0.5113 | n/s |
| upperPPG_AverageVelocity | 0.0461 | 0.5090 | n/s |
| upperPPG_AverageVorticity[1] | 0.0074 | 0.5886 | 1.8733 |
| upperPPG_baseAPG_2DAmplitude_PPGAPG[1] | 0.0235 | 0.5226 | 1.0049 |
| upperPPG_baseAPG_2DAmplitude_PPGVPG[1] | 0.0175 | 0.5263 | n/s |
| upperPPG_baseAPG_3DAmplitude[1] | 0.0163 | 0.5319 | n/s |
| upperPPG_baseAPG_Elevation | 0.0032 | 0.5229 | 1.1439 |
| upperPPG_baseVPG_2DAngle_VPGAPG[1] | 0.0033 | n/s | 1.2714 |
| upperPPG_Circulation | n/s | 0.5167 | n/s |
| upperPPG_diasPPG_2DAngle_PPGVPG | 0.0296 | 0.5269 | n/s |
| upperPPG_diasPPG_2DAngle_VPGAPG | 0.0023 | 0.5415 | 1.2655 |
| upperPPG_min/sPG_2DAmplitude_PPGAPG[1] | 0.0057 | n/s | 1.0817 |
| upperPPG_min/sPG_2DAngle_VPGAPG | 0.0138 | 0.5172 | n/s |
| upperPPG_min/sPG_Elevation | 0.0137 | 0.5273 | 1.1942 |
| upperPPG_minVPG_2DAngle_PPGAPG | n/s | 0.5151 | n/s |
| upperPPG_minVPG_2DAngle_VPGAPG | n/s | 0.5046 | n/s |
| upperPPG_minVPG_Elevation | n/s | 0.5099 | n/s |
| upperPPG_peakAPG_2DAngle_PPGAPG[2] | 0.0046 | 0.5939 | 1.5293 |
| upperPPG_peakAPG_Elevation | 0.0456 | 0.5300 | n/s |
| upperPPG_sysPPG_2DAngle_PPGVPG | n/s | 0.5011 | n/s |

FA_scenario = LVEDP <= 12 (N = 246) vs >=20 (N = 209)
[1]= LVEDP <= 12 (N = 246) vs >=25 (N = 78)
[2]= LVEDP <= 25 (N = 95) vs CADHealth G2 (N = 37)

Tables 11A and 11B each shows a list of visual features having been determined to have utility in estimating the presence and non-presence of significant CAD in an algorithm executing in a clinical evaluation system. The features of Tables 11A and 11B and corresponding classifiers have been validated to have clinical performance comparable to the gold standard invasive method to measure CAD. Each of the features in Tables 11A and 11B (as well as 10A and 10B) is generally named by a vector (e.g., "AD," "IVDV," "MVDV," "TVDV," "VD," "baseVPG," "diasVPG," etc.), feature type (e.g., "2Dangle," "Azimuth"), and associated channels. Where applicable, the quandrant information (e.g., "Quad1," "Quad2," etc.) is provided between the feature type and the associated channels.

TABLE 11A

| Feature_name | t-test | AUC | MI |
|---|---|---|---|
| AD_2dArea_Quad1_ORTH23 | n/s | n/s | 1.2705 |
| AD_2dArea_Quad2_ORTH23 | n/s | n/s | 1.1969 |
| AD_3dMeanCurvature_ORTH123 | n/s | 0.5015 | n/s |
| IVDV_2DAngle_ORTH23 | n/s | n/s | 1.0460 |
| IVDV_cos2DAngle_ORTH23[3] | n/s | 0.5059 | n/s |
| IVDV_MVRV_cos2dAngle_ORTH12[3] | 0.0195 | 0.5156 | n/s |
| IVDV_MVRV_sin2dAngle_ORTH12[3] | 0.0296 | 0.5060 | n/s |
| MADV_2DAngle_ORTH12 | n/s | n/s | 1.1237 |
| MADV_Azimuth_ORTH123 | n/s | n/s | 1.1444 |

TABLE 11A-continued

| Feature_name | t-test | AUC | MI |
|---|---|---|---|
| MVDV_MVRV_2dAngle_ORTH13 | n/s | n/s | 1.0338 |
| MVDV_MVRV_sin2dAngle_ORTH13[3] | n/s | n/s | 1.2280 |
| MVDV_Sparsity_ORTH123 | 0.0472 | n/s | n/s |
| MVDV_TVDV_cos2dAngle_ORTH12[3] | n/s | n/s | 1.1059 |
| MVDV_TVDV_sin2dAngle_ORTH23[3] | 0.0401 | n/s | n/s |
| MVRV_Vorticity_ORTH123 | n/s | n/s | 1.0396 |
| TVDV_2DQuadNum_ORTH12 | n/s | n/s | 1.0451 |
| TVDV_MVRV_2dAngle_ORTH12 | n/s | n/s | 1.4645 |
| TVDV_MVRV_sin2dAngle_ORTH12[3] | n/s | n/s | 1.0525 |
| TVDV_Vorticity_ORTH123 | 0.0331 | 0.5010 | n/s |
| VD_2dArea_Quad4_ORTH12 | n/s | n/s | 1.0512 |
| VD_2dPerimeter_Quad2_ORTH13 | 0.0342 | n/s | n/s |
| VD_2dPerimeter_Quad3_ORTH12 | n/s | n/s | 1.0553 |
| VD_MaxVelocity_ORTH123 | 0.0210 | n/s | 1.0147 |
| VD_MeanCurvature_ORTH13 | n/s | n/s | 1.1044 |
| VD_SurfaceArea_AlphaShape_Octant7_ORTH123 | n/s | n/s | 1.0906 |
| VD_Volume_ConvexHull_Octant5_ORTH123 | n/s | n/s | 1.1871 |
| VD_Volume_ConvexHull_Octant7_ORTH123 | n/s | n/s | 1.0628 |
| VR_Max2dAreaQuadNum_ORTH13 | n/s | n/s | 1.1758 |
| VR_MaxCurvature_ORTH13 | n/s | n/s | 1.0796 |
| VR_Volume_AlphaShape_Octant5_ORTH123 | n/s | n/s | 1.0636 |

FA scenario = significant CAD (e.g., defined as >70% blockage and/or FFR < 0.8) (N = 464; 232 CAD positives and 232 CAD negatives (½ single and ½ multi-vessel disease) (½ are males and ½ are females)

TABLE 11B

| Feature_name | t-test | AUC | MI |
|---|---|---|---|
| lowerPPG_2dPerimeter_PPGVPG_Overall | 0.0196 | n/s | n/s |
| lowerPPG_3dMeanCurvature | n/s | 0.5151 | n/s |
| lowerPPG_3dPerimeter_Overall | 0.0405 | n/s | n/s |
| lowerPPG_AverageVelocity | 0.0245 | 0.5047 | n/s |
| lowerPPG_AverageVorticity | 0.0141 | n/s | n/s |
| lowerPPG_baseAPG_2DAngle_PPGAPG | 0.0193 | n/s | n/s |
| lowerPPG_baseAPG_2DAngle_VPGAPG | 0.0168 | n/s | n/s |
| lowerPPG_baseAPG_cos2DAngle_PPGAPG[3] | n/s | 0.5270 | 1.0897 |
| lowerPPG_baseAPG_cos2DAngle_VPGAPG[3] | n/s | 0.5320 | 1.6849 |
| lowerPPG_baseAPG_cosElevation[3] | n/s | 0.5178 | n/s |
| lowerPPG_baseVPG_2DAmplitude_PPGVPG | 0.0479 | n/s | n/s |
| lowerPPG_baseVPG_2DAmplitude_VPGAPG | n/s | n/s | 1.1978 |
| lowerPPG_baseVPG_2DAngle_PPGAPG | 0.0113 | n/s | 1.0525 |
| lowerPPG_baseVPG_2DAngle_VPGAPG | 0.0159 | 0.5259 | 1.5898 |
| lowerPPG_baseVPG_cos2DAngle_PPGAPG[3] | 0.0038 | n/s | 1.1052 |
| lowerPPG_baseVPG_cos2DAngle_PPGVPG[3] | n/s | 0.5006 | n/s |
| lowerPPG_baseVPG_cos2DAngle_VPGAPG[3] | 0.0087 | 0.5248 | 1.0845 |
| lowerPPG_baseVPG_cosElevation[3] | 0.0035 | n/s | n/s |
| lowerPPG_baseVPG_Elevation | 0.0089 | n/s | n/s |
| lowerPPG_baseVPG_sin2DAngle_PPGAPG[3] | 0.0159 | n/s | 1.0143 |
| lowerPPG_baseVPG_sin2DAngle_VPGAPG[3] | n/s | 0.5330 | 1.2265 |
| lowerPPG_baseVPG_sinElevation[3] | 0.0152 | n/s | 1.0399 |
| lowerPPG_Circulation | 0.0117 | 0.5066 | n/s |
| lowerPPG_diasPPG_2DAmplitude_VPGAPG | n/s | n/s | 1.3712 |
| lowerPPG_diasPPG_2DAngle_PPGVPG | 0.0135 | n/s | n/s |
| lowerPPG_diasPPG_cosElevation[3] | 0.0104 | n/s | n/s |
| lowerPPG_diasPPG_Elevation | 0.0179 | n/s | n/s |
| lowerPPG_diasPPG_sin2DAngle_PPGAPG[3] | 0.0258 | n/s | n/s |
| lowerPPG_diasPPG_sin2DAngle_PPGVPG[3] | 0.0090 | n/s | n/s |
| lowerPPG_diasPPG_sin2DAngle_VPGAPG[3] | 0.0200 | n/s | 1.0378 |
| lowerPPG_diasPPG_sinElevation[3] | 0.0215 | n/s | n/s |
| lowerPPG_Eccentricity_PPGVPG | 0.0212 | n/s | n/s |
| lowerPPG_minAPG_2DAngle_PPGAPG | 0.0086 | 0.5121 | n/s |
| lowerPPG_minAPG_2DAngle_PPGVPG | 0.0017 | 0.5243 | n/s |
| lowerPPG_minAPG_2DAngle_VPGAPG | 0.0038 | 0.5173 | n/s |
| lowerPPG_minAPG_cos2DAngle_PPGAPG[3] | 0.0084 | 0.5119 | n/s |
| lowerPPG_minAPG_cos2DAngle_PPGVPG[3] | 0.0021 | 0.5248 | n/s |
| lowerPPG_minAPG_cos2DAngle_VPGAPG[3] | 0.0031 | 0.5226 | n/s |
| lowerPPG_minAPG_cosElevation[3] | 0.0120 | n/s | 1.4182 |
| lowerPPG_minAPG_Elevation | 0.0163 | n/s | 1.5683 |
| lowerPPG_minAPG_sin2DAngle_VPGAPG[3] | 0.0053 | 0.5216 | n/s |
| lowerPPG_minAPG_sinElevation[3] | 0.0228 | n/s | n/s |
| lowerPPG_minVPG_2DAmplitude_PPGAPG | 0.0308 | n/s | n/s |
| lowerPPG_minVPG_2DAmplitude_VPGAPG | n/s | n/s | 1.0382 |
| lowerPPG_minVPG_2DAngle_PPGAPG | 0.0074 | 0.5142 | n/s |
| lowerPPG_minVPG_2DAngle_PPGVPG | 0.0061 | n/s | n/s |
| lowerPPG_minVPG_cos2DAngle_PPGAPG[3] | 0.0147 | 0.5073 | n/s |
| lowerPPG_minVPG_cos2DAngle_PPGVPG[3] | 0.0035 | n/s | n/s |

TABLE 11B-continued

| Feature__name | t-test | AUC | MI |
|---|---|---|---|
| lowerPPG__minVPG__sin2DAngle__PPGVPG[3] | 0.0126 | n/s | n/s |
| lowerPPG__minVPG__sin2DAngle__PPGAPG[3] | 0.0067 | 0.5093 | n/s |
| lowerPPG__peakAPG__2DAmplitude__PPGAPG | 0.0226 | n/s | n/s |
| lowerPPG__peakAPG__2DAmplitude__VPGAPG | 0.0327 | n/s | n/s |
| lowerPPG__peakAPG__2DAngle__PPGVPG | 0.0481 | 0.5047 | n/s |
| lowerPPG__peakAPG__3DAmplitude | 0.0238 | n/s | n/s |
| lowerPPG__peakAPG__sin2DAngle__VPGAPG[3] | n/s | n/s | 1.3282 |
| lowerPPG__peakAPG__sinElevation[3] | n/s | n/s | 1.0104 |
| lowerPPG__peakVPG__2DAmplitude__PPGAPG | 0.0012 | 0.5351 | 1.0339 |
| lowerPPG__peakVPG__2DAngle__PPGAPG | n/s | 0.5232 | n/s |
| lowerPPG__peakVPG__2DAngle__PPGVPG | n/s | 0.5288 | 1.5011 |
| lowerPPG__peakVPG__cos2DAngle__PPGAPG[3] | n/s | 0.5264 | n/s |
| lowerPPG__peakVPG__cos2DAngle__PPGVPG[3] | n/s | 0.5271 | 1.5180 |
| lowerPPG__peakVPG__sin2DAngle__PPGAPG[3] | 0.0032 | 0.5417 | 1.1379 |
| lowerPPG__peakVPG__sin2DAngle__PPGVPG[3] | 0.0203 | 0.5313 | n/s |
| lowerPPG__sysPPG__2DAmplitude__PPGVPG | n/s | n/s | 1.0404 |
| lowerPPG__sysPPG__2DAngle__PPGVPG | 0.0068 | n/s | n/s |
| lowerPPG__sysPPG__2DAngle__VPGAPG | 0.0162 | n/s | 1.6777 |
| lowerPPG__sysPPG__cos2DAngle__PPGVPG[3] | 0.0450 | n/s | n/s |
| lowerPPG__sysPPG__cos2DAngle__VPGAPG[3] | 0.0170 | n/s | n/s |
| lowerPPG__sysPPG__sin2DAngle__PPGVPG[3] | 0.0063 | n/s | n/s |
| lowerPPG__sysPPG__sin2DAngle__VPGAPG[3] | 0.0131 | n/s | n/s |
| lowerPPG__Circulation__PPGVPG | 0.0199 | n/s | n/s |
| upperPPG__2dArea__PPGVPG__Overall | n/s | 0.5055 | n/s |
| upperPPG__AverageVorticity | 0.0008 | 0.5201 | n/s |
| upperPPG__baseAPG__cos2DAngle__VPGAPG[3] | n/s | n/s | 1.0231 |
| upperPPG__baseVPG__2DAmplitude__PPGVPG | n/s | n/s | 1.0391 |
| upperPPG__baseVPG__sin2DAngle__PPGVPG[3] | n/s | 0.5011 | n/s |
| upperPPG__diasPPG__2DAngle__PPGAPG | 0.0366 | n/s | 1.1152 |
| upperPPG__diasPPG__2DAngle__PPGVPG | 0.0167 | n/s | 1.2321 |
| upperPPG__diasPPG__cos2DAngle__VPGAPG[3] | 0.0309 | n/s | n/s |
| upperPPG__diasPPG__cosElevation[3] | 0.0066 | n/s | n/s |
| upperPPG__diasPPG__Elevation | 0.0063 | 0.5093 | n/s |
| upperPPG__diasPPG__sin2DAngle__PPGAPG[3] | 0.0042 | 0.5079 | n/s |
| upperPPG__diasPPG__sin2DAngle__PPGVPG[3] | 0.0042 | n/s | 1.0237 |
| upperPPG__diasPPG__sin2DAngle__VPGAPG[3] | 0.0051 | 0.5105 | n/s |
| upperPPG__diasPPG__sinElevation[3] | 0.0051 | 0.5147 | n/s |
| upperPPG__MaxCurvature__PPGVPG | 0.0231 | n/s | n/s |
| upperPPG__minAPG__2DAmplitude__PPGAPG | n/s | 0.5081 | n/s |
| upperPPG__minAPG__2DAngle__PPGAPG | 0.0043 | 0.5152 | n/s |
| upperPPG__minAPG__2DAngle__PPGVPG | 0.0016 | 0.5297 | n/s |
| upperPPG__minAPG__2DAngle__VPGAPG | 0.0005 | 0.5385 | n/s |
| upperPPG__minAPG__cos2DAngle__PPGAPG[3] | 0.0043 | 0.5249 | n/s |
| upperPPG__minAPG__cos2DAngle__PPGVPG[3] | 0.0017 | 0.5099 | 1.0527 |
| upperPPG__minAPG__cos2DAngle__VPGAPG[3] | 0.0003 | 0.5399 | n/s |
| upperPPG__minAPG__cosElevation[3] | 0.0005 | 0.5345 | n/s |
| upperPPG__minAPG__Elevation | 0.0009 | 0.5379 | 1.2038 |
| upperPPG__minAPG__sin2DAngle__VPGAPG[3] | 0.0009 | 0.5391 | 1.1786 |
| upperPPG__minAPG__sinElevation[3] | 0.0014 | 0.5328 | 1.0466 |
| upperPPG__minVPG__2DAmplitude__PPGAPG | 0.0166 | n/s | n/s |
| upperPPG__minVPG__2DAmplitude__PPGVPG | n/s | n/s | 1.0006 |
| upperPPG__minVPG__2DAngle__PPGAPG | 0.0398 | n/s | n/s |
| upperPPG__minVPG__2DAngle__PPGVPG | 0.0217 | n/s | n/s |
| upperPPG__minVPG__cos2DAngle__PPGAPG[3] | 0.0184 | n/s | n/s |
| upperPPG__minVPG__cos2DAngle__PPGVPG[3] | 0.0194 | n/s | n/s |
| upperPPG__minVPG__sin2DAngle__PPGAPG[3] | 0.0407 | n/s | n/s |
| upperPPG__minVPG__sin2DAngle__PPGVPG[3] | 0.0252 | n/s | n/s |
| upperPPG__peakAPG__2DAmplitude__PPGAPG | 0.0235 | n/s | n/s |
| upperPPG__peakAPG__2DAngle__PPGVPG | 0.0137 | 0.5270 | n/s |
| upperPPG__peakAPG__2DAngle__VPGAPG | 0.0089 | 0.5104 | n/s |
| upperPPG__peakAPG__3DAmplitude | 0.0471 | n/s | n/s |
| upperPPG__peakAPG__cos2DAngle__PPGVPG[3] | n/s | 0.5107 | n/s |
| upperPPG__peakAPG__cos2DAngle__VPGAPG[3] | 0.0082 | 0.5173 | n/s |
| upperPPG__peakAPG__sin2DAngle__PPGVPG[3] | 0.0338 | 0.5056 | n/s |
| upperPPG__peakAPG__sin2DAngle__VPGAPG[3] | 0.0185 | 0.5005 | 1.1797 |
| upperPPG__peakVPG__2DAmplitude__PPGAPG | 0.0002 | 0.5507 | n/s |
| upperPPG__peakVPG__2DAmplitude__PPGVPG | n/s | 0.5073 | n/s |
| upperPPG__peakVPG__2DAmplitude__VPGAPG | n/s | 0.5120 | n/s |
| upperPPG__peakVPG__2DAngle__PPGAPG | n/s | 0.5210 | 1.0637 |
| upperPPG__peakVPG__2DAngle__PPGVPG | n/s | 0.5344 | 1.2947 |
| upperPPG__peakVPG__cos2DAngle__PPGAPG[3] | n/s | 0.5205 | n/s |
| upperPPG__peakVPG__cos2DAngle__PPGVPG[3] | n/s | 0.5317 | 2.1142 |

TABLE 11B-continued

| Feature_name | t-test | AUC | MI |
|---|---|---|---|
| upperPPG_peakVPG_sin2DAngle_PPGAPG[3] | 0.0005 | 0.5543 | 1.2604 |
| upperPPG_peakVPG_sin2DAngle_PPGVPG[3] | 0.0014 | 0.5633 | 1.2200 |
| upperPPG_sysPPG_2DAmplitude_VPGAPG | n/s | n/s | 1.5237 |

FA scenario = significant CAD (e.g., defined as >70% blockage and/or FFR < 0.8) (N = 464; 232 CAD positives and 232 CAD negatives (½ single and ½ multi-vessel disease) (½ are males and ½ are females)
[3]= cos/sin-encoding associated features.

The determination that certain visual features have clinical utility in estimating the presence and non-presence of elevated LVEDP or the presence and non-presence of significant CAD provides a basis for the use of these visual features or parameters, as well as other features described herein, in estimating for the presence or non-presence and/or severity and/or localization of other diseases, medical condition, or an indication of either particularly, though not limited to, heart disease or conditions described herein.

Example Clinical Evaluation System

FIG. 12A shows an example clinical evaluation system 1200 (also referred to as a clinical and diagnostic system) that implements the modules of FIG. 1 to non-invasively compute visual features or parameters, along with other features or parameters, to generate, via a classifier (e.g., machine-learned classifier), one or more metrics associated with the physiological state of a patient or subject according to an embodiment. Indeed, the feature modules (e.g., of FIGS. 1, 4, and 5) can be generally viewed as a part of a system (e.g., the clinical evaluation system 1200) in which any number and/or types of features may be utilized for a disease state, medical condition, an indication of either, or combination thereof that is of interest, e.g., with different embodiments having different configurations of feature modules. This is additionally illustrated in FIG. 12A, where the clinical evaluation system 1200 is of a modular design in which disease-specific add-on modules 1202 (e.g., to assess for elevated LVEDP or mPAP, CAD, PH/PAH, abnormal LVEF, HFpEF, and others described herein) are capable of being integrated alone or in multiple instances with a singular platform (i.e., a base system 1204) to realize system 1200's full operation. The modularity allows the clinical evaluation system 1200 to be designed to leverage the same synchronously acquired biophysical signals and data set and base platform to assess for the presence of several different diseases as such disease-specific algorithms are developed, thereby reducing testing and certification time and cost.

In various embodiments, different versions of the clinical evaluation system 1200 may implement the assessment system 103 (FIG. 1) by having included containing different feature computation modules that can be configured for a given disease state(s), medical condition(s), or indicating condition(s) of interest. In another embodiment, the clinical evaluation system 1200 may include more than one assessment system 103 and may be selectively utilized to generate different scores specific to a classifier 116 of that engine 103. In this way, the modules of FIGS. 1 and 12 in a more general sense may be viewed as one configuration of a modular system in which different and/or multiple engines 103, with different and/or multiple corresponding classifiers 116, may be used depending on the configuration of module desired. As such, any number of embodiments of the modules of FIG. 1, with or without the visual specific feature(s), may exist.

In FIG. 12A, System 1200 can analyze one or more biophysical-signal data sets (e.g., 110) using machine-learned disease-specific algorithms to assess for the likelihood of elevated LVEDP, as one example, of pathology or abnormal state. System 1200 includes hardware and software components that are designed to work together in combination to facilitate the analysis and presentation of an estimation score using the algorithm to allow a physician to use that score, e.g., to assess for the presence or non-presence of a disease state, medical condition, or an indication of either.

The base system 1204 can provide a foundation of functions and instructions upon which each add-on module 1202 (which includes the disease-specific algorithm) then interfaces to assess for the pathology or indicating condition. The base system 1204, as shown in the example of FIG. 12A, includes a base analytical engine or analyzer 1206, a web-service data transfer API 1208 (shown as "DTAPI" 1208), a report database 1210, a web portal service module 1213, and the data repository 111 (shown as 112*a*).

Data repository 112*a*, which can be cloud-based, stores data from the signal capture system 102 (shown as 102*b*). Biophysical signal capture system 102*b*, in some embodiments, is a reusable device designed as a single unit with a seven-channel lead set and photoplethysmogram (PPG) sensor securely attached (i.e., not removable). Signal capture system 102*b*, together with its hardware, firmware, and software, provides a user interface to collect patient-specific metadata entered therein (e.g., name, gender, date of birth, medical record number, height, and weight, etc.) to synchronously acquire the patient's electrical and hemodynamic signals. The signal capture system 102*b* may securely transmit the metadata and signal data as a single data package directly to the cloud-based data repository. The data repository 112*a*, in some embodiments, is a secure cloud-based database configured to accept and store the patient-specific data package and allow for its retrieval by the analytical engines or analyzer 1206 or 1214.

Base analytical engine or analyzer 1206 is a secure cloud-based processing tool that may perform quality assessments of the acquired signals (performed via "SQA" module 1216), the results of which can be communicated to the user at the point of care. The base analytical engine or analyzer 1206 may also perform pre-processing (shown via pre-processing module 1218) of the acquired biophysical signals (e.g., 110—see FIG. 1). Web portal 1213 is a secure web-based portal designed to provide healthcare providers access to their patient's reports. An example output of the web portal 1213 is shown by visualization 1236. The report databases (RD) 1212 is a secure database and may securely interface and communicate with other systems, such as a hospital or physician-hosted, remotely hosted, or remote electronic health records systems (e.g., Epic, Cerner, Allscrips, CureMD, Kareo, etc.) so that output score(s) (e.g., 118) and related information may be integrated into and saved with the patient's general health record. In some embodiments, web portal 1213 is accessed by a call center to provide the output clinical information over a telephone.

Database 1212 may be accessed by other systems that can generate a report to be delivered via the mail, courier service, personal delivery, etc.

Add-on module 1202 includes a second part 1214 (also referred to herein as the analytical engine (AE) or analyzer 1214 and shown as "AE add-on module" 1214) that operates with the base analytical engine (AE) or analyzer 1206. Analytical engine (AE) or analyzer 1214 can include the main function loop of a given disease-specific algorithm, e.g., the feature computation module 1220, the classifier model 1224 (shown as "Ensemble" module 1224), and the outlier assessment and rejection module 1224 (shown as "Outlier Detection" module 1224). In certain modular configurations, the analytical engines or analyzers (e.g., 1206 and 1214) may be implemented in a single analytical engine module.

The main function loop can include instructions to (i) validate the executing environment to ensure all required environment variables values are present and (ii) execute an analysis pipeline that analyzes a new signal capture data file comprising the acquired biophysical signals to calculate the patient's score using the disease-specific algorithm. To execute the analysis pipeline, AE add-on module 1214 can include and execute instructions for the various feature modules 114 and classifier module 116 as described in relation to FIG. 1 to determine an output score (e.g., 118) of the metrics associated with the physiological state of a patient. The analysis pipeline in the AE add-on module 1214 can compute the features or parameters (shown as "Feature Computation" 1220) and identifies whether the computed features are outliers (shown as "Outlier Detection" 1222) by providing an outlier detection return for a signal-level response of outlier vs. non-outlier based on the feature. The outliers may be assessed with respect to the training data set used to establish the classifier (of module 116). AE add-on module 1214 may generate the patient's output score (e.g., 118) (e.g., via classifier module 1224) using the computed values of the features and classifier models. In the example of an evaluation algorithm for the estimation of elevated LVEDP, the output score (e.g., 118) is an LVEDP score. For the estimation of CAD, the output score (e.g., 118) is a CAD score.

The clinical evaluation system 1200 can manage the data within and across components using the web-service DTAPIs 1208 (also may be referred to as HCPP web services in some embodiments). DTAPIs 1208 may be used to retrieve acquired biophysical data sets from and to store signal quality analysis results to the data repository 112*a*. DTAPIs 1208 may also be invoked to retrieve and provide the stored biophysical data files to the analytical engines or analyzers (e.g., 1206, 1214), and the results of the analytical engine's analysis of the patient signals may be transferred using DTAPI 1208 to the report database 1210. DTAPIs 1208 may also be used, upon a request by a healthcare professional, to retrieve a given patient data set to the web portal module 1213, which may present a report to the healthcare practitioner for review and interpretation in a secure web-accessible interface.

Clinical evaluation system 1200 includes one or more feature libraries 1226 that store the visual features 120 and various other features of the feature modules 122. The feature libraries 1226 may be a part of the add-on modules 1202 (as shown in FIG. 12A) or the base system 1204 (not shown) and are accessed, in some embodiments, by the AE add-on module 1214.

Further details of the modularity of modules and various configurations are provided in U.S. Provisional Patent Application No. 63/235,960, filed Aug. 19, 2021, entitled "Modular Disease Assessment System," which is hereby incorporated by reference herein in its entirety.

Example Operation of the Modular Clinical Evaluation System

Figure 12B:
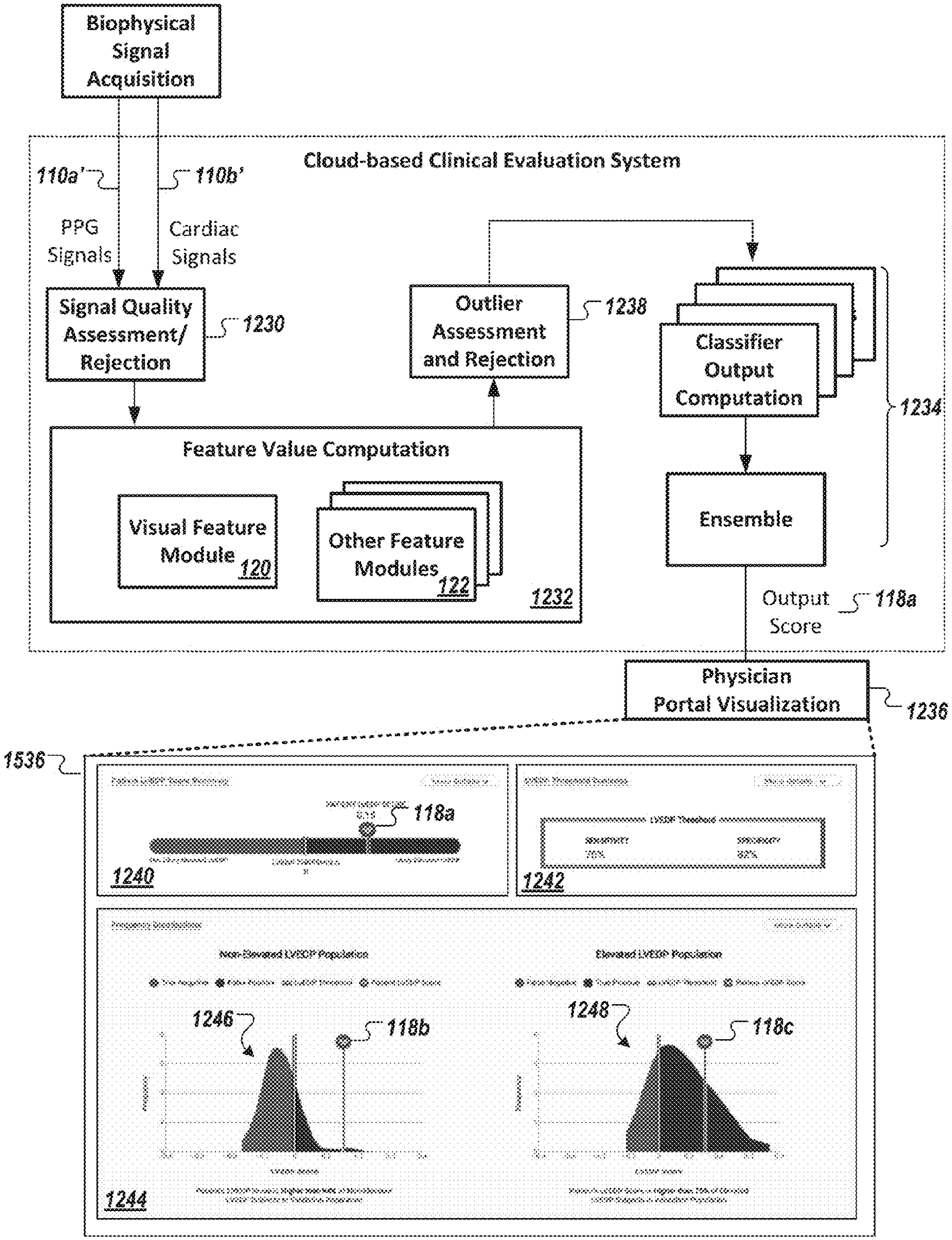
FIG. 12B shows a schematic diagram of the operation of the example clinical evaluation system of FIG. 15A in accordance with an illustrative embodiment.

FIG. 12B shows a schematic diagram of the operation and workflow of the analytical engines or analyzers (e.g., 1206 and 1214) of the clinical evaluation system 1200 of FIG. 12A in accordance with an illustrative embodiment.

Signal quality assessment/rejection (1230). Referring to FIG. 12B, the base analytical engine or analyzer 1206 assesses (1230), via SQA module 1216, the quality of the acquired biophysical-signal data set while the analysis pipeline is executing. The results of the assessment (e.g., pass/fail) are immediately returned to the signal capture system's user interface for reading by the user. Acquired signal data that meet the signal quality requirements are deemed acceptable (i.e., "pass") and further processed and subjected to analysis for the presence of metrics associated with the pathology or indicating condition (e.g., elevated LVEDP or mPAP, CAD, PH/PAH, abnormal LVEF, HFpEF) by the AE add-on module 1214. Acquired signals deemed unacceptable are rejected (e.g., "fail"), and a notification is immediately sent to the user to inform the user to immediately obtain additional signals from the patient (see FIG. 2).

The base analytical engine or analyzer 1206 performs two sets of assessments for signal quality, one for the electrical signals and one for the hemodynamic signals. The electrical signal assessment (1230) confirms that the electrical signals are of sufficient length, that there is a lack of high-frequency noise (e.g., above 170 Hz), and that there is no power line noise from the environment. The hemodynamic signal assessment (1230) confirms that the percentage of outliers in the hemodynamic data set is below a pre-defined threshold and that the percentage and maximum duration that the signals of the hemodynamic data set are railed or saturated is below a pre-defined threshold.

Feature Value Computation (1232). The AE add-on module 1214 performs feature extraction and computation to calculate feature output values. In the example of the LVEDP algorithm, the AE add-on module 1214 determines, in some embodiments, a total of 446 feature outputs belonging to 18 different feature families (e.g., generated in modules 120 and 122), including the visual features (e.g., generated in module 120). For the CAD algorithm, an example implementation of the AE add-on module 1214 determines a set of features, including 456 features corresponding to the same 18 feature families.

Additional descriptions of the various features, including those used in the LVEDP algorithm and other features and their feature families, are described in U.S. Provisional Patent Application No. 63/235,960, filed Aug. 23, 2021, entitled "Method and System to Non-Invasively Assess Elevated Left Ventricular End-Diastolic Pressure"; U.S. Provisional Patent Application No. 63/236,072, filed Aug. 23, 2021, entitled "Methods and Systems for Engineering Visual Features From Biophysical Signals for Use in Characterizing Physiological Systems"; U.S. Provisional Patent Application No. 63/235,963, filed Aug. 23, 2021, entitled "Methods and Systems for Engineering Power Spectral Features From Biophysical Signals for Use in Characterizing Physiological Systems"; U.S. Provisional Patent Application No. 63/235,966, filed Aug. 23, 2021, entitled "Method and System for Engineering Rate-Related Features From Biophysical Signals for Use in Characterizing Physiological Systems"; U.S. Provisional Patent Application No. 63/235,968, filed Aug. 23, 2021, entitled "Methods and Systems for Engineering Wavelet-Based Features From Biophysical Signals for Use in Characterizing Physiological Systems"; U.S. Provisional Patent Application No. 63/130,324, titled "Method and System to Assess Disease Using Cycle Variability Analysis of Cardiac and Photoplethysmographic Signals"; U.S. Provisional Patent Application No. 63/235,971, filed Aug. 23, 2021, entitled "Methods and Systems for Engineering photoplethysmographic Waveform Features for Use in Characterizing Physiological Systems"; U.S. Provisional Patent Application No. 63/236,193, filed Aug. 23, 2021, entitled "Methods and Systems for Engineering Cardiac Waveform Features From Biophysical Signals for Use in Characterizing Physiological Systems"; U.S. Provisional Patent Application No. 63/235,974, filed Aug. 23, 2021, entitled "Methods and Systems for Engineering Conduction Deviation Features From Biophysical Signals for Use in Characterizing Physiological Systems," each of which is hereby incorporated by reference herein in its entirety.

Classifier Output Computation (1234). The AE add-on module 1214 then uses the calculated feature outputs in classifier models (e.g., machine-learned classifier models) to generate a set of model scores. The AE add-on module 1214 joins the set of model scores in an ensemble of the constituent models, which, in some embodiments, averages the output of the classifier models as shown in Equation 6 in the example of the LVEDP algorithm.

$$\text{Esemble estimation} = \frac{Model_1 + Model_2 + \ldots + Model_n}{n} \quad \text{(Equation 6)}$$

In some embodiments, classifier models may include models that are developed based on ML techniques described in U.S. Patent Publication No. 20190026430, entitled "Discovering Novel Features to Use in Machine Learning Techniques, such as Machine Learning Techniques for Diagnosing Medical Conditions"; or U.S. Patent Publication No. 20190026431, entitled "Discovering Genomes to Use in Machine Learning Techniques," each of which is hereby incorporated by reference herein in its entirety.

In the example of the LVEDP algorithm, thirteen (13) machine-learned classifier models are each calculated using the calculated feature outputs. The 13 classifier models include four ElasticNet machine-learned classifier models [9], four RandomForestClassifier machine-learned classifier models [10], and five extreme gradient boosting (XGB) classifier models [11]. In some embodiments, the patient's metadata information, such as age, gender, and BMI value, may be used. The output of the ensemble estimation may be a continuous score. The score may be shifted to a threshold value of zero by subtracting the threshold value for presentation within the web portal. The threshold value may be selected as a trade-off between sensitivity and specificity. The threshold may be defined within the algorithm and used as the determination point for test positive (e.g., "Likely Elevated LVEDP") and test negative (e.g., "Not Likely Elevated LVEDP") conditions.

In some embodiments, the analytical engine or analyzer can fuse the set of model scores with a body mass index-based adjustment or an adjustment based on age or gender. For example, the analytical engine or analyzer can average the model estimation with a sigmoid function of the patient BMI having the form $$\text{sigmoid}(x) = \frac{1}{1 + e^{-x}}.$$

Physician Portal Visualization (1236). The patient's report may include a visualization 1236 of the acquired patient data and signals and the results of the disease analyses. The analyses are presented, in some embodiments, in multiple views in the report. In the example shown in FIG. 12B, the visualization 1236 includes a score summary section 1240 (shown as "Patient LVEDP Score Summary" section 1240), a threshold section 1242 (shown as "LVEDP Threshold Statistics" section 1242), and a frequency distribution section 1244 (shown as "Frequency Distribution" section 1208). A healthcare provider, e.g., a physician, can review the report and interpret it to provide a diagnosis of the disease or to generate a treatment plan.

The healthcare portal may list a report for a patient if a given patient's acquired signal data set meets the signal quality standard. The report may indicate a disease-specific result (e.g., elevated LVEDP) being available if the signal analysis could be performed. The patient's estimated score (shown via visual elements 118*a*, 118*b*, 118*c*) for the disease-specific analysis may be interpreted relative to an established threshold.

In the score summary section 1240 shown in the example of FIG. 12B, the patient's score 118*a* and associated threshold are superimposed on a two-tone color bar (e.g., shown in section 1240) with the threshold located at the center of the bar with a defined value of "0" representing the delineation between test positive and test negative. The left of the threshold may be lightly shaded light and indicates a negative test result (e.g., "Not Likely Elevated LVEDP"), while to the right of the threshold may be darkly shaded to indicate a positive test result (e.g., "Likely Elevated LVEDP").

The threshold section 1242 shows reported statistics of the threshold as provided to a validation population that defines the sensitivity and specificity for the estimation of the patient score (e.g., 118). The threshold is the same for every test regardless of the individual patient's score (e.g., 118), meaning that every score, positive or negative, may be interpreted for accuracy in view of the provided sensitivity and specificity information. The score may change for a given disease-specific analysis as well with the updating of the clinical evaluation.

The frequency distribution section 1244 illustrates the distribution of all patients in two validation populations (e.g., (i) a non-elevated population to indicate the likelihood of a false positive estimation and (ii) an elevated population to indicate a likelihood of a false negative estimation). The graphs (1246, 1248) are presented as smooth histograms to provide context for interpreting the patient's score 118 (e.g., 118*b*, 118*c*) relative to the test performance validation population patients.

The frequency distribution section 1240 includes a first graph 1246 (shown as "Non-Elevated LVEDP Population" 1246) that shows the score (118*b*), indicating the likelihood of the non-presence of the disease, condition, or indication, within a distribution of a validation population having non-presence of that disease, condition, or indication and a second graph 1248 (shown as "Elevated LVEDP Population" 1248) that shows the score (118*c*), indicates the likelihood of the presence of the disease, condition, or indication, within a distribution of validation population having the presence of that disease, condition, or indication. In the example of the assessment of elevated LVDEP, the first graph 1246 shows a non-elevated LVEDP distribution of the validation population that identifies the true negative (TN) and false positive (FP) areas. The second graph 1248 shows an elevated LVEDP distribution of the validation population that identifies the false negative (TN) and true positive (FP) areas.

The frequency distribution section 1240 also includes interpretative text of the patient's score relative to other patients in a validation population group (as a percentage). In this example, the patient has an LVEDP score of −0.08, which is located to the left side of the LVEDP threshold, indicating that the patient has "Not Likely Elevated LVEDP."

The report may be presented in the healthcare portal, e.g., to be used by a physician or healthcare provider in their diagnosis for indications of left-heart failure. The indications include, in some embodiments, a probability or a severity score for the presence of a disease, medical condition, or an indication of either.

Outlier Assessment and Rejection Detection (1238). Following the AE add-on module 1214 computing the feature value outputs (in process 1232) and prior to their application to the classifier models (in process 1234), the AE add-on module 1214 is configured in some embodiments to perform outlier analysis (shown in process 1238) of the feature value outputs. Outlier analysis evaluation process 1238 executes a machine-learned outlier detection module (ODM), in some embodiments, to identify and exclude anomalous acquired biophysical signals by identifying and excluding anomalous feature output values in reference to the feature values generated from the validation and training data. The outlier detection module assesses for outliers that present themselves within sparse clusters at isolated regions that are out of distribution from the rest of the observations. Process 1238 can reduce the risk that outlier signals are inappropriately applied to the classifier models and produce inaccurate evaluations to be viewed by the patient or healthcare provider. The accuracy of the outlier module has been verified using hold-out validation sets in which the ODM is able to identify all the labeled outliers in a test set with the acceptable outlier detection rate (ODR) generalization.

While the methods and systems have been described in connection with certain embodiments and specific examples, it is not intended that the scope be limited to the particular embodiments set forth, as the embodiments herein are intended in all respects to be illustrative rather than restrictive. The visual features discussed herein may ultimately be employed to make, or to assist a physician or other healthcare provider in making, noninvasive diagnoses or determinations of the presence or non-presence and/or severity of other diseases, medical conditions, or indication of either, such as, e.g., coronary artery disease, pulmonary hypertension and other pathologies as described herein using similar or other development approaches. In addition, the example analysis, including the visual features, can be used in the diagnosis and treatment of other cardiac-related pathologies and indicating conditions as well as neurological-related pathologies and indicating conditions, such assessment can be applied to the diagnosis and treatment (including surgical, minimally invasive, and/or pharmacologic treatment) of any pathologies or indicating conditions in which a biophysical signal is involved in any relevant system of a living body. One example in the cardiac context is the diagnosis of CAD, and other diseases, medical conditions, or indicating conditions disclosed herein and its treatment by any number of therapies, alone or in combination, such as the placement of a stent in a coronary artery, the performance of an atherectomy, angioplasty, prescription of drug therapy, and/or the prescription of exercise, nutritional and other lifestyle changes, etc. Other cardiac-related pathologies or indicating conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other diseases such as blood or other disorders), as well as other cardiac-related pathologies, indicating conditions and/or diseases. Non-limiting examples of neurological-related diseases, pathologies or indicating conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, indicating conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/indicating conditions and vision-related diseases/indicating conditions.

In addition, the clinical evaluation system described herein may be configured to analyze biophysical signals such as an electrocardiogram (ECG), electroencephalogram (EEG), gamma synchrony, respiratory function signals, pulse oximetry signals, perfusion data signals; quasi-periodic biological signals, fetal ECG signals, blood pressure signals; cardiac magnetic field signals, heart rate signals, among others.

Further examples of processing that may be used with the exemplified method and system disclosed herein are described in: U.S. Pat. Nos. 9,289,150; 9,655,536; 9,968,275; 8,923,958; 9,408,543; 9,955,883; 9,737,229; 10,039,468; 9,597,021; 9,968,265; 9,910,964; 10,672,518; 10,566,091; 10,566,092; 10,542,897; 10,362,950; 10,292,596; 10,806,349; U.S. Patent Publication nos. 2020/0335217; 2020/0229724; 2019/0214137; 2018/0249960; 2019/0200893; 2019/0384757; 2020/0211713; 2019/0365265; 2020/0205739; 2020/0205745; 2019/0026430; 2019/0026431; PCT Publication nos. WO2017/033164; WO2017/221221; WO2019/130272; WO2018/158749; WO2019/077414; WO2019/130273; WO2019/244043; WO2020/136569; WO2019/234587; WO2020/136570; WO2020/136571; U.S. patent application Ser. Nos. 16/831,264; 16/831,380; 17/132,869; PCT Application nos. PCT/IB2020/052889; PCT/IB2020/052890, each of which is hereby incorporated by reference herein in its entirety.

What is claimed is:

1. A method to non-invasively assess a metric associated with a cardiac disease state or abnormal condition of a subject, the method comprising:

simultaneously acquiring, by one or more processors and via one or more surface sensors placed on the subject while the subject is at rest, a biophysical signal data set of the subject including at least one cardiac signal and a photoplethysmogram (PPG) signal;

generating, by the one or more processors, a phase space model of the biophysical signal data set;

generating, by the one or more processors, an orthogonal projection of the phase space model of the biophysical signal data set, wherein the orthogonal projection defines a plurality of orthogonal planes;

determining, by the one or more processors and based, in part, on the orthogonal projection of the phase space model, values of a plurality of visual-predictor associated properties of a plurality of waveform regions of interest in the biophysical signal data set, wherein the visual-predictor associated properties characterize properties of repetitive cycles between the at least one cardiac signal and the PPG signal, wherein the visual-predictor associated properties include characteristics of projections of cardiac vectors onto the plurality of orthogonal planes and within a quadrant region of a respective orthogonal plane, and wherein the plurality of waveform regions of interest comprises an atrial repolarization (AR) waveform region, a ventricular repolarization (VR) waveform region, and a ventricular depolarization (VD) waveform region;

determining, by the one or more processors and by assessing morphologies and variability associated with the plurality of waveform regions of interest, an estimated value for presence of a metric associated with the cardiac disease state or abnormal condition based, in part, on an application of the determined values of the one or more visual-predictor associated properties to a trained visual-based machine learning model; and generating or modifying, by the one or more processors, a treatment parameter for the subject in response to determining based on the estimated value that the subject has the cardiac disease state or abnormal condition, wherein the subject is treated with surgery or medication based, at least in part, on the treatment parameter.

2. The method of claim 1, wherein the biophysical signal data set comprises biopotential signals acquired for three channels of measurements.

3. The method of claim 1, wherein the biophysical signal data set comprises photoplethysmographic signals acquired from optical sensors.

4. The method of claim 1 further comprising:

determining, by the one or more processors, one or more values of one or more features extracted from the phase space model, wherein the one or more features are selected from the group consisting of:

a feature associated with a three-dimensional perimeter of the phase space model;

a feature associated with an area enclosed in a max fit plane determined in the phase space model;

a feature associated with a three-dimensional mean curvature or three-dimensional maximum curvature determined in the phase space model;

a feature associated with a macroscopic measure of a rotation of points that defines a loop in the phase space model;

a feature associated with an average of a magnitude of curl vectors determined in the phase space model; and a feature associated with a Euclidean distance between consecutive points in a loop defined in the phase space model.

5. The method of claim 1, further comprising:

determining, by the one or more processors, one or more values of one or more features extracted from the orthogonal projection, wherein the one or more features are selected from the group consisting of:

a feature associated with a two-dimensional perimeter of a loop defined in the orthogonal projection;

a feature defining a quadrant having a maximum two-dimensional perimeter of the loop defined in the orthogonal projection;

a feature associated with a two-dimensional area of the loop defined in the orthogonal projection;

a feature defining a quadrant having a maximum two-dimensional area of the loop defined in the orthogonal projection;

a feature associated with an eccentricity of the loop defined in the orthogonal projection;

a feature associated with a two-dimensional mean curvature or two-dimensional maximum curvature determined in the orthogonal projection; and a feature associated with a macroscopic measure of a rotation of points that defines the loop in the orthogonal projection.

6. The method of claim 1, further comprising:

determining, by the one or more processors, one or more values of one or more features extracted from the biophysical signal data set comprising a photoplethysmographic signal or a derivative thereof, wherein the one or more features are selected from the group consisting of:

a feature defined by a vector joining a pre-defined origin landmark in the photoplethysmographic signal to a peak location determined in the photoplethysmographic signal;

a feature defined by a vector joining i) the pre-defined origin landmark in a velocity-plethysmographic signal derived from the photoplethysmographic signal to ii) a peak location determined in the velocity-plethysmographic signal;

a feature defined by a vector joining i) the pre-defined origin landmark in the velocity-plethysmographic signal derived from the photoplethysmographic signal to ii) a minimum location determined in the velocity-plethysmographic signal;

a feature defined by a vector joining i) the pre-defined origin landmark in the velocity-plethysmographic signal derived from the photoplethysmographic signal to ii) a base location determined in the velocity-plethysmographic signal;

a feature defined by a vector joining i) the pre-defined origin landmark in an acceleration-plethysmographic signal derived from the photoplethysmographic signal to ii) a peak location determined in the acceleration-plethysmographic signal;

a feature defined by a vector joining i) the pre-defined origin landmark in the acceleration-plethysmographic signal derived from the photoplethysmographic signal to ii) a minimum location determined in the acceleration-plethysmographic signal; and a feature defined by a vector joining i) the pre-defined origin landmark in the acceleration-plethysmographic signal derived from the photoplethysmographic signal to ii) a base location determined in the acceleration-plethysmographic signal.

7. The method of claim 1, further comprising:
determining, by the one or more processors, one or more values of features extracted from the biophysical signal data set, wherein the one or more features are selected from the group consisting of:
a feature defined by a three-dimensional vector joining a pre-defined origin landmark in a cardiac signal peak landmark in a cardiac signal;
a feature defined by a three-dimensional vector joining a pre-defined origin landmark in the photoplethysmographic signal to a peak, a minimum, or a base location determined in the photoplethysmographic signal;
a feature defined by an elevation angle defining the three-dimensional vector joining the pre-defined origin landmark to the peak landmark in the cardiac signal;
a feature defined by a three-dimensional vector joining i) the pre-defined origin landmark in a velocity-plethysmographic signal derived from the photoplethysmographic signal to ii) a peak, a minimum, or a base location determined in the velocity-plethysmographic signal;
a feature defined by a three-dimensional vector joining i) the pre-defined origin landmark in an acceleration-plethysmographic signal derived from the photoplethysmographic signal to ii) a peak, a minimum, or a base location determined in the acceleration-plethysmographic signal;
a feature defined by an elevation angle defining the three-dimensional vector joining the pre-defined origin landmark in the photoplethysmographic signal to the peak, the minimum, or the base location determined in the photoplethysmographic signal;
a feature defined by an elevation angle defining the three-dimensional vector joining i) the pre-defined origin landmark in the velocity-plethysmographic signal derived from the photoplethysmographic signal to ii) the peak, the minimum, or the base location determined in the velocity-plethysmographic signal; and
a feature defined by an elevation angle defining the three-dimensional vector joining i) the pre-defined origin landmark in the acceleration-plethysmographic signal derived from the photoplethysmographic signal to ii) the peak, the minimum, or the base location determined in the acceleration-plethysmographic signal.

8. The method of claim 4, further comprising:
determining, by the one or more processors, one or more values of features extracted from the biophysical signal data set comprising a photoplethysmographic signal or a derivative thereof, wherein the one or more features are selected from the group consisting of:
a feature defined by a two-dimensional magnitude of a vector defined between i) an origin location in a projection of one or more of orthogonal planes defined in the phase space model and ii) a peak, a minimum, or a base location in the orthogonal plane; and
a feature defined by an angle of the vector defined between i) the origin location in the projection of the one or more of the orthogonal planes defined in the phase space model and ii) the peak, the minimum, or the base location in the orthogonal plane.

9. The method of claim 4, further comprising:
determining, by the one or more processors, one or more values of features extracted from the biophysical signal data set comprising a photoplethysmographic signal or a derivative thereof, wherein the one or more features includes a feature defined by a surface area or a volume parameter of a defined geometric shape in the phase space model.

10. The method of claim 9, wherein the defined geometric shape comprises an alpha hull shape or a convex hull shape.

11. The method of claim 1 further comprising:
causing, by the one or more processors, generation of a visualization of the estimated value for the presence of the disease state or abnormal condition, wherein the generated visualization is rendered and displayed at a display of a computing device and/or presented in a report.

12. The method of claim 1, wherein the values of one or more visual-predictor associated properties are used in the estimation model selected from the group consisting of a linear model, a decision tree model, a random forest model, a support vector machine model, a neural network model.

13. The method of claim 12, wherein the model further includes features selected from the group consisting of:
one or more depolarization or repolarization wave propagation associated features;
one or more depolarization wave propagation deviation associated features;
one or more cycle variability associated features;
one or more dynamical system associated features;
one or more cardiac waveform topologic and variations associated features;
one or more PPG waveform topologic and variations associated features;
one or more cardiac or PPG signal power spectral density associated features;
one or more cardiac or PPG signal visual associated features; and
one or more predictability features.

14. The method of claim 1, wherein the cardiac disease state or abnormal condition is selected from the group consisting of coronary artery disease, pulmonary hypertension, pulmonary arterial hypertension, pulmonary hypertension due to left heart disease, rare disorders that lead to pulmonary hypertension, left ventricular heart failure or left-sided heart failure, right ventricular heart failure or right-sided heart failure, systolic heart failure, diastolic heart failure, ischemic heart disease, and arrhythmia.

15. The method of claim 1, further comprising:
acquiring, by one or more acquisition circuits of a measurement system, voltage gradient signals over one or more channels, wherein the voltage gradient signals are acquired at a frequency greater than about 1 kHz; and
generating, by the one or more acquisition circuits, the obtained biophysical data set from the acquired voltage gradient signals.

16. The method of claim 15, further comprising:
acquiring, by one or more acquisition circuits of a measurement system, one or more photoplethysmographic signals; and
generating, by the one or more acquisition circuits, the obtained biophysical data set from the acquired voltage gradient signals.

17. The method of claim 1, wherein the one or more processors are located in a cloud platform.

18. The method of claim 1, wherein the one or more processors are located in a local computing device.

19. A system comprising:

a processor; and a memory having instructions stored thereon, wherein execution of the instructions by the processor cause the processor to:

simultaneously acquire, via one or more surface sensors placed on a subject while the subject is at rest, a biophysical signal data set of a subject including at least one cardiac signal and photoplethysmogram (PPG) signal;

generate a phase space model of the biophysical signal data set;

generate an orthogonal projection of the phase space model of the biophysical signal data set, wherein the orthogonal projection defines a plurality of orthogonal planes;

determine based at least in part on the orthogonal projection of the phase space model, values of a plurality of visual-predictor associated properties of a plurality of waveform regions of interest in the biophysical signal data set, wherein the visual-predictor associated properties characterize properties of repetitive cycles between the at least one cardiac signal and PPG signal, and wherein the plurality of waveform regions of interest comprises an atrial repolarization (AR) waveform region, a ventricular repolarization (VR) waveform region, and a ventricular depolarization (VD) waveform region;

determine, by assessing morphologies and variability associated with the plurality of waveform regions of interest, an estimated value for presence of a metric associated with a cardiac disease state or abnormal condition based, in part, on an application of the determined values of the one or more visual-predictor associated properties to a trained visual-based machine learning model; and generate or modify a treatment parameter for the subject in response to determining based on the estimated value that the subject has the cardiac disease state or abnormal condition, wherein the subject is treated with surgery or medication based, at least in part, on the treatment parameter.

20. A non-transitory computer readable medium having instructions stored thereon, wherein execution of the instructions by a processor causes the processor to:

simultaneously acquire, via one or more surface sensors placed on a subject while the subject is at rest, a biophysical signal data set of a subject including at least one cardiac signal and photoplethysmogram (PPG) signal;

generate a phase space model of the biophysical signal data set;

generate an orthogonal projection of the phase space model of the biophysical signal data set, wherein the orthogonal projection defines a plurality of orthogonal planes;

determine based at least in part on the orthogonal projection of the phase space model, values of a plurality of visual-predictor associated properties of a plurality of waveform regions of interest in the biophysical signal data set, wherein the visual-predictor associated properties characterize properties of repetitive cycles between the at least one cardiac signal and PPG signal, and wherein the plurality of waveform regions of interest comprises an atrial repolarization (AR) waveform region, a ventricular repolarization (VR) waveform region, and a ventricular depolarization (VD) waveform region;

determine, by assessing morphologies and variability associated with the plurality of waveform regions of interest, an estimated value for presence of a metric associated with a cardiac disease state or abnormal condition based, in part, on an application of the determined values of the one or more visual-predictor associated properties to a trained visual-based machine learning model; and generate or modify a treatment parameter for the subject in response to determining based on the estimated value that the subject has the cardiac disease state or abnormal condition, wherein the subject is treated with surgery or medication based, at least in part, on the treatment parameter.

* * * * *